(12) United States Patent
McCray, Jr. et al.

(10) Patent No.: US 6,855,549 B1
(45) Date of Patent: Feb. 15, 2005

(54) METHODS AND COMPOSITIONS FOR INCREASING THE INFECTIVITY OF GENE TRANSFER VECTORS

(75) Inventors: Paul B. McCray, Jr., Iowa City, IA (US); Guoshun Wang, Iowa City, IA (US); Beverly Davidson, North Liberty, IA (US); Mordechai Bodner, San Diego, CA (US); Steven M. Herrmann, San Diego, CA (US); Douglas J. Jolly, Encinitas, CA (US)

(73) Assignees: The University of Iowa Research Foundation, Iowa City, IA (US); Chiron Corporation, Emeryville, CA (US)

( * ) Notice: Subject to any disclaimer, the term of this patent is extended or adjusted under 35 U.S.C. 154(b) by 0 days.

(21) Appl. No.: 09/448,613

(22) Filed: Nov. 22, 1999

Related U.S. Application Data
(60) Provisional application No. 60/109,475, filed on Nov. 23, 1998.

(51) Int. Cl.$^7$ .......................... C12N 15/86; C12Q 1/68; A01N 43/04
(52) U.S. Cl. ..................... 435/456; 435/69.1; 514/44
(58) Field of Search .............................. 435/456, 69.1; 514/44

(56) References Cited

U.S. PATENT DOCUMENTS

| | | | |
|---|---|---|---|
| 5,139,941 A | 8/1992 | Muzyczka et al. | 435/172.3 |
| 5,196,335 A | 3/1993 | Groner | 435/240.2 |
| 5,252,479 A | 10/1993 | Srivastava | 435/235.1 |
| 5,354,855 A | 10/1994 | Cech et al. | 536/24.1 |
| 5,359,046 A | 10/1994 | Capon et al. | 536/23.4 |
| 5,543,399 A | 8/1996 | Riordan et al. | 514/21 |
| 5,641,662 A | 6/1997 | Debs et al. | 435/172.1 |
| 5,658,894 A | * 8/1997 | Weisz | 514/58 |
| 5,756,353 A | 5/1998 | Debs | 435/375 |
| 5,962,429 A | * 10/1999 | Welch | 514/44 |

FOREIGN PATENT DOCUMENTS

| | | |
|---|---|---|
| WO | WO 90/07469 | 7/1990 |
| WO | WO 93/12240 | 6/1993 |
| WO | WO 96/22765 | 8/1996 |
| WO | WO 96/27393 | 9/1996 |
| WO | WO 96/32116 | 10/1996 |

OTHER PUBLICATIONS

Lacaz–Vieira (Journal of General Physiology, (Dec. 1997) 110 (6) 727–40).*
Sakoff et al (Biochemical and Molecular Medicine, (Apr. 1997) 57 (2) 81–90).*
Cho et al (Pharmaceutical Research, (Apr. 1990) 7 (4) 325–31).*
Noach et al (International Journal of Pharmaceutics (1993), 90(3), 229–37).*
Allen et al (Development, (Apr. 1990) 108 (4) 623–34).*
Mariadason et al (Am. J. Physiol. (1997) 272:G705–G712.*
Marano et al (Biochem. Biophys. Res. Comm. (1995) 209(2):669–676).*
Wong et al (J. Cell Biol. (1997) 1363(2): 399–409).*
Li et al (Biochimica Et Biophysica Acta, (Dec. 14, 1990) 1030 (2) 297–300).*
The Dictionary of Cell and Molecular Biology (retrieved from http://www.mblab.gla.ac.uk/~julian/Dict.html on May 9, 2003.*
Jiang et al (Eur. J. Hum. Genet. (1998) 6(1):12–31).*
Rodgers et al (Eur. Respir. J (2001): 17:1314–1321).*
O'Dea et al (Current Gene Therapy (2002) 2:173–181).*
Ferrari et al (Clin Exp. Immunol. (2003) 132: 1–8).*
Kaplan et al (Human Gene Therapy (1998) 9(10):1469–1479).*
Kleeberger et al (Applied Phys. (1992) 72(2): 670–676).*
Johnson et al (J. Virol. (1998) 72(11):8861–8872).*
Olsen et al (Nucl. Acids Res. (1993) 21(3):663–669).*
Quinn et al (J. Cell. Phys (1996) 168(1):34–41.*
Katkin et al (Human Gene Therapy 1997 3(9):75–779).*
Cornetta et al (J. Virol. Methods (1989) 23(2): 187–194).*
Debs et al (J. Immunol. 1988 140(10): 3482–3488).*
Jongeneel et al (Nucl. Acids Res. (1980) 8(7): 1661–1673).*
Tomita et al (Journal of Pharmaceutical Sciences, (1996 Jun) 85 (6) 608–11).*
Zegarra–Moran et al (British Journal of Pharmacology, (1995 Mar) 114 (5) 1052–6).*
Meza et al (Journal of Cellular Biochemistry, (1982) 18 (4) 407–21).*
McEwan et al (Biochim. Biophys. Acta (1993) 1148(1):51–60.*
Arcasoy et al (Gene Therapy (1997) 4(1): 32–38).*
Richardson et al (Lab. Invest. (1976) 35(4): 307–314).*
Yap et al (Exp. Cell Res. (1995) 218(2): 540–550).*
Hahimoto et al (Biochim. Biophys. Acta (1997) 1323(2): 281–290).*
Welsh et al (J. Clin. Invest. (1985) 76: 155–1168).*
Flasshove et al (Blood (1995) 85(2): 566–574).*

(List continued on next page.)

*Primary Examiner*—Dave T. Nguyen
*Assistant Examiner*—Richard Schnizer
(74) *Attorney, Agent, or Firm*—Fulbright & Jaworski LLP

(57) ABSTRACT

The present invention involves methods and compositions for increasing the susceptibility of target cells to transduction by gene transfer vectors. Specifically, it is proposed that increasing intracellular permeability in epithelial tissue increases the percentage of input vector that will transduce that target tissue. Specific examples show that receptors for retrovirus are preferentially accessible on the basolateral surface of airway epithelia, and permeabilizing such tissues results in greater infection with retrovirus. This has important implications in gene therapy, for example, to treat cystic fibrosis with the CFTR gene.

34 Claims, 9 Drawing Sheets

OTHER PUBLICATIONS

Figure 1:
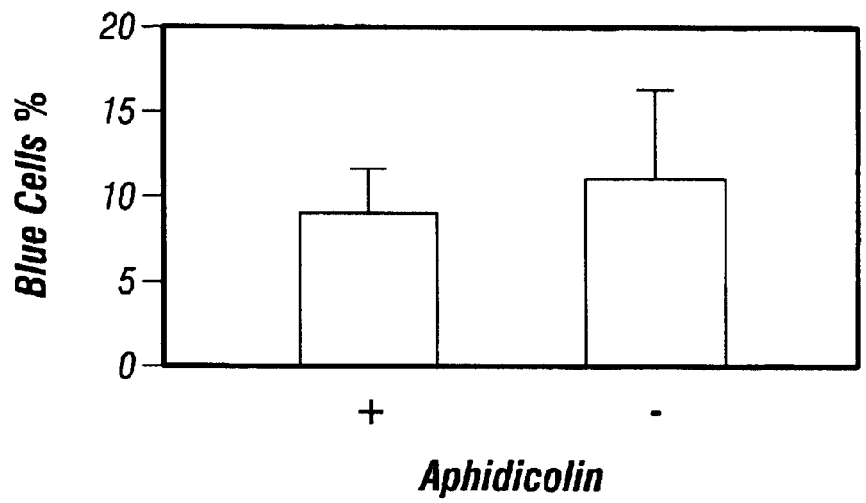

Wunderlich et al (Archives of Virology, (1982) 73 (2) 171–83).*
Orkin et.al.; Report and Recommendations of the Panel to Assess the NIH Investment in Research on Gene Therapy, 1995.*
Verma et.al.; Gene therapy– promises, problems and prospects, 1997, Nature, vol. 389: 239–242.*
Rosenecker et.al.; Toward Gene Therapy of Cystic Fibrosis, 1998, Eur. J Med. Res. 3: 149–156.*
Davies et.al.; Prospects for gene therapy for cystic fibrosis, 1998, Molecula Medicine Today: 292–299.*
Wilson; Gene Therapy for Cystic Fibrosis: Challenges and Future Directions, 1995, J Clin. Invest., vol. 96: 2547–2554.*
Flotte et.al.; Gene Therapy in Cystic Fibrosis, 2001, Chest 120: 124S–131S.*
Rosenfeld et.al.; Gene Therapy for Cystic Fibrosis, 1996, Chest 109: 241–252.*
Yamaguchi et.al.; Differential Effects of Transforming Growth Factor–B on Osteoclast–Like Cell Formation in Mouse Marrow Culture: Relation to the Effect of Zinc–Cheklating Dipeptides, 1995, Peptides, vol. 16, No. 8: 1483–1488.*
Mallea et.al.; Modulation of stimulatory action of follicle stimulating hormone (FSH) and inhibitory action of epidermal growth factor (EGF) on aromatase activity in Sertoil cells by calcium, 1987, FEB, vol. 218, No. 1: 143–147.*
Halbert et.al.; Retroviral Vectors Efficiently Transduce Basal and Secretory Airway Epithelial Cells In Vitro Resulting om Persistent Gene Expression in Organotypic Culture, 1996, Human Gene Therapy 7: 1871–1881.*
Boucher; Status of gene therpay for cystic fibrosis lung disease, 1999, Journal of Clinical Investigation, vol. 103, No. 4: 441–445.*
Boucher; Current status of CF gene therapy, 1996, TIG, vol. 12., No. 3: 81–84.*
Alton; Gene therapy: the case for cystic fibrosis, 1997, Journal of the Royal Society of Medicine: 43–46.*
Medline: 2001324122.*
Medline 83073940.*
Alexander et al., "DNA–damaging agents greatly increase the transition of nondividing cells by adeno–associated virus vectors," *J. Virol.,* 68, 8282–8287, 1994.
Alexander et al. "Transfer of contaminants in adeno–associated virus vector stocks can mimic transduction and lead to artifactual results," *Hum. Gene Ther.,* 8:1911–1902, 1997.
Anderson et al., "Demonstration that CFTR is a chloride channel by alteration of its anion sleectivity," *Science,* 253:202–205, 1991.
Anderson and Van Itallie, "Tight junctions and the molecular basis for regulation of paracellular permeability," *Am. J. Physiol.,* 269:G467–G475, 1995.
Basak and Compans, "Polarized entry of canine parovirus in an epithelial cell line," *J. Virol.,* 63:3164–3167, 1989.
Bhat et al., "Regulation of tight junction permeability by calcium mediators and cell cytoskeleton in rabbit tracheal epithelium," *Pharm. Res.,* 10:991–997, 1993.
Blau and Compans, "Entry and release of measles virus are polarized in epithelial cells," *Virology,* 210:91–99, 1995.
Bosch et al., "Proliferation induced by keratinocyte growth factor enhances in vivo retroviral–mediated gene transfer to mouse hepatocytes," *J. Clin. Invest.,* 98:2683–2687, 1996.

Bosch et al., "Effects of keratonocyte and hepatocyte growth factor in vivo: Implication for retrovirus–mediated gene transfer to liver," *Hum. Gene Ther.,* 9:1747–1754, 1998.
Boucher et al., "Airway transepithelial electric potential in vivo: species and regional differences," *J. Appl. Physiol.,* 48:169–176, 1980.
Bowles et al., "A simple and efficient method for the concentration and purification of recombinant retrovirus for increased hepatocyte transduction in vivo," *Hum. Gene Ther.,* 7:1735–1742, 1996.
Cereijido et al., "Role of tight junctions in establishing and maintaining cell polarity," *Annu. Rev. Physio.,* 60:161–177, 1998.
Chan et al., "Regional deposition of nebulized hypodense nonisotonic solutions in the human respiratory tract," *Eur. Respir. J.,* 7:1483–1489, 1994.
Chu et al., "Binding and uptake of cationic lipid:pDNA complexes by polarized airway epithelial cells," *Hum. Gene Ther.,* 10:25–36, 1999.
Clayson and Compans, "Entry of simian virus 40 is restricted to apical surfaces of polarized epithelial cells," *Mol. Cell Biol.,* 8:3391–3396, 1988.
Colledge et al., "Generation and characterization of a ΔF508 cystic fibrosis mouse model," *Nature Genet.,* 10:445–452, 1995.
Denker and Nigam, "Molecular structure and assembly of the tight junction," *Am J Physiol,* 274:F1–F9, 1998.
Drumm et al., "Correction of the cystic fibrosis defect in vitro by retrovirus–mediated gene transfer," *Cell,* 62:1227–1233, 1990.
Duan et al., "Structural and functional heterogeneity of interated recombinant AAV genomes" *Virus Res.,* 48:41–56, 1997.
Duan et al., "Circular intermediates of recombinant adeno–associated virus have defined structural characteristics responsible for long term episomal persistence in muscle," *J. Virol.* 72:8568–8577, 1998.
Duan et al., "Polarity influences the efficiency of recombinant adeno–associated virus infection in differentiated airway epithelia," *Hum. Gene Ther.,* 9:2761–2776, 1998.
Engelhardt et al., "In vivo retroviral gene transfer into human bronchial epithelia of xenografts," *J. Clin. Invest.,* 90:2598–2607, 1992.
Flotte et al., "Stable in vivo expression of the cystic fibrosis transmembrane conductance regulator with an adeno–associated virus vector," *Proc. Natl. Acad. Sci. USA,* 90:10613–10617, 1993.
Furuse et al., "Claudin–1 and –2:Novel integral membrane proteins localizing at tight junctions with no sequence similarity to occludin," *J. Cell Biol.,* 141:1539–1550, 1998.
Furuse et al., "Occludin: a novel integral membrane protein localizing at tight junctions." *J. Cell Biol.,* 123:1777–1788, 1993.
Furuse et al., "A single gene product, claudin–1 or –2, reconstitutes tight junction strands and recruits occludin in fibroblasts," *J. Cell Biol.,* 143:391–401, 1998.
Goldman et al., "Lentiviral vectors for gene therapy of cystic fibrosis," *Hum. Gene Ther.,* 8:2261–2268, 1997.
Green and Jones, "Desmosomes and hemidesmosomes: structure and function of molecular components," *FASEB J,* 10:871–881, 1996.
Grubb et al, "Inefficient gene transfer by adenovirus vector to cystic fibrosis airway epithelia of mice and humans," *Nature,* 371:802–806, 1994.

Gumbiner, "Breaking through the tight junction barrier," *J. Cell Biol.*, 123:1631–1633, 1993.

Halbert et al., "Retroviral vectors efficiently transduce basal and secretory airway epithelial cells in vitro resulting in persistent gene expression in organotypic culture," *Hum. Gene Ther.*, 7:1871–1881, 1996.

Halbert et al., "Adeno–associated virus vectors transduce primary cells much less efficiently than immortalized cells," *J. Virol.*, 69:1473–1479, 1995.

Halbert, et al., "Transduction by adeno–associated virus vectors in the rabbit airway: Efficiency, persistence, and readministration," *J. Virol.*, 71:5932–5941, 1997.

Halbert et al., Successful readministration of adeno–associated virus vectors to the mouse lung requires transient immunosuppression during the initial exposure, *J. Virol.*, 72:9795–9805, 1998.

Housley et al., "Keratinocyte growth factor induces proliferation of hepatocytes and epithelial cells throughout the rat gastrointestinal tract," *J. Clin. Invest.*, 94:1764–1777, 1994.

Inayama et al., "The differentiation potential of tracheal basal cells," *Lab. Invest.*, 58:706–717, 1988.

Jarnigan et al. "Bioelectric properties and ion transport of excised rabbit trachea," *J. Appl. Physiol.*, 55:1884–1892, 1983.

Johnson and Hubbs, "Epithelial progenitor cells in the rat trachea," *Am. J. Respir. Cell Mol. Biol.*, 3:579–585, 1990.

Johnson et al., "Effect of host modification and age on airway epithelial gene transfer mediated by a murine leukemia virus–derived vector," *J. Virol.*, 72:8861–8872, 1998.

Johnson et al., "Efficiency of gene transfer for restoration of Normal airway epithelial function in cystic fibrosis," *Nature Genet.*, 2:21–25, 1992.

Johnston et al., "Minimum requirements for efficient transduction of dividing and nondividing cells by feline immunodeficiency virus vectors," *J. Virol.*, 73:4991–5000, 1999.

Jolly, "Viral vector systems for gene therapy," *Can. Gene Ther.*, 1:51–64, 1994.

Kaplan et al., "Humoral and cellular immune responses of nonhuman primates to long–term repeated lung exposure to Ad2/CFTR–2," *Gene Ther.*, 3:117–127, 1996.

Kent et al., "Phenotypic abnormalities in long–term surviving cystic fibrosis mice," *Pediatr. Res.*, 40:233–241, 1996.

Kitten et al., "Highly efficient retrovirus–mediated gene transfer into rat hepatocytes in vivo," *Hum. Gene Ther.*, 8:1491–1494, 1997.

Knecht and Shelden, "Three–dimensional localization of wild–type and myosin II mutant cells during morphogenesis of dictyostelium," *Dev. Biol.*, 170:434–444, 1995.

Kondo et al., "Simple technique for culture of highly differentiated cells from dog tracheal epithelium," *Am J Physiol.*, 263:L106–L117, 1991.

Leigh et al., "Cell proliferation in bronchial epithelium and submucosal glands of cystic fibrosis patients," *Am. J. Respir. Cell Mol. Biol.*, 12:605–612, 1995.

Liu et al., "Pseudotransduction of heaptocytes by using concentrated pseudotyped vesicular stomatitis virus G glycoprotein (VSV–G)moloney murine leukemia virus–derived retrovirus vectors: comparison of VSV–G and amphotropic vectors for hepatic gene transfer," *J. Virol.*, 70:2497–2502, 1996.

Mason et al., "Hepatocyte growth factor is a growth factor for a rat alveolar type cells," *Am. J. Respir. Cell Mol. Biol.*, 11:561–567, 1994.

McCormack et al., "Anti–vector immunoglobulin induced by retroviral vectors," *Hum. Gene Ther.*, 8:1263–1273, 1997.

McCray et al., "Expression of CFTR and a cAMP–stimulated chloride secretory current in cultured human fetal alveolar epithelial cells," *Am. J. Respir. Cell Mol. Biol.*, 9:578–585, 1993.

McCray et al., "Alveolar macrophages inhibit retrovirus–mediated gene transfer to airway epithelia," *Gene Ther.*, 8:1087–1093, 1997.

McCray Jr. et al., "Adenoviral–mediated gene transfer to fetal pulmonary epithelia in vitro and in viva," *Clin. Invest.*, 95:2620–2632, 1995.

McCray Jr. et al., "Proliferation indices of pulmonary epithelia during human and ovine lung development: gene transfer targets for integrating vectors" *Cell Vision*, 4:1–8, 1997.

McCray Jr. et al., "Efficient killing of inhaled bacteria in deltaF508 mice: role of airway surface liquid composition," *Am. J. Physiol.*, 277:L183–L190, 1999.

Miller and Miller, "A family of retroviruses that utilize related phosphate transporters for cell entry," *J Virol.*, 68:8270–8276, 1994.

Miller, et al., "Cloning of the cellular receptor for amphotrophic murine retroviruses reveals homology to that for gibbon ape leukimia virus," *Proc. Nat'l Acad Sci. USA*, 91:78–82, 1994.

Miller, "Cell–surface receptors for retroviruses and implication for gene transfer," *Proc. Nat'l Acad. Sci. USA*, 93:11407–11413, 1996.

Ohmichi et al., "In vivo mitogenic action of HGF on lung epithelial cells: pulmotrophic role in lung regeneration," *Am. J. Physiol.*, 270:L1031–L1039, 1996.

Olsen et al., "Correction of the apical membrane chloride permeability defect in polarized cystic fibrosis airway epithelia following retroyiral–mediated gene transfer," *Hum. Gene Ther.*, 3:253–266, 1992.

Pickles et al. "Limited entry of adenovirus vectors into well–differentiated airway epithelium is responsible for inefficient gene transfer," *J. Virol.*, 72:6014–6023, 1998.

Qing et al., "Adeno–associated virus type 2–mediated gene transfer: correlation of tyrosine phosphorylation of the cellular single–stranded D sequence–binding protein with transgene expresion in human cells in vitro and murine tissues in vivo," *J. Virol.*, 72:1593–1599, 1998.

Qing et al., "Role of tyrosine phosphorylation of a cellular protein in adeno–associated virus 2–mediated transgene expression," *Proc. Natl. Acad. Sci. U.S.A.*, 94:10879–10884, 1997.

Randell, "Progenitor–progeny relationships in airway epithelium," *Chest*, 101:11S–16S, 1992.

Richardson and Bank, "Developmental–stage–specific expression and regulation of an amphotrophic retroviral receptor in hematopoietic cells," *Mol. Cell. Biol.*, 16:4240–4247, 1996.

Rodriguez et al., "Vaccinia virus preferentially enters polarized epithelial cells through the basolateral surface," *J. Virol.*, 65:494–498, 1991.

Rubin et al., "Keratinocyte growth factor," *Cell Biol. Int.*, 19:399–411, 1995.

Russell et al., "DNA synthesis and topoisomerase inhibitors increase transduction by adeno–associated virus vectors," *Proc. Natl. Acad. Sci. U.S.A.*, 92:5719–5723, 1995.

Russell et al., "Adeno–associated virus vectors preferentially transduce cells in S phase," *Proc. Natl. Acad. Sci. U.S.A.,* 91:8915–8919, 1994.

Scaria et al., "Adenovirus–mediated persistent cystic fibrosis transmembrane conductance regulator expression in mouse airway epithelium," *J. Virol.,* 72:7302–7309, 1998.

Shami and Evans, "Kinetics of pulmonary cells. In Comparative biology of the normal lung," R.A. Parent, editor, CRC Press, Boca Raton, 145–155, 1991.

Simon et al., "Adenovirus–mediated transfer of the CFTR gene to lung of nonhuman primates: toxicity study," *Hum. Gene Ther.,* 4:771–780, 1993.

Snouwaert et al., "A murine model of cystic fibrosis," *Am. Respir. Crit. Care Med.* 151:S59–S64, 1995.

Stern et al. "The effect of mucolytic agents on gene transfer across a CF sputum barrier in vitro," *Gene Ther.,* 5, 91–98, 1998.

Summerford and Samulski, "Membrane–associated heparan sulfate proteoglycan is a receptor for adeno–associated virus type 2 virions," *J. Virol.,* 72, 1438–1445.

Teramoto et al., "Factors influencing adeno–associated virus–medited gene transfer to human cystic fibrosis airway epithelial cells: comparison with adenovirus vectors," *J. Virol.,* 72:8904–8912, 1998.

Thomas and Roth, "The basolateral targeting signal in the cytoplasmic domain of glycoprotein G from vesicular stomatitis virus resembles a variety of intracellular targeting motifs related by primary sequence but having diverse targeting activities," *J. Biol. Chem.,* 269:15732–15739, 1994.

Tugizov et al., "Role of apical and basolateral membranes in replication of human cytomegalvirus in polarized retinal pigment epithelial cells," *J. Gen. Virol.,* 77:61–74, 1996.

Ulich et al., "Keratinocyte growth factor is a growth factor for type II pneumocytes in vivo," *J. Clin. Invest.,* 93:1298–1306, 1994.

van Zeijl et al., "A human amphotrophic retrovirus receptor is a second member of gibbon ape leukimia virus receptor family," *Proc. Nat'l Acad. Sci. USA,* 91:1168–1172, 1994.

Walters et al., "Basolateral localization of fiber receptors limits adenovirus infection of airway epithelia," *J. Biol. Chem.,* 274:10219–10226, 1999.

Wang et al., "Influence of cell polarity on retrovirus–mediated gene transfer to differentiated human airway epithelia," *J. Virol.,* 72:9818–9826, 1998.

Wang et al., "Keratinocyte growth factor induced epithelial proliferation facilitates retroviral–mediated gene transfer to pulmonary epithelia in vivo," *J. Gene. Med.,* 1:22–30, 1999.

Weiss and Tailor, "Retrovirus receptors," *Cell,* 82:531–533, 1995.

Welsh et al., "Cystic fibrosis," *McGraw–Hill, Inc.,* 3799–3876, 1995.

Widdicombe et al., "Transient permeabilization of airway epithelium by mucosal water," *J. Appl. Physiol.,* 81:491–499, 1996.

Yamaya et al., "Differentiated structure and function of cultures from human tracheal epithelium," *Am. J. Physiol.,* 262:L713–L724, 1992.

Yamaya et al., "Altered ion transport tracheal glands in cystic fibrosis," *Am. J. Physiol.* 261:L491–L494, 1991.

Zabner et al., "Adenovirus–mediated gene transfer transiently corrects the chloride transport defect in nasal epithelia of patients with cystic fibrosis," *Cell,* 75:207–216, 1993.

Zabner et al., "Cellular and molecular barriers to gene transfer by a cationic lipid," *J. Biol. Chem.,* 270:18997–19007, 1995.

Zabner et al. "Repeat administration of an adenovirus vector encoding cystic fibrosis transmembrane conductance regulator to the nasal epithelium of patients with cystic fibrosis." *J. Clin. Invest.,* 97:1504–1511, 1996.

Zabner et al., "Loss of CFTR chloride channels alters salt absorption by cystic fibrosis airway epithelia in vitro," *Mol. Cell,* 2:397–403, 1998.

Zabner et al., "Adenovirus–mediated gene transfer to ciliated airway epithelia requires prolonged incubation time," *J Virol.,* 70:6994–7003, 1996.

Zeiher et al., "A mouse model for the ΔF508 allele of cystic fibrosis," *J. Clin. Invest.* 96:2051–2064, 1995.

Zhang et al., "Genotypic analysis of respiratory mucous sulfation defects in cystic fibrosis.," *J. Clin. Invest.* 96, 2997–3004, 1995.

Zhang et al., "Vector–specific complementation profiles of two independent primary defects in cystic fibsosis airways," *Hum. Gene Ther.,* 9:635–648, 1998.

Zsengeller et al., "Keratinocyte growth factor stimulates transduction of the respiratory epithelium by retroviral vectors," *Hum. Gene Ther.,* 10:341–353, 1999.

Zsengeller et al., Persistence of replication–deficient adenovirus–mediated gene transfer in lungs of immune–deficient (nu/nu) mice, *Hum. Gene Ther.,* 6:457–467, 1995.

Crystal, "Bad for cats, good for humans? Modified feline immunodeficiency virus for gene therapy," *J. Clinical Investigation,* 104(11):1491–1493, 1999.

Lemarchand et al., "In vivo adenovirus–mediated gene transfer to lungs via pulmonary artery," *J. Appl. Physiol.,* 76(6):2840–2845, 1994.

Wang et al., "Feline immunodeficiency virus vectors persistently transduce nondividing airway epithelia and correct the cystic fibrosis defect," *J. Clinical Investigation,* 104:R55–R62, 1999.

Wang et al., "Increasing epithelial junction permeability enhances gene transfer to airway epithelia In Vivo," *Am. J. Respir. Cell Mol. Biol.,* 22:129–138, 2000.

Zhou et al., "Correction of lethal intestinal defect in a mouse model of cystic fibrosis by human CFTR," *Science,* 266:1705–1708, 1994.

* cited by examiner

US 6,855,549 B1

METHODS AND COMPOSITIONS FOR INCREASING THE INFECTIVITY OF GENE TRANSFER VECTORS

The present application claims the benefit of U.S. Provisional Patent Application Serial No. 60/109,475 filed Nov. 23, 1998. The government owns rights in the present invention pursuant to grant number R01HL61460 from the National Institutes of Health.

BACKGROUND OF THE INVENTION

1. Field of the Invention

The present invention relates to the fields of virology, cellular and molecular biology. More particularly, the invention relates to the development of a method for increasing the susceptibility of epithelial cells to infection by viruses and viral vectors, including viral vectors and other vectors used in the gene therapy. Thus, the invention also relates to the delivery of therapeutic genes to diseased tissues.

2. Description of Related Art

Numerous diseases exist which are the result of congenital and acquired genetic defects. Diseases resulting from congenital inherited defects include cystic fibrosis (CF) and various other genetic deficiencies. CF is a common, recessive disease characterized by decreased chloride ion permeability in epithelial tissues (Quinton, 1990). While several tissues are affected by the disease, it is chronic lung disease that causes 95% of the mortality associated with CF (Welsh et al., 1995). The CF gene product has been identified (Tsui et al., 1989) and is called cystic fibrosis transmembrane conductance regulator (CFTR). Over 800 different mutations of CFTR have been associated with clinical disease. Studies have established that transfer of the wild-type CFTR cDNA into CF epithelia corrects the characteristic CF defect in chloride ion secretion (Rich et al., 1990; Drumm et al., 1990).

Another important genetic disease is cancer. Cancer is usually the result of an accumulation of genetic damage, most of which is acquired, but some of which may be the result of congenital genetic defects. As described by Foulds (1958), cancer is usually the product of a multistep biological process, which is presently known to occur by the accumulation of genetic damage. On a molecular level, the multistep process of tumorigenesis involves the disruption of both positive and negative regulatory effectors (Weinberg, 1989). The molecular basis for human colon carcinomas has been postulated by Vogelstein and coworkers (1990) to involve a number of oncogenes, tumor suppressor genes and repair genes. Similarly, defects leading to the development of retinoblastoma have been linked to another tumor suppressor gene (Lee et al., 1987). Still other oncogenes and tumor suppressors have been identified in a variety of other malignancies.

The development of effective gene therapies therefore is critical to the treatment of chronic and progressive diseases resulting from genetic defects. Gene transfer to epithelial cells in particular would be required for treatment of numerous diseases caused by genetic defects effecting epithelial tissue. Examples of such diseases include lung cancer, tracheal cancer, asthma, surfactant protein B deficiency, alpha-1-antitrypsin deficiency and cystic fibrosis.

However, transfer of foreign DNAs into human cells in vivo has proved to be a challenging undertaking. Various viral vectors have been designed for use in gene therapy in order to deliver foreign DNA to human tissues, including retrovirus (both murine virus and lentivirus), adenovirus, papilloma virus, herpesvirus, parvovirus and poxivirus. Non-viral vectors including naked DNA, DNA complexed with lipids, or other conjugates may be used as well. All of these vectors have been successful, but there remain various obstacles that limit the efficacy of these vectors. One of the most serious obstacles to be overcome in gene therapy is low cellular viral infection rates, and therefore low gene transfer efficiency, particularly in non-dividing cells.

Thus, there remains a need to improve the efficiency of infection of target cells, in the context of gene therapy, by various viral and non-viral vectors. With the current interest in gene therapy, the need for improving the existing gene therapy vectors is greater than ever.

SUMMARY OF THE INVENTION

Therefore, it is an objective of the present invention to provide a method for increasing the gene transfer efficiency to epithelial tissue when using viruses and viral vectors. It is also an objective to provide a means of targeting gene transfer to all the cells in the epithelial sheet, including basal cells. It also is an objective to provides compositions for use in these methods.

In accordance with the foregoing objectives, there is provided, in one embodiment, a method of increasing the susceptibility of epithelial cells to viral infection by increasing the transepithelial permeability. The epithelial cells may be of any epithelial tissue type but, in particular embodiments is airway epithelial tissue, most particularly airway epithelial tissue selected from the group of tracheal, bronchial, bronchiolar and alveolar tissue.

In another embodiment the susceptibility of epithelial cells to viral infection by increasing the transepithelial permeability may be further modified by increasing the proliferation of the epithelial cells by contacting them with a proliferative factor. Any proliferative factor may be used, but in a particular embodiment the proliferative factor is a growth factor. In further embodiments, the proliferative factor may be delivered as an aerosol or as a topical solution.

In a further embodiment method of increasing the susceptibility of epithelial cells to viral infection by increasing the transepithelial permeability of epithelial tissue, the increase in transepithelial permeability is achieved by contacting the epithelial tissue with a tissue permeabilizing agent. Any tissue permeabilizing agent may be used, but in specific embodiments, the tissue permeabilizing agent is selected from a group including hypotonic solutions, ion chelators, cationic peptides, occludin peptides, peptides designed to disrupt extracellular portions of the junctional complexes, cytoskeletal disruption agents, antibodies, ether, neurotransmitters, glycerol, FCCP, oxidants, and mediators of inflammation. In further specific embodiments, the ion chelator may be EGTA, BAPTA or EDTA; the cationic peptide may be poly-L-lysine; the cytoskeletal disruption agent may be cytochalasin B or colchicine; the neurotransmitter may be capsianoside; the oxidant may be hydrogen peroxide or ozone; and the mediator of inflammation may be TNFα. The antibody may be an anti-E-cadherin antibody. Finally, in yet another embodiment, the tissue permeabilizing agent may be delivered as an aerosol or as a topical solution.

Yet another embodiment provides a method of increasing the susceptibility of epithelial cells to viral infection by increasing the transepithelial permeability via the peracellular route, further comprising infecting the epithelial tissue with a virus vector selected from the group including virus from the virus families retrovirus, adenovirus, parvovirus, papovavirus and paramyxovirus, from the virus genera lentivirus and adeno-associated virus, and the vaccinia virus. This embodiment is further modified in still further embodiments wherein the viral vector contains a non-viral gene under the control of a promoter active in eukaryotic cells. Any non-viral gene may be used, but in a particular embodiment the non-viral gene is a human gene, and in yet another embodiment the human gene encodes a polypeptide selected from the group consisting of a tumor suppressor, a cytokine, an enzyme, a toxin, a growth factor, a membrane channel, an inducer of apoptosis, a transcription factor, a hormone and a single chain antibody. In another embodiment the virus vector may be a replication-defective virus, and in a further embodiment the replication-defective virus is a retroviral vector.

In still another embodiment there is provided a method of increasing the susceptibility of epithelial cells to viral infection by increasing the transepithelial permeability wherein the epithelial tissue is diseased. In a further embodiment the disease of the epithelial tissue may be lung cancer, tracheal cancer, asthma, surfactant protein B deficiency, alpha-1-antitrypsin deficiency or cystic fibrosis.

As a further embodiment, the invention provides a composition comprising both a tissue permeabilizing agent and a cell proliferative factor suitable for aerosol application, and in another embodiment, suitable for topical application. Any tissue permeabilizing agent may be used in either composition, but in a further embodiment the tissue permeabilizing agent of the composition is selected from the group of a hypotonic solution, a cytokine, a cationic peptide, a cytoskeletal disrupter, a mediator of inflammation, an oxidant, a neurotransmitter or an ion chelator. It is understood that any proliferative factor can be used in the aforementioned compositions. An additional embodiment of the compositions further comprises a packaged viral vector. The packaged viral vector in other embodiments comprises a non-viral gene or is a retroviral vector or other gene transfer vector.

The invention also provides a method for redistributing the viral receptors or enhancing accessibility of viral receptors on epithelial cells of an epithelial tissue by increasing the transepithelial permeability of the epithelial tissue. This may involve opening the paracellular pathway and allowing vectors free access to receptors on the basalateral membrane. Any viral receptor may be redistributed, but in another embodiment the viral receptor is a retroviral receptor.

The invention provides a further embodiment which is a method for expressing a polypeptide in cells of an epithelial tissue comprising the steps of (a) providing a packaged viral vector comprising a polynucleotide encoding said polypeptide; (b) increasing the permeability of said epithelial tissue; and (c) contacting cells of the epithelial tissue with the packaged viral vector under conditions permitting the uptake of the packaged viral vector by the cells and expression of said polypeptide therein. Other embodiments of this method further comprises increasing the proliferation of cells in the epithelial tissue or further comprises a viral vector which is a retroviral vector.

Also, the invention provides a method for treating epithelial tissue disease comprising the steps of (a) providing a packaged viral vector comprising a polynucleotide encoding the therapeutic polypeptide; (b) increasing the permeability of the diseased epithelial tissue; and (c) contacting cells of the epithelial tissue with the packaged viral vector under conditions permitting the uptake of the packaged viral vector by the cells and expression of the therapeutic polypeptide therein, whereby expression of the therapeutic polypeptide treats the disease. A further embodiment of the method comprises increasing the proliferation of the cells of the diseased epithelial tissue. Any means of increasing the proliferation of the cells of the diseased epithelial tissue may be used but a in further embodiment the means of increasing the proliferation is contacting the epithelial cells with a proliferative agent. Another further embodiment of the method comprises a method in which the diseased epithelial tissue being treated is airway tissue. Any airway tissue may be treated, but a further embodiment treats airway tissue selected from the group of alveolar tissue, bronchiolar tissue, bronchial tissue and tracheal tissue. A further embodiment of the method is one which comprises the treatment of epithelial tissue disease wherein the disease is cancer. Any cancer may be treated but further embodiments are directed to the treatment of lung cancer or tracheal cancer.

In still another embodiment of the method, the epithelial tissue disease being treated is an inherited genetic defect. The invention is directed to any inherited genetic defect, but further embodiments are specifically directed to the inherited genetic defects surfactant protein B deficiency, alpha-1-antitrypsin deficiency or cystic fibrosis. The method for treating an epithelial tissue disease has a further embodiment wherein the method further comprises the use of a therapeutic polypeptide selected from the group consisting of a tumor suppressor, a cytokine, an enzyme, a toxin, a growth factor, a membrane channel, an inducer of apoptosis, a transcription factor, a hormone and a single chain antibody. Another embodiment of the method for treating epithelial tissue disease is one in which the step of increasing the permeability of the diseased epithelial tissue comprises contacting cells of said diseased epithelial tissue with a tissue permeabilizing agent. Finally, the method of treating an epithelial tissue disease has an embodiment in which the viral vector used is specifically a retroviral vector.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 VSV-G pseudotyped FIV vector transduces non-dividing airway epithelia in vitro. Aphidicolin growth-arrested cells are transduced readily (mean±SE, n=5 epithelia, 3 different preparations).

FIG. 2A and FIG. 2B. Recombinant FIV vector expressing CFTR corrects the cystic fibrosis $Cl^{31}$ transport defect. CF airway epithelial cells were transduced from the apical surface in the presence of EGTA with ~10 MOI of FIV vector expressing either β-galactosidase or human CFTR. For comparison, another group of CF cells were treated with Ad2/CFTR (MOI 50, basolateral application). At time points of 3, 13, 30, 60, 90 and 180 days later, epithelia were mounted in Ussing chambers and the change in short circuit current measured in response to cAMP agonists ($\Delta Isc_{(IBMx/Forsk)}$). FIG. 2A. Comparison of ($\Delta Isc_{(IBMx/Forsk)}$) in response to cAMP agonists in CF epithelia transduced with adenovirus or FIV vectors expressing CFTR, 3 days following gene transfer. Both Ad and FIV transduced epithelia express cAMP activated Cl currents similar to normal cells (n=5 CF epithelia, n=5 normal epithelia for each time point). FIG. 2B. CFTR expression persists in FIV transduced epithelia. CF epithelia were transduced with FIV-pgal, FIV- CFTR or Ad2/CFTR and ($\Delta Isc_{(IBMx/Forsk)}$) measured at the indicated time points following gene transfer (n=5 CF epithelia, n=5 normal epithelia for each time point). Data from each study were normalized to the mean ($\Delta Isc_{(IBMx, Forsk)}$) seen 3 days after infection. One CF preparation was viable 6 months following gene transfer.

Figure 3:
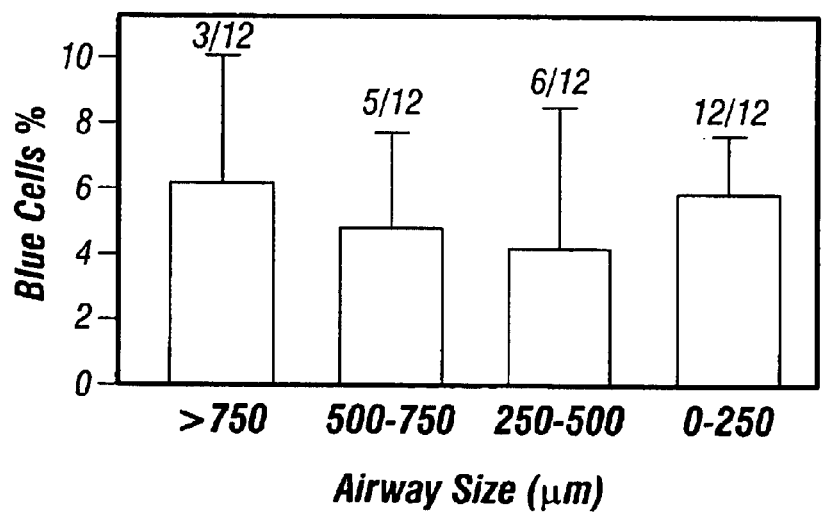

FIG. 3. FIV vector transduction of lower airway epithelia 5 days following gene transfer. Gene transfer is expressed as a function of airway size. The numbers above each bar represent the number of animals with transduced cells in the corresponding region. With the vector administration method used, cells in the smaller airways were more commonly transduced than in the larger airways. Tissues from 12 animals were studied.

FIG. 4A, FIG. 4B, FIG. 4C, and FIG. 4D. The effects of EGTA, EDTA and BAPTA on transepithelial resistance and gene transfer. Well-differentiated airway epithelia were pretreated with 100 ng/ml KGF for 24 hr. Hypotonic (FIG. 4A) or isotonic (FIG. 4B) solutions with 6 mM of the indicated $Ca^{2+}$ chelators were applied to the apical surface. Transepithelial resistance was measured with an ohmmeter and normalized to 100% of control values. For gene transfer studies, 6 mM (final concentration) hypotonic or isotonic EGTA (FIG. 4C) or BAPTA (FIG. 4D) was formulated with the TA-7βgal vector. The incubation times are indicated on the X-axis. The Y-axis shows the percentage of blue cells. Values shown are mean +/− SE (n=3 epithelia/time point; * indicates p<0.05 by t test for the treatment group vs. control at each time point).

Figure 5A:
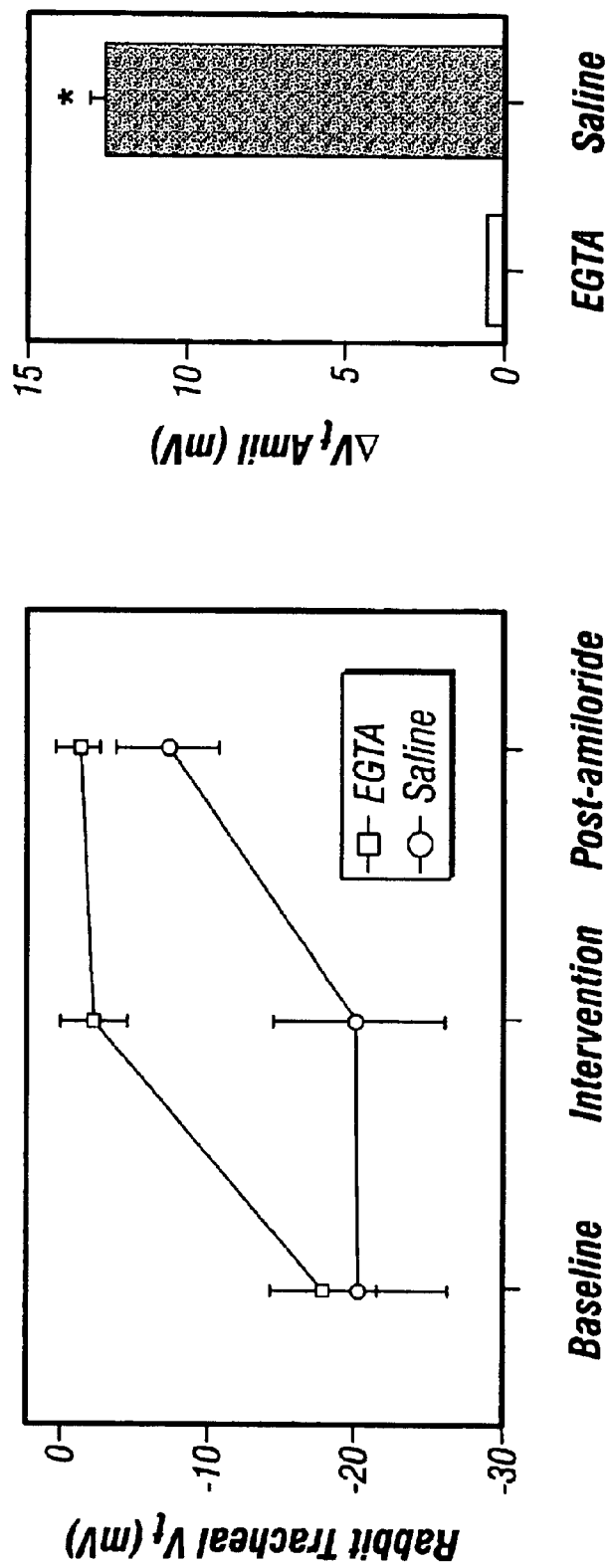
Figure 5B:
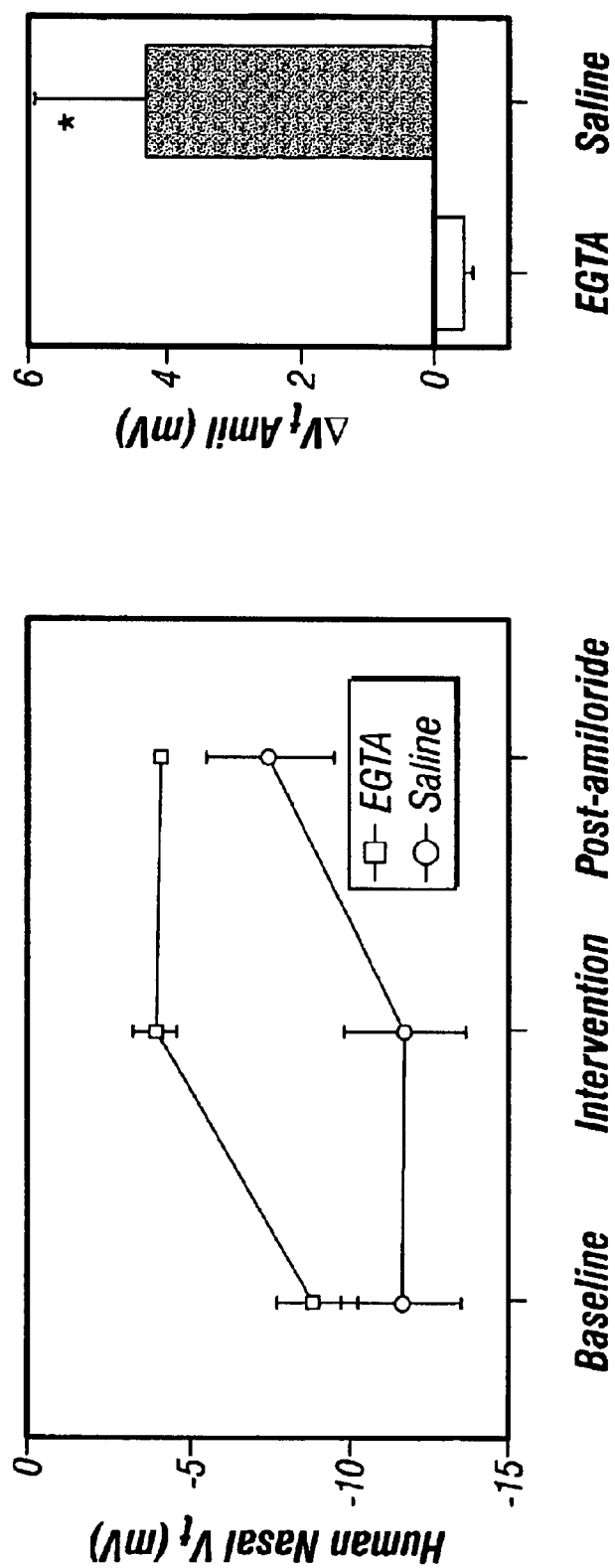

FIG. 5A and FIG. 5B. Perfusion of the rabbit tracheal epithelia and human nasal epithelia with hypotonic EGTA solution inhibits baseline $V_t$ and amiloride sensitive $V_t$ in vivo. FIG. 5A. The tracheal transepithelial voltage was measured in anesthetized rabbits via tracheostomy as described in Methods. Left hand panel: In control animals the baseline voltage remained stable with saline perfulsion. Addition of amiloride caused a significant reduction in $V_t$. Sequential treatment with water perfusion followed by perfusion with 10 mM EGTA in saline ("intervention") caused a reduction in $V_t$. Following EGTA treatment, there was no residual amiloride-sensitive $V_t$. Right hand panel: Comparison of the amiloride-sensitive $V_t$ in control and EGTA treated animals (n=4 rabbits each for EGTA and control conditions, * indicates p<0.05). FIG. 5B. Perfusion of the human nasal respiratory epithelium with hypotonic/EGTA solution inhibits baseline $V_t$ and amiloride sensitive $V_t$. Left hand panel: The nasal epithelium of normal volunteers was sequentially perftised with EGTA in water; EGTA in saline, and then EGTA in saline with amiloride. The nasal transepithelial potential was measured continuously. In control experiments, the same protocol was performed in the same subjects on another day, omitting EGTA from the perfusate. Under EGTA conditions ("intervention"), there was a significant, reversible drop in the $V_t$ and the amiloride-sensitive $V_t$. Right hand panel: Net change in $V_t$ in response to amiloride for control and EGTA treated subjects. EGTA treatment abolished the amiloride-sensitive $V_t$ (n=6 for each condition; * indicates p<0.01).

Figure 6:
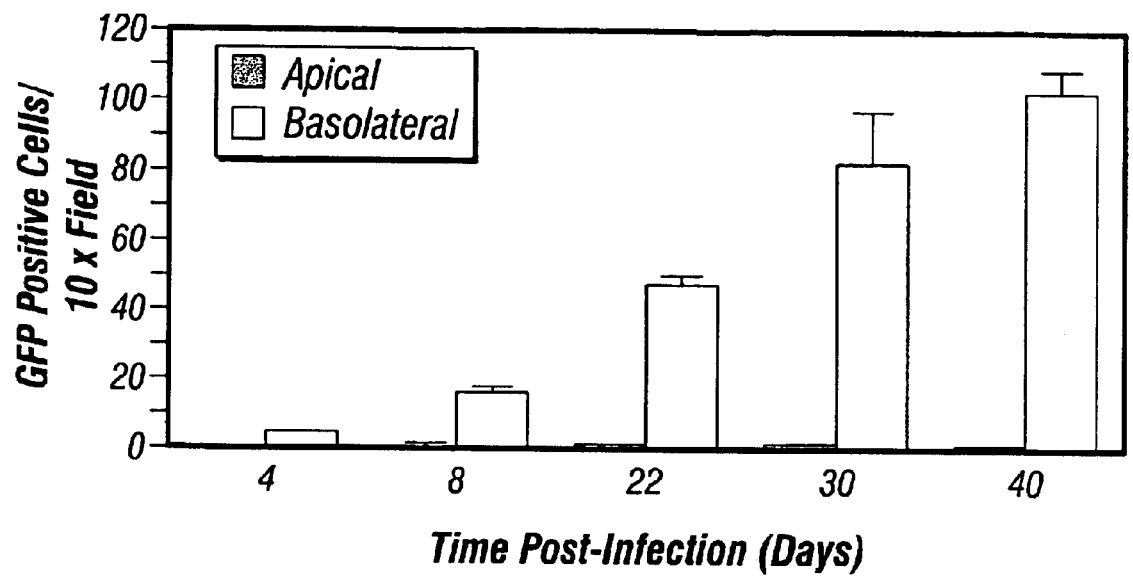

FIG. 6. Polarity and time course of rAAV transduction in differentiated bronchial epithelial cells. Polarized airway epithelia were infected via the apical or basolateral membranes with 5×109 particles of AV.GFP3Ori virus (MOI of 10,000 particles/cell) for 24 hr. The abundance of GFP trarsgene-expressing cells was quantitated by indirect fluorescence microscopy at 4, 8, 22, 30, and 40 days. The bar graphs represent the mean (+SEM) of four dependent experiments for each condition.

Figure 7:
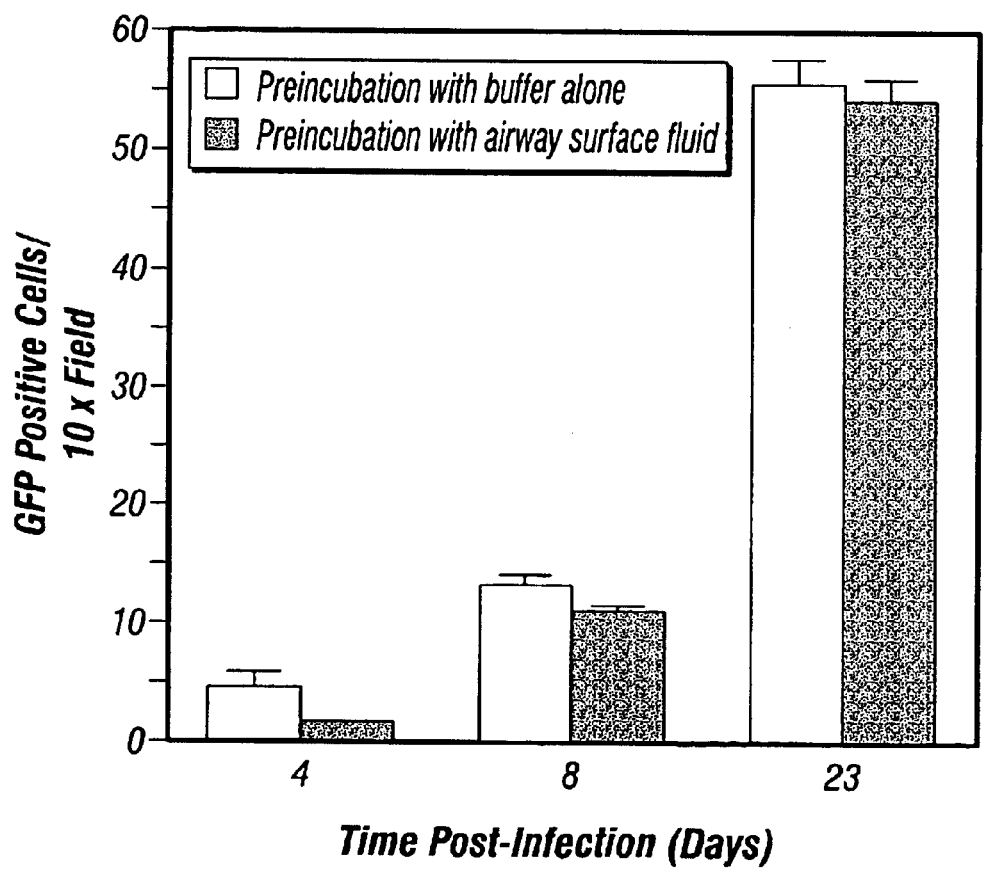

FIG. 7. Airway surface fluid does not affect rAAV transduction in polarized bronchial epithelia. Airway surface secretions from 5-week old, fully differentiated human bronchial xenografts (Zhang et al., 1995) were collected by irrigating the lumen of xenograft airways with 50 μl of HPBR (HEPES phosphate-buffered Ringer's solution, containing 10 mM HEPES, [pH 7.4], 145 mM Nacl, 5 mM KCl, 1.2 mM $MgSO_4$, 1.2 mM calcium gluconate, 2.4 mM $K_2HPO_4$, and 0.4 mM $KH_2PO_4$). Airway surface fluid from three independent xenografts was combined for analyses. Prior to infection, rAAV was uncubated with either an equal volume of HPBR buffer or xenograft airway surface fluid at 37° C. for 4 hr. Transgene expression was examined 4, 8, and 23 days postinfection. The bar represents the mean (±SEM) of three independent studies for each condition.

Figure 8A:
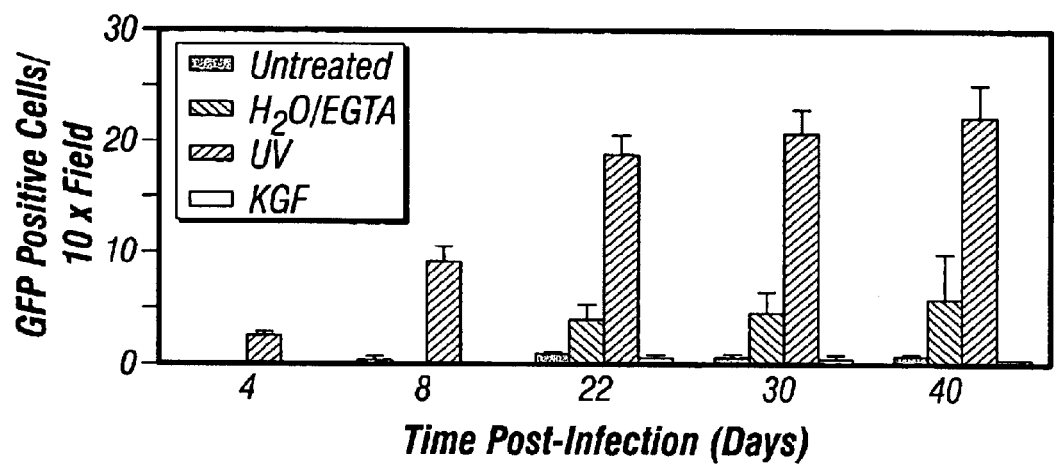
Figure 8B:
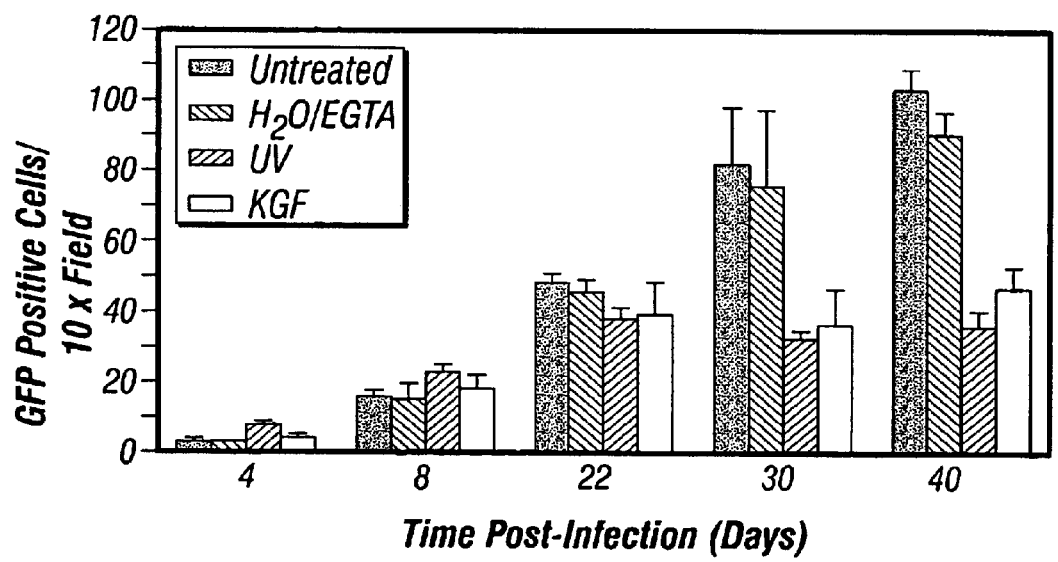

FIG. 8A and FIG. 8B. Modulation of rAAV transduction from the apical and basolateral membrane by environmental stimuli. Polarized airway epithelia were treated with hypotonic EGTA (3 mM), UV (25 J/m$^2$), or KGF (100 ng/ml) as described in Materials and Methods, followed by infection with 5×10$^9$ particles of AV.GFP3ori virus (MOI of 10,000 particles/cell) from the apical (FIG. 8A) or basolateral (FIG. 8B) side of polarized epithelial primary cultures. The abundance of GFP transgene-expressing cells was quantitated by indirect fluorescence microscopy at 4, 8, 22, 30, and 40 days. The bar graphs in (A) and (B) represent the mean (±SEM) of four independent studies for each condition. Transgene expression was compared with matched (identical batch of samples) untreated controls for each experimental condition. The efficiency of rAAV transduction, following apical application of virus. increased 7- to 10-fold after disruption of tight junctions with hypotonic EGTA solution. UV irradiation resulted in a 21- to 30-fold augmentation in rAAV transduction from the apical surface of epithelia.

Figure 9:
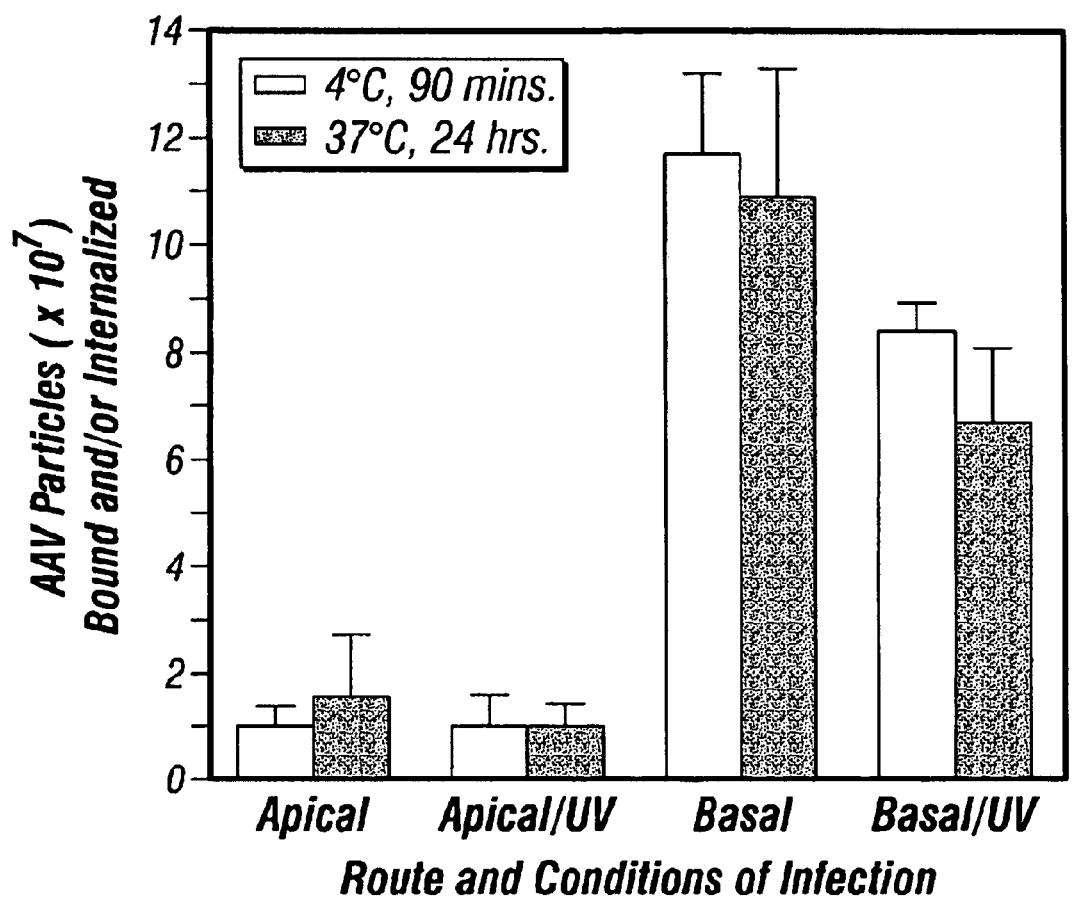

FIG. 9. Uptake of $^3$H-labeled AV.GFP3ori in fully differentiated bronchial epithelium. The ability of polarized bronchial epithelial cultures to bind and internalize virus applied to either the apical or basolateral surfaces was quantified using radiolabeled rAAV ($^3$H-labeled AV.GFP3ori). Two study conditions evaluated either viral binding (4° C. incubation with virus for 90 min) or the total amount of bound and internalized virus over a prolonged incubation period (37° C. incubation with virus for 24 hr). Nonspecific background binding of radiolabeled virus was determined by parallel studies on collagen coated empty chambers that were not seeded with bronchial cells. Background counts were subtracted from study points prior to data analysis. The bar graph represents the net bindinglinternalization of AAV as total particles per well. The results represent the mean (±SEM) of five independent studies for each condition.

DESCRIPTION OF ILLUSTRATIVE EMBODIMENTS

The development of gene therapy methods has long been a goal of medical research. Since 1990, numerous gene therapy trials have been attempted in humans and have shown that gene therapy is a safe and potentially efficacious treatment for genetic disorders. Initially, there were numerous difficulties to overcome in the development of effective gene therapy methods. These difficulties included the identification of the genetic defects responsible for various illnesses, the isolation of functional copies of these genes and the design and delivery of vehicles to transport functional copies of the defective genes into diseased tissues. Currently the genetic defects responsible for or contributing to many illnesses are known and functional copies of the genes have been isolated.

Genetically engineered viruses have been designed that are capable of delivering therapeutic genes to various target tissues. One ongoing difficulty is the efficient delivery of therapeutic genes to target tissues. While some vectors may have high levels of infectivity in vitro, conditions in vivo may be altered such that the vectors have much lower rates of infectivity. For many disease states, it is important that high levels of transgene expression be achieved. Even where highly active promoters are used, and transgene product turnover is low, the inability to infect target cells with high efficiency is highly limiting.

The present invention is designed to overcome these deficiencies by providing methods for increasing the susceptibility of epithelial cells to viral infection comprising increasing the transepithelial permeability of epithelial tissue. Treatment with tissue permeablizing agents such as hypotonic shock or EGTA increases transepithelial permeability and enhances gene transfer by viral vectors applied to the mucosal surface of epithelial tissue. Using this approach, cells throughout the epithelial sheet, including basal cells, are targeted. It was shown that, using this approach, it was possible to correct the Cl⁻ transport defect in differentiated CF airway epithelia in vitro.

An additional enhancement of gene transfer efficiency in the invention can be achieved by stimulating division of epithelial cells by increasing the proliferation of said epithelial cells by contacting the cells with a cell proliferative factor. Recent studies by the inventors and by others have identified epithelial specific growth factors which stimulate proliferation in vivo without prior injury. Keratinocyte growth factor (KGF) stimulates proliferation of epithelia in multiple organs including the bronchial and alveolar cells of the lung (Ulich, et al., 1994; Housley et al., 1994). Hepatocyte growth factor (HGF) also is a potent in vivo mitogen for proliferation in pulmonary epithelia (Mason et al., 1994; Ohmichi et al., 1996). In vivo, KGF appears to stimulate only 1 to 2 cycles of cell division and is not mutagenic (Ulich, et al., 1994; Housley et al., 1994). The inventors' in vivo data shows that KGF and HGF stimulate epithelial proliferation in the lungs and liver of rodents (Bosch et al., 1996; Bosch et al., 1998, Wang et al., 1998 and 1999).

A. Target Tissues

The present invention is designed to increase the susceptibility of epithelial cells to viral infection. Epithelial tissue includes skin, the lining of the gastrointestinal tract and the lining of the airway and lungs. The airway and lungs include the nasal passages, the oral cavity, the upper part of the pharynx (throat), the larynx (voice box), the trachea (windpipe), bronchi, bronchioles, and other epithelia including uroepithelium of the kidneys and bladder, mammary epithelia, lining of brain ventricles, leptomenengis, and the alveoli of the lungs.

B. Therapeutic Genes and Disease States

Gene therapy has become an increasingly viable endeavor in the past decade because for the mere reason that genetic defects responsible for numerous genetic diseases have been identified. Such genes include cytokines, hormones, transporters, enzymes and receptors. Examples include the genes responsible for cystic fibrosis (CF), surfactant protein B deficiency and alpha-1-antitrypsin deficiency. Additionally, various antisense oncogene constructs, tumor suppressor genes, inducers of apoptosis, repair genes and toxins have been identified as potential therapeutics in various cancers. A list of potential therapeutic genes is set forth below.

I. Tumor Suppressors p53 currently is recognized as a tumor suppressor gene. High levels of mutant p53 have been found in many cells transformed by chemical carcinogenesis, ultraviolet radiation, and several viruses. The p53 gene is a frequent target of mutational inactivation in a wide variety of human tumors and is already documented to be the most frequently-mutated gene in common human cancers. It is mutated in over 50% of human NSCLC (Hollstein et al., 1991) and in a wide spectrum of other tumors.

The p53 gene encodes a 393-amino acid phosphoprotein that can form complexes with host proteins such as SV40 large-T antigen and adenoviral E1B. The protein is found in normal tissues and cells, but at concentrations which are minute by comparison with transformed cells or tumor tissue. Interestingly, wild-type p53 appears to be important in regulating cell growth and division. Overexpression of wild-type p53 has been shown in some cases to be anti-proliferative in human tumor cell lines. Thus, p53 can act as a negative regulator of cell growth (Weinberg, 1991) and may directly suppress uncontrolled cell growth or indirectly activate genes that suppress this growth. Thus, absence or inactivation of wild-type p53 may contribute to transformation. However, some studies indicate that the presence of mutant p53 may be necessary for full expression of the transforming potential of the gene.

Wild-type p53 is recognized as an important growth regulator in many cell types. Missense mutations are common for the p53 gene and are essential for the transforming ability of the oncogene. A single genetic change prompted by point mutations can create carcinogenic p53, in as much as mutations in p53 are known to abrogate the tumor suppressor capability of wild-type p53. Unlike other oncogenes, however, p53 point mutations are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Casey and colleagues have reported that transfection of DNA encoding wild-type p53 into two human breast cancer cell lines restores growth suppression control in such cells (Casey et al., 1991). A similar effect has also been demonstrated on transfection of wild-type, but not mutant, p53 into human lung cancer cell lines (Takahasi et al., 1992). p53 appears dominant over the mutant gene and will select against proliferation when transfected into cells with the mutant gene. Normal expression of the transfected p53 does not affect the growth of normal or non-malignant cells with endogenous p53. Thus, such constructs might be taken up by normal cells without adverse effects. It is thus proposed that the treatment of p53-associated cancers with wild-type p53 will reduce the number of malignant cells or their growth rate.

The major transitions of the eukaryotic cell cycle are triggered by cyclin-dependent kinases, or CDK's. One CDK, cyclin-dependent kinase 4 (CDK4), regulates progression through the $G_1$. The activity of this enzyme may be to phosphorylate Rb at late $G_1$. The activity of CDK4 is controlled by an activating subunit, D-type cyclin, and by an inhibitory subunit p16$^{INK4}$. The p16$^{INK4}$ has been biochemically characterized as a protein that specifically binds to and inhibits CDK4, and thus may regulate Rb phosphorylation (Serrano et al., 1993; Serrano et al., 1995). Since the p16$^{INK4}$ protein is a CDK4 inhibitor (Serrano, 1993), deletion of this gene may increase the activity of CDK4, resulting in hyperphosphorylation of the Rb protein. p16 also is known to regulate the function of CDK6.

$p16^{INK4}$ belongs to a newly described class of CDK-inhibitory proteins that also includes $p15^{INK4B}$, $p21^{WAF1}$, and $p27^{KIP1}$. The $p16^{INK4}$ gene maps to 9p21, a chromosome region frequently deleted in many tumor types. Homozygous deletions and mutations of the $p16^{INK4}$ gene are frequent in human tumor cell lines. This evidence suggests that the $p16^{INK4}$ gene is a tumor suppressor gene. This interpretation has been challenged, however, by the observation that the frequency of the $p16^{INK4}$ gene alterations is much lower in primary uncultured tumors than in cultured cell lines (Caldas et al., 1994; Cheng et al., 1994; Hussussian et al., 1994; Kamb et al., 1994; Kamb et al., 1994; Mori et al., 1994; Okamoto et al., 1994; Nobori et al., 1995; Orlow et al., 1994; Arap et al., 1995). However, it was later shown that while the p16 gene was intact in many primary tumors, there were other mechanisms that prevented p16 protein expression in a large percentage of some tumor types. p16 promoter hypermethylation is one of these mechanisms (Merlo et al., 1995; Herman, 1995; Gonzalez-Zulueta, 1995). Restoration of wild-type $p16^{INK4}$ function by transfection with a plasmid expression vector reduced colony formation by some human cancer cell lines (Okamoto, 1994; Arap, 1995). Delivery of p16 with adenovirus vectors inhibits production of some human cancer lines and reduces the growth of human tumor xenografts C-CAM is expressed in virtually all epithelial cells (Odin and Obrink, 1987). C-CAM, with an apparent molecular weight of 105 kD, was originally isolated from the plasma membrane of the rat hepatocyte by its reaction with specific antibodies that neutralize cell aggregation (Obrink, 1991). Recent studies indicate that, structurally, C-CAM belongs to the immunoglobulin (Ig) superfamily and its sequence is highly homologous to carcinoembryonic antigen (CEA) (Lin and Guidotti, 1989). Using a baculovirus expression system, Cheung et al., (1993) demonstrated that the first Ig domain of C-CAM is critical for cell adhesive activity.

Cell adhesion molecules, or CAM's are known to be involved in a complex network of molecular interactions that regulate organ development and cell differentiation (Edelman, 1985). Recent data indicate that aberrant expression of CAM's maybe involved in the tumorigenesis of several neoplasms; for example, decreased expression of E-cadherin, which is predominantly expressed in epithelial cells, is associated with the progression of several kinds of neoplasms (Edelman and Crossin, 1991; Frixen et al., 1991; Bussemakers et al., 1992; Matsura et al., 1992; Umbas et al., 1992). Also, Giancotti and Ruoslahti (1990) demonstrated that increasing expression of $\alpha_5\beta_1$ integrin by gene transfer can reduce tumorigenicity of Chinese hamster ovary cells in vivo. C-CAM now has been shown to suppress tumor growth in vitro and in vivo.

Other tumor suppressors that may be employed according to the present invention include p21, p15, BRCA1, BRCA2, IRF-1, PTEN, RB, APC, DCC, NF-1, NF-2, WT-1, MEN-I, MEN-II, zac1, p73, VHL, FCC and MCC.

II. Inducers of Apoptosis

Inducers of apoptosis, such as Bax, Bak, Bcl-X$_S$, Bad, Bim, Bik, Bid, Harakiri, Ad E1B, Bad and ICE-CED3 proteases, similarly could find use according to the present invention, particularly in the treatment of cancers.

III. Enzymes

Various enzyme genes are of interest according to the present invention. Such enzymes include human copper zinc superoxide dismutase (U.S. Pat. No. 5,196,335), cytosine deaminase, adenosine deaminase, hypoxanthine-guanine phosphoribosyltransferase, galactose-1-phosphate uridyltransferase, phenylalanine hydroxylase, glucocerbrosidase, sphingomyelinase, α-L-iduronidase, glucose-6-phosphate dehydrogenase, β-glucuronidase, HSV thymidine kinase and human thyridine kinase and extracellular proteins such as collagenase and matrix metalloprotease.

IV. Cytokines

Another class of genes that is contemplated to be inserted into the retroviral vectors of the present invention include interleukins and cytokines. Interleukin 1 (IL-1), IL-2, IL-3, IL-4, IL-5, IL-6, IL-7, IL-8, IL-9, IL-10, IL-11, IL-12, IL-13, IL-14, IL-15, β-interferon, α-interferon, γ-interferon, angiostatin, thrombospondin, endostatin, METH-1, METH-2, GM-CSF, G-CSF, M-CSF and tumor necrosis factor.

V. Toxins

Various toxins are also contemplated to be useful as part of the expression vectors of the present invention, these toxins include bacterial toxins such as ricin A-chain (Burbage, 1997), diphtheria toxin A (Massuda et al., 1997; Lidor, 1997), pertussis toxin A subunit, E. coli enterotoxin toxin A subunit, cholera toxin A subunit and Pseudomonas toxin C-terminal. Recently, it was demonstrated that transfection of a plasmid containing the fusion protein regulatable diphtheria toxin A chain gene was cytotoxic for cancer cells. Thus, gene transfer of regulated toxin genes might also be applied to the treatment of cancers (Massuda et al., 1997).

VI. Antisense Constructs

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing. As part of the present invention, particular interest will be paid to the delivery of antisense oncogenes. Particular oncogenes that are targets for antisense constructs are ras, myc, neu, raf, erb, src, fms, jun, trk ret, hst, gsp, bcl-2 and abl.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50–200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

VII. Ribozymes

Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cook, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cook et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cook et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme. Targets for this embodiment will include angiogenic genes such as VEGFs and angiopoeiteins as well as the oncogenes (e.g., ras, myc, neu, raf, erb, src, fms, jun, trk, ret, hst, gsp, bcl-2, EGFR, grb2 and abl. Other constructs will include overexpression of antiapoptotic genes such as bcl-2.

VIII. Single Chain Antibodies

In yet another embodiment, one gene may comprise a single-chain antibody. Methods for the production of single-chain antibodies are well known to those of skill in the art. The skilled artisan is referred to U.S. Pat. No. 5,359,046, (incorporated herein by reference) for such methods. A single chain antibody is created by fusing together the variable domains of the heavy and light chains using a short peptide linker, thereby reconstituting an antigen binding site on a single molecule.

Single-chain antibody variable fragments (scFvs) in which the C-terminus of one variable domain is tethered to the N-terminus of the other via a 15 to 25 amino acid peptide or linker, have been developed without significantly disrupting antigen binding or specificity of the binding (Bedzyk et al., 1990; Chaudhary et al., 1990). These Fvs lack the constant regions (Fc) present in the heavy and light chains of the native antibody.

Antibodies to a wide variety of molecules are contemplated, such as oncogenes, growth factors, hormones, enzymes, transcription factors or receptors. Also contemplated are secreted antibodies, targeted to serum, against angiogenic factors (VEGF/VSP; βFGF; αFGF) and endothelial antigens necessary for angiogenesis (i.e. V3 integrin). Specifically contemplated are growth factors such as transforming growth factor and platelet derived growth factor.

IX. Transcription Factors and Regulators

Another class of genes that can be applied in an advantageous combination are trascription factors. Examples include C/EBPα, IκB, NfκB and Par4.

X. Cell Cycle Regulators

Cell cycle regulators provide possible advantages, when combined with other genes. Such cell cycle regulators include p27, p16, p21, p57, p18, p73, p19, p15, E2F1, E2F-2, E2F-3, p107, p130 and E2F-4. Other cell cycle regulators include anti-angiogenic proteins, such as soluble Flt1 (dominant negative soluble VEGF receptor), soluble Wnt receptors, soluble Tie2/Tek receptor, soluble hemopexin domain of matrix metalloprotease 2 and soluble receptors of other angiogenic cytokines (e.g., VEGFR1/KDR, VEGFR3/Flt4, both VEGF receptors).

XI. Chemokines

Genes that code for chemokines also may be used in the present invention. Chemokines generally act as chemoattractants to recruit immune effector cells to the site of chemokine expression. It may be advantageous to express a particular chemokine gene in combination with, for example, a cytokine gene, to enhance the recruitment of other immune system components to the site of treatment. Such chemokines include RANTES, MCAF, MIP1-alpha, MIP1-Beta, and IP-10. The skilled artisan will recognize that certain cytokines are also known to have chemoattractant effects and could also be classified under the term chemokines.

XII. Combination Therapy

As described herein, it is contemplated that any one particular gene may be combined with any other particular gene in the form of a combined therapy. Other combinations include the use of a particular therapeutic gene with a more traditional pharmaceutical therapy, such as the combination of a tumor suppressor gene with chemo- or radiotherapy. For example, the herpes simplex-thymidine kinase (HS-tk) gene, when delivered to brain tumors by a retroviral vector system, successfully induced susceptibility to the antiviral agent ganciclovir (Culver et al., 1992). In the context of the present invention, it is contemplated that gene therapy to induce a therapeutic effect in for example a cancer cell could be used similarly in conjunction with chemo- or radiotherapeutic intervention. It also may prove effective to combine a particular gene therapy with immunotherapy.

In a cancer phenotype to kill cells, inhibit cell growth, inhibit metastasis, inhibit angiogenesis or otherwise reverse or reduce the malignant phenotype of tumor cells, using the methods and compositions of the present invention, one would generally contact a "target" cell with an expression construct containing a particular gene. In CF it is contemplated that the CFTR gene is delivered and caused and achieves a correction, of $Cl^{31}$ transport or an amelioration of the detrimental effects of loss of $Cl^{31}$ transport seen in CF.

As stated above, a gene therapy may be administered alone or in combination with at least one other agent. These compositions would be provided in a combined amount effective to kill or inhibit proliferation of a cancer cell or restore $Cl^-$ transport function in CF. This process may involve contacting the cells with the expression construct and the agent(s) or factor(s) at the same time. This may be achieved by contacting the cell with a single composition or pharmacological formulation that includes both agents, or by contacting the cell with two distinct compositions or formulations, at the same time, wherein one composition includes the expression construct and the other includes the agent.

Alternatively, the gene therapy treatment may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one would contact the cell with both modalities within about 12–24 hours of each other and, more preferably, within about 6–12 hours of each other, with a delay time of only about 12 hours being most preferred. In some situations, it may be desirable to extend the time period for treatment significantly, however, where several days (2, 3, 4, 5, 6 or 7) to several wk (1, 2, 3, 4, 5, 6, 7 or 8) lapse between the respective administrations.

It also is conceivable that more than one adnministration of either the gene therapy or the other agent will be desired. Various combinations may be employed, where the primary gene therapy (e.g. CFTR in CF) is "A" and the other agent is "B", as exemplified below:

A/B/A B/A/B B/B/A A/A/B B/A/A A/B/B B/B/B/A B/B/A/B

A/A/B/B A/B/A/B A/B/B/A B/B/A/B B/A/B/A B/A/A/B B/B/B/A

A/A/A/B B/A/A/A A/B/A/A A/A/B/A A/B/B/B B/A/B/B B/B/A/B

Other combinations are contemplated. Again, to achieve a therapeutic outcome, both agents are delivered to a cell in a combined amount effective to restore a normal state in the cell.

In a cancer therapy, agents or factors suitable for use in a combined therapy are any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic agents," function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CDDP) and even hydrogen peroxide. The invention also encompasses the use of a combination of one or more DNA damaging agents, whether radiation-based or actual compounds, such as the use of X-rays with cisplatin or the use of cisplatin with etoposide.

In treating cancer according to the invention, one would contact the tumor cells with an agent in addition to the expression construct. This may be achieved by irradiating the localized tumor site with radiation such as X-rays, UV-light, γ-rays or even microwaves. Alternatively, the tumor cells may be contacted with the agent by administering to the subject a therapeutically effective amount of a pharmaceutical composition comprising a compound such as, adriamycin, 5-fluorouracil, etoposide, camptothecin, actinomycin-D, mitomycin C, or more preferably, cisplatin. The agent may be prepared and used as a combined therapeutic composition, or kit, by combining it with an expression construct, as described above.

Agents that directly cross-link nucleic acids, specifically DNA, are envisaged to facilitate DNA damage leading to a synergistic, antineoplastic combination with the gene therapy. Agents such as cisplatin, and other DNA alkylating agents may be used. Cisplatin has been widely used to treat cancer, with efficacious doses used in clinical applications of 20 $mg/m^2$ for 5 days every three wk for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25–75 $mg/m^2$ at 21 day intervals for adriamycin, to 35–50 $mg/m^2$ for etoposide intravenously or double the intravenous dose orally.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, X-rays, and/or the directed delivery of radioisotopes to tumor cells. Other forms of DNA damaging factors also are contemplated such as microwaves and UV-irradiation. It is most likely that all of these factors effect a broad range of damage DNA, on the precursors of DNA, the replication and repair of DNA, and the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624–652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The inventors propose that the regional delivery of genetic expression constructs to patients will be a very efficient method for delivering a therapeutically effective gene to counteract a clinical disease. Similarly, the chemo- or radiotherapy may be directed to a particular, affected region of the subjects body. Alternatively, systemic delivery of expression construct and/or the agent may be appropriate in certain circumstances, for example, where extensive metastasis has occurred.

In addition to combining specific gene therapies with chemo- and radiotherapies, it also is contemplated that combination with other gene therapies will be advantageous. For example, targeting of p53 and p16 mutations at the same time may produce an improved anti-cancer treatment. Any other tumor-related gene conceivably can be targeted in this manner, for example, p21, Rb, APC, DCC, NF-1, NF-2, BCRA2, p16, FHIT, WT-1, MEN-I, MEN-II, BRCA1, VHL, FCC, MCC, ras, myc, neu, raf, erb, src, fms, jun, trk, ret, gsp, hst, bcl and abl.

It also should be pointed out that any of the foregoing therapies may prove useful by themselves in treating a genetic abnormality. In this regard, reference to chemotherapeutics and non-gene therapy in combination should also be read as a contemplation that these approaches may be employed separately.

XIII. Disease States

Particular disease states that could be treated through gene replacement in epithelial cells include lung cancer, tracheal cancer, asthma, surfactant protein B deficiency, alpha-1-antitrypsin deficiency, breast cancer, bladder cancer and cystic fibrosis.

C. Viral and Non-viral Vectors

One aspect of the present invention is a virus that has been genetically engineered to deliver a therapeutic gene sequence to epithelial cells. These genetically engineered viruses are also referred to as viral vectors. Having identified and isolated functional forms of the defective genes responsible for various illnesses, gene therapy protocols require a means of delivering the functional gene to the diseased tissue. Researchers noted that viruses have evolved to be able to deliver their DNA to various host tissues despite the human body's various defensive mechanisms. For this reason, numerous viral vectors have been designed by researchers seeking to create vehicles for therapeutic gene delivery. Some of the types of viruses that have been engineered to create viral vectors for gene therapy are listed below.

I. Adenovirus

Knowledge of the genetic organization or adenovirus, a 36 kB, linear, double-strained DNA virus, allows substitution of large pieces of adenoviral DNA with foreign sequences up to 7 kB (Grunhaus and Horwitz, 1992). In contrast to retrovirus, the infection of adenovira DNA in host cells does not result in chromosomal integration because adenoviral DNA can replicate in an episomal manner. Also, adenoviruses are structurally stable, and no genome rearrangement has been detected after extensive amplification. Adenovirus can infect virtually all epithelial cells regardless of their cell cycle stage. This means that adenovirus can infect non-dividing cells. So far, adenoviral infection appears to be linked only to mild disease such as acute respiratory disease in humans. This group of viruses can be obtained in high titers, e.g., $10^9$–$10^{11}$ plaque-forming units per ml, and they are highly infective.

Adenovirus have been used in eukaryotic gene expression (Levrero et al., 1991; Gomez-Foix et al., 1992) and vaccine development (Grunhaus and Horwitz, 1992; Graham and Prevec, 1992). Animal studies have suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include tracheal instillation (Rosenfeld et al., 1991; Rosenfeld et al., 1992), muscle injection (Ragot et al., 1993), peripheral intravenous injections (Herz and Gerard, 1993) and stereoctatic inoculation into the brain (Le Gal La Salle et al., 1993). Recently, phase I gene therapy clinical trials have begun in human volunteers where adenoviral vectors have been administered by intradermal injection and by intrabronchial infusion to determine what kind of immunological response the vectors elicit (Anderson, 1998).

II. Retroviruses

Particularly in the treatment of chronic illnesses, it may be preferable to use DNA expression vectors which will remain present in the treated tissue for long periods of time negating the need for frequent readministration of the gene therapy. One way of achieving this is through the use of integrating viral vectors. These viruses result in integration of the tansgene in the host genome. The prototypical integrative virus is the retrovirus.

The retroviruses are a group of single-stranded RNA viruses characterized by an ability to convert their RNA to double-stranded DNA to infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene, termed $\psi$, constitutes the packaging signal for the virus. When a recombinant plasmid containing a human cDNA, together with the retroviral LTR and $\psi$ sequences is introduced into this cell line (by calcium phosphate precipitation for example), the $\psi$ sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration with MMLV-based retrovirus requires the division of host cells (Paskind et al., 1975).

The retrovirus family includes the subfamilies of the oncoviruses, the lentiviruses and the spumaviruses. Two oncoviruses are Moloney murine leukemia virus (MMLV) and feline leukemia virus (FeLV). The lentiviruses include human immunodeficiency virus (HIV), simian immunodeficiency virus (SIV) and feline immunodeficiency virus (FIV). Among the murine viruses such as MMLV there is a further classification. Murine viruses may be ecotropic, xenotropic, polytropic or amphotropic. Each class of viruses target different cell surface receptors in order to initiate infection.

MMLV-based retroviruses have received extensive use in gene transfer studies and are approved for human trials. Further advances in retroviral vector design and concentration methods have allowed production of amphotropic and xenotropic viruses with titers of $10^8$ to $10^9$ cfu/ml (Bowles et al., 1996; Irwin et al., 1994; Jolly, 1994; Kitten et al., 1997).

One concern with the use of defective retrovirus vectors is the potential appearance of wild-type replication-competent virus in the packaging cells. This can result from recombination events in which the intact ψ sequence from the recombinant virus inserts upstream from the gag, pol, env sequence integrated in the host cell genome. However, packaging cell lines are now available that should greatly decrease the likelihood of recombination (Markowitz et al., 1988; Hersdorffer et al., 1990). Another concern about retrovirus vectors is that they usually integrate into random sites in the cell genome. Theoretically, this can lead to insertional mutagenesis through the interruption of host genes or through the insertion of viral regulatory sequences that can interfere with the function of flanking genes (Varmus et al., 1981). However, to date, the only example of retroviral gene transfer producing cancer in large animals was found to be due to the integration of contaminant replication-competent virus and not due to the retroviral vectors themselves (Donahue et al., 1992; Anderson, 1998)

Two strategies have been proposed to increase the efficacy of retroviral vectors. First, one can pseudotype the virus and replace the envelope or to make an envelope chimera by adding a novel ligand. The second approach replaces a portion of the normal env protein with a novel ligand that will interact with a more abundant cell membrane receptor or component. Successful examples include pseudotyping with the vesicular stomatitis G protein (VSV-G, (Burns et al., 1993)), and envelope chimeras containing hereguliin (Han et al., 1995) and erythropoetin (Kasahara et al., 1994). The receptor for VSV-G has not been cloned but is believed to be a phosphoserine component of the plasma membrane (Schlegel et al., 1983).

MMLV-based retroviruses have received extensive use in gene transfer studies, primarily using ex vivo approaches, and have been approved for several human trials. Replication defective recombinant retroviruses are not acute pathogens in primates (Chowdhury et al., 1991). They have been successfully applied in cell culture systems to transfer the CFTR gene and generate cAMP-activated $Cl^{31}$ secretion in a variety of cell types including human airway epithelia (Drumm et al., 1990, Olsen et al., 1992; Anderson et al., 1991; Olsen et al., 1993). While there is evidence of immune responses to the viral gag and env proteins, this does not prevent successful readministration of vector (McCormack et al., 1997). Further, since recombinant retroviruses have no expressed gene products other than the transgene, the risk of a host inflammatory response due to viral protein expression is limited (McCormack et al., 1997). As for the concern about insertional mutagenesis, to date there are no examples of insertional mutagenesis arising from any human trial with recombinant retroviral vectors.

Until recently, one limitation to the use of retrovirus vectors in vivo was the limited ability to produce retroviral vector titers greater than $10^6$ infections U/mL. Titers 10- to 1,000-fold higher are necessary for many in vivo applications. Important advances in viral constructs and concentration methods have been made by Dr. Doug Jolly and colleagues at Chiron Technologies Center for Gene Therapy, resulting in titers of ampho- and xenotropic viruses in the $10^8$ to $10^9$ cfu/ml range (Jolly, 1994; Irwin et al., 1994). Similar results have also been reported by Woo et al., (Bowles et al., 1996) and Ferry and colleagues (Kitten et al., 1997).

More recently, hybrid lentivirus vectors have been described combining elements of human immunodeficiency virus (HIV) (Naldini et al., 1996) or feline immunodeficiency virus (FIV) (Poescha et al., 1998) and MMLV. These vectors transduce nondividing cells in the CNS (Naldini et al., 1996; Blomer et al., 1997), liver (Kafri et al., 1997), muscle (Kafri et al., 1997) and retina (Miyoshi et al., 1997). However, a recent report in xenograft models of human airway epithelia suggests that in well-differentiated epithelia, gene transfer with VSV-G pseudotyped HIV-based lentivirus is inefficient (Goldman et al., 1997).

A recent report by Wilson and colleagues observed that primary cultures of dividing human airway epithelia expressed more transgene when infected with lentivirus than confluent epithelia (Goldman et al., 1997). This leads to the conclusion that HIV-based lentivirus can infect non-dividing, well-differentiated airway epithelia. Several other recent studies confirm that hybrid lentiviral vectors infect nondividing mammalian cells (Naldine et al., 1996, Kafri et al., 1997).

III. Adeno-associated Virus

Recently, adeno-associated virus (AAV) has emerged as a potential alternative to the more commonly used retroviral and adenoviral vectors. While studies with retroviral and adenoviral mediated gene transfer raise concerns over potential oncogenic properties of the former, and immunogenic problems associated with the latter, AAV has not been associated with any such pathological indications. This may be due to the fact that AAV appears to integrate preferentially into the short arm of human chromosome 19 (Anderson, 1998). AAV vectors have been shown to transduce brain, skeletal muscle and liver cells efficiently and may be capable of infecting non-dividing cells (Anderson, 1998). The sequence of AAV is provided by Srivastava et al., (1983). AAV is a member of the parvovirus family which includes the genus parvovirus and the genus dependovirus. AAV is classified as a dependovirus (Murphy and Kingsbury, 1991). The use of AAV in gene transfer is described in U.S. Pat. No. 5,139,941 and 5,252,479 (specifically incorporated herein by reference).

IV. Vaccinia Virus

Vaccinia viruses are a genus of the poxvirus family. Vaccinia virus vectors have been used extensively because of the ease of their construction, relatively high levels of expression obtained, wide host range and large capacity for carrying DNA. Vaccinia contains a linear, double-stranded DNA genome of about 186 kB that exhibits a marked "A–T" preference. Inverted terminal repeats of about 10.5 kB flank the genome. The majority of essential genes appear to map within the central region, which is most highly conserved among poxviruses. Estimated open reading frames in vaccinia virus number from 150 to 200. Although both strands are coding, extensive overlap of reading frames is not common. U.S. Pat. No. 5,656,465 (specifically incorporated by reference) describes in vivo gene delivery using pox viruses.

V. Papovavirus

The papovavirus family includes the papillomaviruses and the polyomaviruses. The polyomaviruses include Simian Virus 40 (SV40), polyoma virus and the human polyomaviruses BKV and JCV. Papilloma viruses include the bovine and human papillomaviruses. The genomes of polyomaviruses are circular DNAs of a little more than 5000 bases. The predominant gene products are three virion proteins (VP1–3) and Large T and Small T antigens. Some have an additional structural protein, the agnoprotein, and others have a Middle T antigen. Papillomaviruses are somewhat larger, approaching 8 kB.

Little is known about the cellular receptors for polyomaviruses, but polyoma infection can be blocked by treating with sialidase. SV40 will still infect sialidase-treated cells, but JCV cannot hemagglutinate cells treated with sialidase. Because interaction of polyoma VP1 with the cell surface activates c-myc and c-fos, it has been hypothesized that the virus receptor may have some properties of a growth factor receptor. Papillomaviruses are specifically tropic for squamous epithelia, though the specific receptor has not been identified.

VI. Paramyxovirus

The paramyxovirus family is divided into three genera: paramyxovirus, morbillivirus and pneumovirus. The paramyxovirus genus includes the mumps virus and Sendai virus, among others, while the morbilliviruses include the measles virus and the pneumoviruses include respiratory syncytial virus (RSV). Paramyxovirus genomes are RNA based and contain a set of six or more genes, covalently linked in tandem. The genome is something over 15 kB in length. The viral particle is 150–250 nm in diameter, with "fuzzy" projections or spikes protruding therefrom. These are viral glycoproteins that help mediate attachment and entry of the virus into host cells.

VII. Non-Viral Vectors

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al., (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al., (1980) demonstrated the feasibility of liposome-mediated delivery and expression of foreign DNA in cultured chick embryo, HeLa and hepatoma cells. Nicolau et al., (1987) accomplished successfuil liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al., (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type such as lung, epithelial or tumor cells, by any number of receptor-ligand systems with or without liposomes. For example, epidermal growth factor (EGF) may be used as the receptor for mediated delivery of a nucleic acid encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

D. Regulatory Elememts

I. Promoters

Throughout this application, the term "expression construct" is meant to include any type of genetic construct containing a nucleic acid coding for gene products in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding genes of interest.

The nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules and other sequences that initiate transcription. Exemplary are those sequences clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, β-actin, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized.

Selection of a promoter that is regulated in response to specific physiologic or synthetic signals can permit inducible expression of the gene product. For example in the case where expression of a transgene, or transgenes when a multicistronic vector is utilized, is toxic to the cells in which the vector is produced in, it may be desirable to prohibit or reduce expression of one or more of the transgenes. Examples of transgenes that may be toxic to the producer cell line are pro-apoptotic and cytokine genes. Several inducible promoter systems are available for production of viral vectors where the transgene product may be toxic.

The ecdysone system (Invitrogen, Carlsbad, Calif.) is one such system. This system is designed to allow regulated expression of a gene of interest in mammalian cells. It consists of a tightly regulated expression mechanism that allows virtually no basal level expression of the transgene, but over 200-fold inducibility. The system is based on the heterodimeric ecdysone receptor of Drosophila, and when ecdysone or an analog such as muristerone A binds to the receptor, the receptor activates a promoter to turn on expression of the downstream transgene high levels of mRNA transcripts are attained. In this system, both monomers of the heterodimeric receptor are constitutively expressed from one vector, whereas the ecdysone-responsive promoter which drives expression of the gene of interest is on another plasmid. Engineering of this type of system into the gene transfer vector of interest would therefore be useful. Cotransfection of plasmids containing the gene of interest and the receptor monomers in the producer cell line would then allow for the production of the gene transfer vector without expression of a potentially toxic transgene. At the appropriate time, expression of the transgene could be activated with ecdysone or muristeron A.

Another inducible system that would be useful is the Tet-Off™ or Tet-On™ system (Clontech, Palo Alto, Calif.) originally developed by Gossen and Bujard (Gossen and Bujard, 1992; Gossen et al., 1995). This system also allows high levels of gene expression to be regulated in response to tetracycline or tetracycline derivatives such as doxycycline. In the Tet-On™ system, gene expression is turned on in the presence of doxycycline, whereas in the Tet-Off™ system, gene expression is turned on in the absence of doxycycline. These systems are based on two regulatory elements derived from the tetracycline resistance operon of E. coli. The tetracycline operator sequence to which the tetracycline repressor binds, and the tetracycline repressor protein. The gene of interest is cloned into a plasmid behind a promoter that has tetracycline-responsive elements present in it. A second plasmid contains a regulatory element called the tetracycline-controlled tansactivator, which is composed, in the Tet-Off™ system, of the VP16 domain from the herpes simplex virus and the wild-type tertracycline repressor. Thus in the absence of doxycycline, transcription is constitutively on. In the Tet-On™ system, the tetracycline repressor is not wild type and in the presence of doxycycline activates transcription. For gene therapy vector production, the Tet-Off™ system would be preferable so that the producer cells could be grown in the presence of tetracycline or doxycycline and prevent expression of a potentially toxic transgene, but when the vector is introduced to the patient, the gene expression would be constitutively on.

In some circumstances, it may be desirable to regulate expression of a transgene in a gene therapy vector. For example, different viral promoters with varying strengths of activity may be utilized depending on the level of expression desired. In mammalian cells, the CMV immediate early promoter if often used to provide strong transcriptional activation. Modified versions of the CMV promoter that are less potent have also been used when reduced levels of expression of the transgene are desired. When expression of a transgene in hematopoetic cells is desired, retroviral promoters such as the LTRs from MLV or MMTV are often used. Other viral promoters that may be used depending on the desired effect include SV40, RSV LTR, HIV-1 and HIV-2 LTR, adenovirus promoters such as from the E1A, E2A, or MLP region, AAV LTR, cauliflower mosaic virus, HSV-TK, and avian sarcoma virus.

Similarly tissue specific promoters may be used to effect transcription in specific tissues or cells so as to reduce potential toxicity or undesirable effects to non-targeted tissues. For example, promoters that are selectively active in lung and other airway tissues may be particularly useful.

In certain indications, it may be desirable to activate transcription at specific times after administration of the gene therapy vector. This may be done with such promoters as those that are hormone or cytokine regulatable. For example in gene therapy applications where the indication is a gonadal tissue where specific steroids are produced or routed to, use of androgen or estrogen regulated promoters may be advantageous. Such promoters that are hormone regulatable include MMTV, MT-1, ecdysone and RuBisco. Other hormone regulated promoters such as those responsive to thyroid, pituitary and adrenal hormones are expected to be useful in the present invention. Cytokine and inflammatory protein responsive promoters that could be used include K and T Kininogen (Kageyama et al., 1987), c-fos, TNF-alpha, C-reactive protein (Arcone et al., 1988), haptoglobin (Oliviero et al., 1987), serum amyloid A2, C/EBP alpha, IL-1, IL-6 (Poli and Cortese, 1989), Complement C3 (Wilson et al., 1990), IL-8, alpha-1 acid glycoprotein (Prowse and Baumann, 1988), alpha-1 antitypsin, lipoprotein lipase (Zechner et al., 1988), angiotensinogen (Ron et al., 1991), fibrinogen, c-jun (inducible by phorbol esters, TNF-alpha, UV radiation, retinoic acid, and hydrogen peroxide), collagenase (induced by phorbol esters and retinoic acid), metallothionein (heavy metal and glucocorticoid inducible), Stromelysin (inducible by phorbol ester, interleukin-1 and EGF), alpha-2 macroglobulin and alpha-1 antichymotrypsin.

It is envisioned that cell cycle regulatable promoters may be useful in the present invention. For example, in a bi-cistronic gene therapy vector, use of a strong CMV promoter to drive expression of a first gene such as p16 that arrests cells in the G1 phase could be followed by expression of a second gene such as p53 under the control of a promoter that is active in the G1 phase of the cell cycle, thus providing a "second hit" that would push the cell into apoptosis. Other promoters such as those of various cyclins, PCNA, galectin-3, E2F1, p53 and BRCA1 could be used.

Tumor specific promoters such as osteocalcin, hypoxia-responsive element (HRE), MAGE-4, CEA, alpha-fetoprotein, GRP78/BiP and tyrosinase may also be used to regulate gene expression in tumor cells. Other promoters that could be used according to the present invention include Lac-regulatable, chemotherapy inducible (e.g., MDR), and heat (hyperthermia) inducible promoters, radiation-inducible (e.g., EGR (Joki et al., 1995)), Alpha-inhibin, RNA pol III tRNA met and other amino acid promoters, U1 snRNA (Bartlett et al., 1996), MC-1, PGK, β-actin and α-globin. Many other promoters that may be useful are listed in Walther and Stein (1996).

It is envisioned that any of the above promoters alone or in combination with another may be useful according to the present invention depending on the action desired. In addition, this list of promoters is should not be construed to be exhaustive or limiting, those of skill in the art will know of other promoters that may be used in conjunction with the promoters and methods disclosed herein.

B. Enhancers

Enhancers are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

In preferred embodiments of the invention, the expression construct comprises a virus or engineered construct derived from a viral genome. The ability of certain viruses to enter cells via receptor-mediated endocytosis and to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986).

III. Polyadenylation Signals

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human or bovine growth hormone and SV40 polyadenylation signals. Also contemplated as an element of the expression cassette is a terminator. These elements can serve to enhance message levels and to minimize read through from the cassette into other sequences.

IV. IRES

In certain embodiments of the invention, the use of internal ribosome entry site (IRES) elements is contemplated to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (poliovirus and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

E. Vector Delivery

I. Viral Receptor Expression

The inventors have identified one of the main barriers to viral uptake in epithelial tissue as the apparent lack of accessibility to viral receptors when viral particles are applied to the apical surface of polarized epithelial cells. The viral receptors appear to be readily accessible primarily from the basal side of the epithelia. In particular, the efficiency of viral infection, as exemplified here with retroviruses, is determined in part by the availability of specific cellular receptors that mediate virus entry (Miller, 1996; Weiss and Tailor, 1995). Thus, the inventors' observation that retroviral gene transfer to proliferating airway epithelia is polar is very important.

Little is known regarding the biology of retrovirus and its receptor interactions in these cells. Other than the observations that amphotropic (Olsen et al., 1993) or GALV (Bayle et al., 1993) enveloped vectors can infect airway epithelia, there has been little work to characterize the abundance, cellular location, or regulation of receptor expression in airway epithelia. However, there is considerable precedence in epithelia for viral infection to occur in a polarized fashion. Studies in high resistance MDCK cells conclusively showed that vesicular stomatitis virus infected at least 100 times more efficiently when applied to the basal side than when applied to the apical surface of these epithelia (Fuller et al., 1984).

Similarly, vaccina virus (Rodriguez et al., 1991) and canine parvovirus (Basak and Compans, 1989) preferentially infect the basolateral surface of epithelia, while cytomegalovirus (Tugizov and Pereira, 1996), measles virus (Blan and Compans, 1995) and simian virus 40 (Clayson and Compans, 1988) infects more efficiently from the apical surface. Thus, other vectors also show similar preferences for portions of polarized cells.

The efficiency of infection with retroviruses is determined in part by the availability of specific cellular receptors that mediate virus entry (Miller, 1996; Weiss and Tailor, 1995). In the case of amphotropic enveloped (env) retrovirus, the receptor has been cloned from rat and human cells and is called Ram-1 (rodent) or GLVR-2 (human) or more recently Pit2. It has been shown to be a cell surface protein that functions as a sodium-dependent phosphate transporter (Miller et al., 1994; Miller and Miller, 1994). Several other specific MMLV receptors exist and have been cloned, but the receptor for the xenotropic envelope is currently unknown (Miller, 1996). Binding of the amphotropic envelope glycoprotein gp70 to Ram-1 initiates viral infection and in hematopoetic cells (Orlic et al., 1996) and hepatocytes (Hatzoglou et al., 1995) levels of Pit2 mRNA expression correlate directly with infection efficiencies. In some cases receptor abundance and infectivity is regulated by nutritional or hormonal conditions. For example, there is evidence for the regulation of Ram-1 mRNA expression by insulin, dexamethasone (Wu et al., 1994) or hypophosphatemia (Chien et al., 1997; Miller and Miller, 1994; Richardson and Bank, 1996). The findings presented here suggest that, in addition to stimulating cell proliferation, growth factors also increase the expression of the Pit-2 amphotropic receptor protein.

II. Increasing Permeability

It was observed that procedures which increased transepithelial permeability enhanced gene transfer after vector was applied to the apical surface. The tight junction, also known as zonula occludens, is the apical-most component of the epithelial junctional complex (Anderson and Itallie, 1995). A variety of tissue permeabilizing agents transiently increase epithelial permeability by disrupting tight junctions. Bhat and co-workers reported that lowering intra- or extracellular calcium levels or disrupting the cytoskeleton reversibly increased permeability in rabbit tracheal epithelium (Bhai et al., 1993). Widdicombe and colleagues found that hypotonic shock from the application of water to the apical surface transiently increased the permeability of cultured bovine or human tracheal epithelia (Widdicombe et al., 1996). Hypotonic shock reversibly increased both transcellular and paracellular permeability (Widdicombe et al., 1996).

Intraepithelial permeability, according to the present invention, can therefore be increased by contacting the epithelial tissue with a tissue permeablizing agent including those that lower calcium levels, disrupt the cytoskeleton or cause hypotonic shock. Calcium levels can be lowered by introducing ion chelators such as EGTA, BAPTA or EDTA. Cytoskeletal disruption agents include cytochalasin B or colchicine. Hypotonic solutions are defined relative to normal osmolality, or normotonic solutions. Normotonic solutions are around 280–300 mosm/kg. The hypotonic solutions according to the present invention are less than about 280 mosm/kg. One particular buffer is about 105 mosm/kg, while others are about 25–50 mosm/kg.

Other tissue permeablizing agents include poly-L-lysine, E-cadherin antibodies, occludin peptides, ether, neurotransmitters, FCCP, oxidants and mediators of inflammation. Neurotransmitters that can be used include capsianoside. Oxidants that can be used include ozone, and mediators of inflammation include TNFα.

III. Modes of Action

There are several possible reasons for the increase in gene transfer noted under the experimental conditions used herein. Perhaps the most simple interpretation is that Pit-2 expression is polarized in human airway epithelia and primarily localized to the basolateral surface of all cells of the epithelial sheet. In support of this hypothesis, techniques that are known to transiently disrupt the integrity of epithelial tight junctions (i.e. hypotonic shock, low $Ca^{2+}$) enhanced gene transfer efficiency with amphotropic or xenotropic vector applied to the mucosal surface. Disruption of tight junctions may also cause a transient loss of cell polarity and shifting of receptors to the apical pole. Since hypotonic conditions transiently increase apical membrane permeability to macromolecules (Widdicombe et al., 1996), it also is conceivable that vector may have entered cells via a receptor-independent fashion during hypotonic conditions. Finally, it also is possible that the apical treatment procedures removed mucus or inhibitory factors from the apical surface.

Another potential advantage of delivering viral vectors via increased transepithelial permeability is the ability to target certain epithelial cells. There is controversy regarding which epithelial cells to target for gene therapy in chronic diseases such as CF. Arguments can be made in support of correcting cells of the surface epithelium, the submucosal glands, or both (Yamaya, 1991; Engelhardt et al., 1992). A goal of gene transfer to the pulmonary epithelium with integrating vectors is to correct the genetic defect in a population of cells which could pass the corrected gene on to their progeny. There appear to be several epithelial cell types in the lung that are able to divide. Some of these cells may represent a pluripotent or "stem cell" population. Studies from several species and model systems suggest these populations exist; basal cells and non-ciliated columnar cells of the airways (Randell, 1992; Ford and Terzaghi-Howe, 1992.); Clara cells (Evans et al., 1976) and alveolar type II cells (Adamson and Bowden. 1974; Evans, et al., 1975) in the distal lung. The invention allows the practitioner to target basal cells for infection by viral expression vectors. This in turn can enhance the duration of transgenic expression by targeting integrating vectors to epithelial cells with the capacity to transmit genetic material to daughter cells.

F. Pharmaceuticals and Routes of Administration

In clinical applications, it will be necessary to prepare the viral particles of the present invention as pharmaceutical compositions, i.e. in a form appropriate for in vivo applications. Generally, this will entail preparing compositions that are essentially free of pyrogens, as well as other impurities that could be harmful to humans or animals.

One will generally desire to employ appropriate salts and buffers to render viral vectors compositions stable and allow for uptake by target cells. Aqueous compositions of the present invention comprise an effective amount of the viral vector, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors of the present invention, its use in therapeutic compositions is contemplated. Supplementary active ingredients also can be incorporated into the compositions.

The viral particles of the present invention include classic pharmaceutical preparations. Administration of these compositions according to the present invention will be via any common route so long as the target tissue is available via that route. This includes oral, nasal, buccal, rectal, vaginal or topical. Alternatively, administration may be by aerosol, intradermal, subcutaneous, intramuscular, intraperitoneal or intravenous injection. Such compositions would normally be administered as pharmaceutically acceptable compositions, described supra.

The particles may be administered via any suitable route, including parenterally or by injection. Solutions of the active compounds as free base or pharmacologically acceptable salts can be prepared in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the viral particles in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration.

"Unit dose" is defined as a discrete amount of a therapeutic composition dispersed in a suitable carrier. For example, in accordance with the present methods, viral doses include a particular number of virus particles or plaque forming units (pfu). For embodiments involving adenovirus, particular unit doses include $10^3$, $10^4$, $10^5$, $10^6$, $10^7$, $10^8$, $10^9$, $10^{10}$, $10^{11}$, $10^{12}$, $10^{13}$ or $10^{14}$ pfu. Particle doses may be somewhat higher (10 to 100-fold) due to the presence of infection defective particles.

In this connection, sterile aqueous media which can be employed will be known to those of skill in the art in light of the present disclosure. For example, a unit dose could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

In one embodiment, the present invention is directed at the treatment of human malignancies. A variety of different routes of administration are contemplated. For example, a classic and typical therapy will involve direct, intratumoral injection of a discrete tumor mass. The injections may be single or multiple; where multiple, injections are made at about 1 cm spacings across the accessible surface of the tumor. Alternatively, targeting the tumor vasculature by direct, local or regional intra-arterial injection are contemplated. Also contemplated are methods for aerosol delivery to the airway.

In another embodiment, the present invention is directed at the treatment of diseases of the airway, including the trachea and bronchial passages. An ideal delivery method is via aerosol. U.S. Pat. No. 5,543,399 (incorporated by reference) describes methods for the delivery of compositions including the CFTR gene to airway. U.S. Pat. Nos. 5,756,353 and 5,641,662 (both incorporated by reference) also describe delivery of genes to the lung by aerosol. Other airway delivery methods and compositions are described, for example, in WO 93/12240, WO 90/07469, WO 96/27393, WO 96/22765 and WO 96/32116, all of which are incorporated by reference. Another method is instilling the vector solution, appropriately formulated, into the airways using bronchoscopic techniques.

G. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Materials and Methods

The present example details some of the methods employed in the present invention.

I. Cell Culture Methods

Primary culture of human airway epithelia. Primary cultures of human airway epithelia were prepared from trachea and bronchi by enzymatic dispersion as previously described (Konda et al., 1991; Yamaya et al., 1992; Zabner et al., 1996). Briefly, epithelial cells were dissociated and seeded onto collagen-coated, semipermeable membranes with a 0.4 $\mu$m pore size (Millicell-HA, surface area 0.6 cm$^2$, Millipore Corp., Bedford, Mass.). 24 hours after seeding, the mucosal media was removed and the cells were allowed to grow at the air-liquid interface as reported previously (Yamaya et al., 1992). The culture media consisted of a 1:1 mixture of DMEM and Ham's F12 with 2% Ultroser G (Sepracor Inc., Marlborough, Mass.), 100 U/ml Penicillin and 100 $\mu$g/ml Streptomycin. Representative preparations from all cultures were scanned by EM and the presence of tight junctions confirmed by transepithelial resistance measurements (resistance>1000 Ohm×2 cm$^2$). All preparations used in the study were well differentiated and only well differentiated cultures>2 wk old were used in these studies. Previous studies show that differentiated epithelia in this model are multilayered and consist of ciliated cells (cytokeratin 18 positive), secretory cells containing granules that are reactive to goblet and mucous cell specific antibodies, and basal cells positive for cytokeratin 14 (Yamaya et al., 1992; Zabner et al., 1996). This study was approved by the Institutional Review Board of the University of Iowa.

II. Reagents

Recombinant retrovirus and vector formulation. High titer recombinant amphotropic and xenotropic retroviruses were prepared at Chiron Technologies-Center for Gene Therapy, Inc. (San Diego, Calif.) as described previously (Bosch et al., 1996; McCray et al., 1997a). Reporter viruses used included DA-βgal (β-galactosidase reporter, amphotropic envelope) and DX-βgal (β-galactosidase repoder, xenotropic envelope) (Irwin et al., 1994; Jolly, 1994). The β-galactosidase reporter gene was driven by retroviral LTR. The vector formulation buffer was 19.5 mM trimethamine at pH 7.4, 37.5 mM NaCl, and 40 mg/ml lactose. The osmolality of the viral buffer was 105 mmol/kg as measured using a vapor pressure osmometer (Model 5500, Wescor, Inc., Logan, Utah). Polybrene was included in all infection mixtures at a concentration of 8 $\mu$g/ml.

A vector expressing human CFTR was prepared by cloning the human CFTR cDNA (Rommens et al., 1989) into a retroviral vector plasmid with the viral LTR promoter (Jolly, 1994). Producer clones were selected based on the ability of crude vector stocks to confer cAMP-activated Cl$^-$ transport to undifferentiated CF epithelia in vitro and a stable producer cell line was selected (Jolly, 1994; McCray et al., 1993). For gene transfer to differentiated CF airway epithelia, crude producer cell supernatants were concentrated by centrifugation and applied to epithelia. This may be performed with or without growth factor stimulation. Epithelia were tested for the presence of CFTR Cl$^-$ currents in Ussing chambers 3 to 10 days after gene transfer as previously described (McCray et al., 1993).

In selected studies, transepithelial permeability was increased before or at the time of application of vector to the apical membrane of cultured epithelia. Treatment conditions included water or EGTA. For EGTA treatment, a solution of 1.5 mM EGTA in water (osmolality 33 mmol/kg) was used to rinse the apical side of cells for 20 min. An EGTA:virus mixture was obtained by mixing the viral preparation and 3 mM EGTA in water at a 1:1 ratio (osmolality 48 mmol/kg). Gene transfer to the apical surface was performed by applying vector in 100 $\mu$l volumes. For gene transfer to the basal side of the cell membrane, the Millicell culture insert was turned over and vector applied to the bottom of the membrane in a 100 $\mu$l volume.

III. Assessment of Cell Proliferation

BrdU immunohistochemistry. BrdU labeling and immunostaining was performed using a kit from Zymed Laboratories Inc. (South San Francisco, Calif.). In studies that investigate the effects of growth factors, the cells may be treated with 50–100 ng/ml growth factor for 36 h. A 1:100 dilution of the BrdU labeling reagent was added to the culture media and cells labeled for 4 hours followed by fixation in 10% neutralized Formalin. BrdU histochemistry was performed following the methods of the Zymed BrdU kit. Labeled nuclei stained brown under these conditions. Epithelial cell preparations were examined microscopically en face or in cross sections of paraffin embedded membranes and the percentage of brown staining nuclei determined. Hematoxylin or 4',6-diamidino-2-phenylindole, dibydrochloride (DAPI) (Molecular Probes, Eugene, Oreg.) were used for counterstains.

β-galactosidase expression. Epithelial cells were fixed with 2% paraformaldehyde/PBS solution for 20 min and rinsed with PBS twice for 5 min each. X-gal staining solution was added to the cells at 37° C. for 4 hours to overnight as previously described (McCray et al., 1995). Cell membranes were examined microscopically en face or in cross section for β-galactosidase expression. The percentage of β-gal positive cells was determined by counting a minimum of 1000 cells from cross sections of each treated cell culture insert.

IV. Identification of amphotropic retroviral receptor (Pit-2) in cultured human airway epithelia.

Pit-2 antibody. Affinity purified polyclonal Pit-2 antisera were prepared by immunizing rabbits with a synthetic peptide (GLVR-2A), an extracellular domain sequence that is conserved in rat and human Pit-2 (Miller et al., 1994; Miller and Miller, 1994). The peptide was coupled to key hole limpet hemocyanin (KLH) and rabbits were then immunized. Different post immunization bleeds were tested using ELISA and immobilized 'free' peptide. Resulting antipeptide antisera were pooled and affinity purified on columns of immobilized GLVR-2A peptides. These affinity purified antibodies were then used for all Pit-2 expression analyses.

Western blot. Airway epithelial cells were lysed in 10 mM Tris/HCl buffer (pH 7.4) containing 0.5% Triton-X 100 and 1 mM PMSF. Cell lysates were collected and protein concentrations determined by the Lowry method. 35 µg of protein in loading buffer was denatured at room temperature (not boiled) for 40 min and run on a 10% polyacrylamide SDS gel. Following electrophoresis, the proteins were transferred to a Nytran membrane (Schleicher and Schuell Inc., Keene, N.H.) by electroblotting and blocked with 10% skim milk powder. Immunoblotting was performed with the polyclonal antisera at a 1:10,000 dilution. Goat anti-rabbit IgG conjugated with horseradish peroxidase was used for the secondary antibody (Bio-Rad, Hercules, Calif.) and the proteins identified by autoradiography using the ECL system (Amersham, Arlington Heights, Ill.). The specificity of the antibody was confirmed by preincubating the antibody with 20 µM free synthetic peptide for 30 min in PBS, 1% BSA at room temperature prior to incubation with the blots.

Measurement of transepithelial resistance. Differentiated epithelial cells can be treated with 50 ng/ml the desired growth factor for 24 h. Transepithelial resistance was measured as follows: Solutions of water or 1.5 mM EGTA in water are used to rinse the apical side for 20 min. The solution was then replaced with viral formulation buffer alone, or a 1:1 mixture of viral formulation buffer plus 3 mM EGTA water solution, and incubated for 4 h. Control cells can receive growth factor treatment and PBS washes substituted for water or EGTA washes. Transepithelial resistance was monitored with an ohmmeter (EVOM; World Precision Instruments, Inc. Sarasota, Fla.) over 16–18 hours until resistance returned to base line.

EXAMPLE 2

Growth Factors Stimulate Proliferation of Differentiated Airway Epithelia In Vitro and In Vivo To determine whether growth factors are mitogenic to human airway epithelia, primary cultures of cells grown at the air-liquid interface were utilized. These cultures have ion transport properties and morphology similar to the intact surface epithelium (Smith et al., 1996; Kondo et al., 1991) and after 14 days in culture the cells are well-differentiated, ciliated, and have ion transport properties similar to the intact airways (Zabner et al., 1996; Yamaya et al., 1992). The data show that 200 ng/ml of HGF stimulated cell division 3-fold as measured by [$^3$H] thymidine incorporation. After 24 hours of growth factor treatment, growth factor administration doubles the monolayer cell number compared to control. HGF treatment (200 ng/ml) increased cell labeling to 17–36%, while 5–10% of untreated controls were BrdU positive (n=3). EGF (200 ng/ml) and heregulin (5 nM) also both increased BrdU incorporation over control epithelia. These results clearly docunent that differentiated, mitotically quiescent human airway epithelia proliferate in response to growth factors.

In order to investigate whether growth factors stimulate epithelial proliferation in vivo, the desired growth factor (e.g., 5 µg/g) may be instilled into the tracheas of 3 wk old rats once daily on two consecutive days. On days 3, 4, 5, and 7 following the first instillation the animals are given an injection of bromodeoxyuridine (BrdU) and sacrificed. The tissues are formalin fixed, paraffin embedded, and sections immunostained for BrdU and PCNA (proliferating cell nuclear antigen) (McCray et al., 1997b). Immunostaining with an antibody to PCNA will serve to identify the regions and cell types in the lung showing proliferation in response to the growth factor applied. It is predicted that it is likely that animals that receive intratracheal growth factors will develop a transient wave of epithelial cell proliferation that is greatest in the alveolar epithelium when compared to PBS treated control animals. Such a peak proliferative response is expected to occur within 72 hours after the second dose of growth factor for both bronchiolar and alveolar epithelia. Tissue sections are expected to demonstrate a "knobby" epithelial proliferation pattern in the alveolus suggestive of type II cell proliferation. Morphologically these findings would be similar to those reported in adult rats in response to intratracheal KGF (Ulich et al., 1994). Proliferating cells also may be noted in the bronchiolar epithelium of growth factor treated rats. These studies should conclusively demonstrate that growth factors stimulate airway epithelial proliferation both in vitro and in vivo.

Gene transfer is polar in differentiated human airway epithelia. Next, it was of interest to determine whether the levels of epithelial proliferation stimulated by growth factors supported gene transfer with high titer amphotropic enveloped MMLV expressing β-galactosidase (DA-βgal). To address this question, airway epithelia are stimulated with growth factors for 24 hours followed by application of DA-βgal amphotropic vector (MOI~20) to the apical side of the membrane for 4 h. Three days after infection, X-gal staining may be performed to evaluate transgene expression. When vector is applied to the apical membrane of quiescent or growth factor stimulated cells no gene transfer is seen. It was hypothesized that the Pit-2 amphotropic receptors were not accessible from the apical surface. To test this hypothesis, the epithelial sheets were inverted and vector was applied to the basal surface for 4 hours at an estimated MOI of 20; 72 hours later numerous β-gal expressing epithelia were noted. Vector application to the basal side of growth factor-treated epithelia results in improved gene transfer, with significant numbers of cells expressing the transgene. The cells expressing the transgene are predominantly those with their basal membrane in contact with the membrane support and many had morphologic characteristics of basal cells. Cells that received no growth factor also show occasional X-gal positive cells when vector was applied to the basal surface, in agreement with the lower mitotic indices of cells grown under these conditions. Thus, gene transfer with MMLV is strikingly polar in differentiated human airway epithelia. It also was found, using the same experimental protocol, that gene transfer with MMLV vectors with the xenotropic envelope and VSV-G pseudotype show similar polarity of gene transfer. These results were unexpected and suggested that either the receptors for amphotropic and xenotropic viruses were not present or that they were inaccessible to virus applied to the apical surface. Next studies were performed to determine if the Pit-2 receptor was expressed on human airway epithelia and if growth factor application influenced Pit-2 expression.

The GLVR-2 amphotropic receptor is expressed in airway epithelia and upregulated by growth factors. Retroviral transduction begins with the interaction and binding of viral envelope glycoproteins and cell surface receptors. In the case of amphotropic enveloped vectors, the receptor (Pit-2) has been cloned and identified as a sodiumn-dependent phosphate transporter (Miller et al., 1994; van Zeijl et al., 1994), a 656 amino acid transmembrane protein. Other than Northern blot data demonstrating that the amphotropic receptor mRNA is present in whole lung from rat (Miller et al., 1994), there are no data regarding the abundance and distribution of Pit-2 protein in the lung. Rabbit polyclonal antisera generated against a synthetic peptide sequence shared by rat and human Pit-2 was used in Western blots and identified a protein of ~62 kD in rat lung. The 62 kD band was competed off in the presence of the synthetic peptide. When rats are treated with intratracheal growth factors, the abundance of the protein will transiently increase, with the highest level of expression expected at 48 hours after the first dose of growth factor. Similarly, quiescent human airway epithelial cells express low levels of Pit-2 protein and protein abundance can be increased following growth factor treatment.

Vector application from the mucosal and serosal surface targets different cell populations. The marked polarity of gene transfer to differentiated epithelia suggested that access to receptors was extremely limited from the apical surface. Thus, it is suggested that if Pit-2 receptors are located on the basolateral membrane, transiently disrupting epithelial tight junctions might allow vector access to the receptor. This may be tested by adding 50 $\mu$l of water or 3 mM EGTA in water to the apical surface of growth factor-stimulated human monolayers for 20 min and then adding vector to the mucosal surface for 4 h. These treatments should cause a transient fall in transepithelial resistance that fully returns to baseline over several hours. Such interventions dramatically increase gene transfer efficiency. 3±0.5% of epithelia from preparations pretreated with water alone expressed $\beta$-gal (mean±SE, n=13 membranes from 3 preparations). Sequential treatment with water then EGTA in water for 10 min each, followed by addition of vector result in 8±1.3% cells positive. A further incremental increase in expression was seen in cells pretreated with a combination of water and EGTA for 20 min followed by addition of vector (20.3±2.5% cells positive, mean±SE, n=9 membranes from 2 preparations). Finally, cells pretreated with water and EGTA for 20 miin followed by the addition of vector containing EGTA showed a further increase in gene transfer such that 34.3±5.4% of the cells were $\beta$-gal positive 3 days following vector delivery (mean±SE, n=9 membranes from 2 preparations). In control studies, it was shown that application of $H_2O$ or EGTA to epithelia had no effect on proliferation.

Different cell populations were targeted when vector was applied to the basal surface or when it was applied to the apical surface in the presence of EGTA. In contrast to the results obtained with vector applied to the basal surface of the epithelia, cells at both the apical and basal levels of the cell layer were transduced under these conditions (basal cells, ciliated cells, intermediate cells). To quantify the differences in cells targeted between these two methods, $\beta$-gal expressing cells were identified in the epithelium and scored using morphologic criteria as basal cells (cuboidal cells in contact with the basement membrane whose apical pole does not reach the lumen), ciliated cells (columnar cells with cilia), or intermediate cells (columnar cells residing in the lower half of the surface epithelium with no lumenal contact or secretory granules). Using these criteria, 200 $\beta$-gal positive cells were counted in the cell layers in which vector was applied to basal side only and in cells in which vector applied to apical surface with EGTA in vector buffer. For the vector applied to the basal surface, the results were: 80% basal, 13% intermediate, and 7% ciliated. In contrast, for the apical/EGTA application, the results were: 36% basal, 36% intermediate and 28% ciliated. Therefore, it was concluded that vector application to the basal surface targets predominantly basal cells while apical application with EGTA targets cells at all levels of the epithelial sheet.

Next, it was asked whether other growth factors that stimulate epithelial proliferation facilitated gene transfer with MMLV. Differentiated human airway epithelia were treated with HGF (200 ng/ml), EGF (200 ng/ml), or heregulin (5 nM) for 24 hours. Then high titer ($1 \times 10^8$ cfu/ml) nuclear targeted $\beta$-gal vector was applied to the apical surface (MOI~10) in hypotonic buffer with EGTA. Each growth factor stimulated proliferation. Cells treated with HGF and heregulin showed similar proliferative responses. The finding of different levels of gene transfer following equivalent proliferative responses with HGF and heregulin suggests that in addition to cell division, growth factors have other effects that allow gene transfer with MMLV.

Gene transfer to proliferating differentiated CF airway epithelia corrects the Cl⁻ transport defect. The results with MMLV $\beta$-gal vectors in combination with growth factors suggest that it might be possible to correct the CF defect in epithelia using such an approach. However, it was not known if the cell types targeted using such an approach would be sufficient to correct Cl⁻ transport. Therefore, a high titer amphotropic MMLV vector expressing the human CFTR cDNA (DA-CFTR) was generated. Then, the question was asked whether the strategy used above could also enhance gene transfer with a CFTR vector and correct the Cl⁻ transport defect. Supernatants were collected from the DA-CFTR packaging cell line and the vector was concentrated. Differentiated human airway epithelia are treated with growth factors for 24 hours followed by application of DA-CFTR (estimated MOI~1) to the mucosal surface in the presence of 3 mM EGTA. 10 days later epithelia with and without vector application were assayed for cAMP activated Cl⁻ current in Ussing chambers. In control cells that received no vector application, correction of the CFTR transport defect was not detected. Only cells receiving the CFTR vector showed evidence of cAMP activated Cl⁻ current. This is a novel observation for MMLV-based vectors as previous studies were only able to document correction of the CF transport defect if the retroviral vector was applied to poorly differentiated, dividing cells (Engelhardt et al., 1992).

EXAMPLE 3

An Integrating Vector can Target Nondividing Cells and Produce Persistent Expression and Correction of the CF Defect If an integrating vector can infect nondividing cells it might offer advantages for gene transfer to airway epithelia because the level of proliferation in the airways in vivo is normally very low. Several recent studies demonstrate that hybrid lentiviral vectors infect nondividing mammalian cells (Naldini et al., 1996; Kafri et al., 1997). However, the one report of gene transfer to human airway epithelia with HIV-based lentivirus suggests that the gene transfer efficiency is greater in cells that are proliferating (Goldman et al., 1997). In a preliminary study, HIV-based lentivirus was applied to the apical or basal surface of differentiated human airway in basal media in the absence of growth factors. The vector expresses E coli β-galactosidase and the envelope is pseudotyped with the VSV-G protein. Crude vector supernatants were prepared by transiently co-transfecting 293T cells with 3 plasmids and the final concentration and purification of the vector was completed. Similar to the findings with MMLV-based vectors, when VSV-G lentivirus was applied to the apical surface of epithelia without pretreatment with growth factors (MOI~1), no gene transfer occurred. In contrast, when vector was applied to the basal surface of quiescent epithelia, β-galactosidase expressing cells were noted. Thus, the same polarity of gene transfer that was noted with the MMLV amphotropic envelope is noted for the VSV-G pseudotyped vector. When the vector was applied to the apical surface of quiescent cells in the presence of EGTA/hypotonic buffer, gene transfer was enhanced. From this study, it was concluded that HIV-based lentivirus can infect non-dividing well-differentiated airway epithelia. Similarly, a study with FIV-based lentivirus gave similar results. Importantly, airway epithelia that are growth arrested by aphidicolin are susceptible to infection by HIV- and FIV-based lentiviruses.

EXAMPLE 4

Integrating Vectors Can Correct the CF Defect in Differentiated Epithelia in vivo $Ca^{2+}$ Chelation Transiently Disrupt Epithelial Tight Junctions in vivo Preliminary studies were performed in rats to test the feasibility of using hypotonic solutions with EGTA to increase transepithelial permeability in vivo. 3 wk old rats were tracheotomized and a small caliber PE catheter inserted into the left lobe of the lung. 100 µl of 3 or 12 mM EGTA in water or PBS was mixed with 100 nM fluorescent beads (a marker for viral particles) and instilled into the lungs. One hour later the animals were sacrificed and lung, tissue sections examined under fluorescence microscopy to determine if the fluorescent beads penetrated the epithelial layer. In the PBS control animal, fluorescent particles were only noted in the airway lunen. In contrast, in animals receiving either 3 or 12 mM EGTA, beads were seen throughout the cell layer and close to the basement membrane. It also was asked if animals treated with EGTA/H2O developed changes in lung morphology. Animals received PBS or 12, 60, or 120 mM EGTA/water into the left lobe of the lung and 1 wk later were sacrificed and H & E stained lung tissues examined. The lungs of all animals showed morphology similar to the control except for the animal that was treated with 120 mM EGTA. In that animal thickening of the interstitial space was noted in tissue sections. These studies demonstrate the feasibility of using maneuvers that transiently disrupt tight junctions for in vivo gene transfer with integrating vectors.

Growth factors stimulate epithelial proliferation in a CF mouse model. The ΔF508 CF mouse is a model for correcting the CFTR transport defect in vivo using the nasal epithelium as a model. In order to investigate whether the murine nasal epithelium proliferates in response to growth factors, adult mice are sedated and given growth factor compositions via IV and intranasally on 2 consecutive days. On day 3 the animals are given intraperitoneal and intranasal doses of BrdU and sacrificed 2 hours later. Based on BrdU histochemistry animals treated with growth factor should show an increase in proliferating cells compared to controls. Such results provide confirmation that growth factors stimulate proliferation of nasal epithelia.

Growth factors stimulate epithelial proliferation in human bronchial xenografts. The tracheal xenograft model closely resembles the CF human airways in terms of morphology, electrophysiologic defects and biochemical defects. Studies were performed to verify whether growth factors stimulate proliferation in tracheal xenografts populated with human airway epithelia. 100 ng/ml of the desired growth factor is instilled into the lumen of mature differentiated xenografts on 2 consecutive days. Simultaneously, animals are given 5 µg/g growth factor intravenously each day. PCNA histochemistry demonstrates that growth factor-treated grafts show an increase in the number of PCNA positive epithelia.

EXAMPLE 5

In vivo Demonstration of Growth Factors Stimulation of Transient Epithelial Proliferation The present example provides a description of the type of experiment to be performed in order to evaluate whether growth factors stimulate transient epithelial proliferation in vivo. This example give details of the animals and procedures to be used in such a study.

Animal Procedures

Sprague-Dawley rats (age 15–20 days, weight ~30 g) can be used in these studies. Growth factor and recombinant retrovirus may be delivered to the lung by direct tracheal instillation. Animals are then anesthetized with methoxyfluorane, gently restrained and the larynx visualized. A 22 gauge Teflon intravenous catheter is passed through the mouth and into the trachea and the growth factor or viral suspension instilled using a 1 ml tuberculin syringe To stimulate epithelial proliferation in the lung, animals are given an appropriate amount of growth factor (e.g., 2.5 µg/g body weight) intratracheally, twice daily on consecutive days. Control animals should receive PBS in equal volume. This growth factor dose range has was previously shown to stimulate proliferation in the alveolar and bronchiolar epithelia of adult rats (Ulich et al., 1994). In the gene transfer studies, animals receive 80 µl of DA-βgal intratracheally on 3 consecutive days following growth factor administration (total dose ~$10^7$ cfu/animal). Control animals receive an equal volume of diluent.

Tissue Histochemistry

Cell proliferation by PCNA staining. Proliferating pulmonary epithelial cells are identified using antibodies against proliferating cell nuclear antigen (PCNA, PC10 clone, Dako) as previously described (McCray et al., 1997; Schwarting, 1993). To determine the percentage of cells proliferating in response to a growth factor, groups of animals receive the appropriate amount of growth factor (e.g., 5 µg/g/day) or PBS on days 1 and 2. On days 3, 4 and 7 groups of animals are killed and lungs are prepared for PCNA analysis.

Immunohistochemistry is performed on 5 micron thick sections of paraffin-embedded, formalin fixed tissues. The PCNA antibody is applied at a 1:100 dilution overnight at 4° C. This monoclonal antibody recognizes the 36 kD polymerase delta accessory protein, a DNA binding protein expressed in cells in the G1, S, M, and G2 phases of the cell cycle. The labeled strepavidin biotin peroxidase (LSAB Dako Corp., Santa Barbara, Calif.) detection system can be used for detection, after antigen retrieval (citrate buffer and microwave). Positive cells will stain brown with this method. Sections can be counterstained with hematoxylin. Human tonsil may be used as a positive control, while in the negative control the primary antibody was omitted.

PCNA positive cells from random fields (40× magnification) are counted from a number of non-adjacent fields for each section, with a minimum of 100 cells per field counted per animal. Brown staining nuclei is scored regionally as alveolar or bronchiolar. Differences in proliferation between growth factor-treated groups and PBS controls may be analyzed. The percentage of PCNA positive staining in the control (PBS) group is considered background and was subtracted from the growth factor groups in the analysis.

X-gal staining. To detect gene expression in animals treated with growth factor, animals are killed 5 days after the final dose of intratracheal retrovirus, lungs are removed and perfused with 2% paraformaldehyde in PBS and fixed overnight. Lungs are stained for 4 h at 37° C. with 40 mg/ml of X-gal from Gold Biotechnology Inc. (St. Louis, Mo.) using previously described techniques (McCray Jr. et al., 1995). After en bloc staining, tissues are frozen in O.C.T. and 10 $\mu$m sections placed onto slides and counter-stained in nuclear fast red for photomicroscopy. Cells expressing β-galactosidase stain blue with a cytoplasmic pattern using this method.

Detection of amphotropic retrovirus receptor (Pit2) expression by western blot. Lung tissue is homogenized in lysis buffer (10 mM Tris/HCl, pH 7.4, 1 mM PMSF, 0.5% Triton X-100). The resultant cell lysate is collected and protein quantified by the Lowry method. 35 $\mu$g of total protein from each sample is then loaded in a 10% SDS-PAGE gel. Following transfer to a Nytran membrane (Midwest Scientific, St. Louis, Mo.), Pit2 protein is identified by immunoblotting with rabbit antisera. Affinity purified polyclonal Pit2 antisera may be prepared by immunizing rabbits with a synthetic peptide (GLVR-2A), a Pit2 extracellular domain sequence that is conserved in rat and human (Miller et al., 1994; Miller and Miller, 1994). The peptide is coupled to key hole limpet hemocyanin (KLH) and rabbits are then immunized. Different post immunization bleeds may be tested using ELISA and immobilized 'free' peptide. Resulting anti-peptide antisera is then pooled and affinity purified on columns of immobilized GLVR-2A peptides. The affinity purified antibodies are used for subsequent Pit2 expression analyses. Goat anti-rabbit serum conjugated with horseradish peroxidase may be used as a second antibody (Bio-Rad). Specific antigen and antibody reaction can be detected by the ECL system (Amersham).

In vitro gene transfer to rat airway epithelia by apical or basolateral administration. Primary cultures of rat airway epithelia can be prepared from trachea by enzymatic dispersion using methods similar to those described for human epithelia (Zabner et al., 1996). Epithelial cells can be dissociated and seeded at a density of 3×10$^5$ cells/cm$^2$ onto rat tail collagen-coated permeable membranes with a 0.4 $\mu$m pore size (Millicell-HA, surface area 0.6 cm$^2$, Millipore Corp., Bedford, Mass.). 24 h after seeding, the mucosal media is then removed and the cells are allowed to grow at the air-liquid interface as reported previously (Zabner etal., 1996; Yamaya etal., 1992). The cells are maintained at 37° C. in a humidified atmosphere of 7% CO2 and air. Preparations from all cultures are then examined by transepithelial resistance measurements. It is recommended that only well-differentiated airway cells which demonstrate tight junction formation and high transepithelial resistances (R$_{te}$>1000 Ohm×cm$^2$) be used in the study. Nuclear targeted β-gal retroviral vector is applied to growth factor-stimulated differentiated epithelia at an MOI of ~20 on apical side or basolateral side and incubated for 4 h. Three days later, transgene expression can be assessed by X-gal histochemical staining.

Expected Results

Immunostaining with an antibody to PCNA will identify the regions and cell types in the lung which proliferate in response to the growth factor. It is expected that those animals that receive intratracheal growth factor over 2 consecutive days will likey develop a transient wave of epithelial cell proliferation that is greatest in the alveolar epithelium when compared to PBS treated control animals. Tissue sections may idemonstrate a "knobby" epithelial proliferation pattern in the alveolus, suggestive of type II cell proliferation. Proliferating cells also may be present in the bronchioles.

Growth factor induced proliferation facilitates retroviral-mediated gene transfer. In order to determine if growth factor-induced epithelial proliferation facilitates gene transfer with high titer amphotropic enveloped retrovirus, 80 $\mu$l of DA-βgal retrovirus is instilled intratracheally for 3 consecutive days following pretreatment with growth factor as described above. The total delivered dose should be approximately 1×10$^7$ cfu/animal. Five days following the final dose of virus, animals are sacrificed and tissues fixed and X-gal stained. Tissue sections from animals that receive growth factor and retrovirus should show epithelial cells expressing cytoplasmic β-galactosidase. β-gal positive cells should be most prevalent in the alveolar epithelium with a more rare positive bronchiolar cells. In contrast, rats that receive retrovirus without growth factor pretreatment should show no β-gal expressing cells.

Expression of the amphotropic receptor (Pit2) in vivo. Amphotropic retroviral infection is mediated through the Pit2 receptor. A lack of expression or low abundance of expression might underlie the low efficiency of gene transfer in vivo. To test this hypothesis Pit2 protein expression may be measured by western blot in lung of animals with and without growth factor treatment. Pit2 protein should be detectable in both control samples and growth factor treated lungs. Using the same antibody, the pulmonary cell types expressing Pit2 can be localized by immunohistochemistry (Bosch et al., 1998).

Effects of epithelialpolarity on gene transfer efficiency. The airway epithelium is a polarized cell population. It was hypothesized that the apical surface, which serves as a barrier against infection in vivo, may impede gene transfer by retroviral vectors. This may be tested in vivo as follows. Primary cultures of differentiated rat tracheal epithelial cells can be grown at the air-liquid interface. This allows epithelia to differentiate into a tight epithelial sheet which closely mimics the in vivo airways. Growth factor is then added to the culture media 24 h prior to gene transfer to stimulate epithelial cell proliferation. After stimulation, β-gal retrovirus is applied to the apical or basolateral surface at an MOI of ~20 and incubated for 4 h at 37° C. For basolateral transduction, the cell culture inserts are turned over and the viral mixture is placed on the underside of the insert for 1 h, then the insert are re-placed in the upright position. Three days later the β-gal expression was evalutated with X-gal histochemistry. It is expected that growth factor will stimulate robust proliferation of cultured rat tracheal epithelia.

EXAMPLE 6

Feline Immunodeficiency Virus Vectors Persistently Transduce Non-dividing Airway Epithelia and Corect the CF Defect Methods Culture of Human Airway Epithelia Airway epithelial cells were obtained from surgical polypectomies or from trachea and bronchi of lungs for organ donation. Cells were isolated by enzyme digestion as previously described (Zabner et al., 1996). Freshly isolated cells were seeded at a density of $5\times10^5$ cells/cm$^2$ onto collagen-coated, 0.6 cm$^2$ diameter Millicell polycarbonate filters (Millipore Corp., Bedford, Mass.). The cells were maintained at 37° C. in a humidified atmosphere of 7% $CO_2$ and air. Twenty-four hours after plating, the mucosal media was removed and the cells were allowed to grow at the air-liquid interface (Zabner et al., 1996). The culture medium consisted of a 1:1 mix of DMEM/Ham's F12, 5% Ultroser G (Biosepra SA, Cedex, France), 100 U/ml penicillin, 100 µg/ml streptomycin, 1% nonessential amino acids, and 0.12 U/ml insulin.

Representative preparations from all cultures were scanned by EM and the presence of tight junctions confirmed by transepithelial resistance measurements (resistance>1000 Ohm×cm$^2$). All preparations used in the study were well differentiated and only well differentiated cultures>2 wk old were used in these studies. Previous studies show that differentiated epithelia in this model are multilayered and consist of ciliated cells (cytokeratin 18 positive), secretory cells containing granules that are reactive to goblet and mucous cell specific antibodies, and basal cells positive for cytokeratin 14 (Zabner et al., 1996; Yamaya et al., 1992).

Drugs and Chemicals

Aphidicolin (20 µg/ml) (Sigma Chemical, St. Louis, Mo.) was applied to cells for 24 hr before retroviral transduction to arrest cell growth in G1/S phase (Poeschla et al., 1998). To inhibit retroviral reverse transcriptase, 5 µM 3'-azido-3' deoxythymidine (Zidovudine or AZT, Burroughs Wellcome, N.C.) was added at the time of viral transduction.

Vector Production

The preparation of second generation FIV vector system was previously reported (Johnston et al., 1999). Plasmid constructs consist of an FIV packaging construct with a deletion in the env gene and mutations in vif and orf2, an FIV vector construct expressing either the cytoplasmic E. coli β-galactosidase or CFTR genes, and an envelope expressing plasmid in which an internal human cytomegalovirus (CMV) early gene promoter directs transcription of the vesicular stomatitis virus G protein (VSV-G). In the packaging construct, the CMV promoter substituted for the FIV 5' LTR, and the 3' LTR was replaced with the SV40 poly A. In the FIV β-gal and CFTR vectors, a CMV/FIV LTR hybrid promoter substituted for the FIV 5' LTR. Frameshift mutations were created in orf1 (vif) and orf2 to create a second generation vector. In the vector constructs, the CMV promoter directed β-galactosidase expression (FIV-βgal), while the MuLV LTR promoter directed expression of the human CFTR cDNA (FIV-CFTR) (Rommens et al., 1989.

VSV-G pseudotyped FIV vector particles were generated by transient transfection of plasmid DNA into 293T cells plated one day prior to transfection at a density of $2.8\times10^6$ cells/10 cm diameter culture dish as described previously (Johnston et al., 1999). Briefly, three plasmid co-transfections were performed using a 1:2:1 molar ratio of the FIV packaging construct, FIV vector construct (β-galactosidase or CFTR transgencs) and VSV-G envelope expressing plasmid. Forty two hr to 48 hr after the start of transfection, the supernatant was collected and filtered through a 0.45 µm pore Nalgene filter and stored at −70° C. Co-transfection of the three plasmids into 293T cells produced titers of ~10$^6$ cfu/ml crude supernatant. The vector was concentrated by centrifugation for 16 hr at a speed of 7,000×g (SW 28 rotor, Beckman L-70 Ultracentrifuge) at 4° C. The pellet was resuspended in 0.2–0.3 ml of lactose buffer (19.5 mM TRIS, 37.5 mM NaCl, and 40 mg/ml lactose, pH 7.3). Each βgal preparation was titered on NIH 3T3 cells by limiting dilutions; final titers of ~$5\times10^7$–$10^9$ cfu/ml were obtained.

To titer the FIV-CFTR vector, a PCR™-based assay system was developed. Triplicate wells of HT-1080 target cells ($3\times10^5$ cells) were transduced with serial dilutions of crude or processed FIV vector preparations in the presence of 4 µg/ml Polybrene. Twenty-four hours after transduction fresh media was applied and the cells were allowed to grow for an additional 24–48 hr. Each of the triplicate samples were washed with 1×PBS, incubated with 2.5 mls of lysis buffer [100 mM Tris, pH 8, 5 mM EDTA, 0.2% SDS, 100 mM NaCl, 100 µg/ml proteinase K (Qiagen, Valencia, Calif.)] at 37° C. for 2 hr, and the DNA precipitated by the addition of 3 mls isopropyl alcohol and gentle shaking for 1 hr at room temperature. Genomic DNA pellets were washed with 70% ethanol, resuspended in 500 µls TE buffer, and total genomic DNA quantified by staining with Hoechst dye H33258 (Hoechst) and compared directly against calf thymus DNA standards using the CytoFluor II fluorometer (PerSeptive Biosystems, Framingham, Mass.). 100 ngs of each genomic DNA sample was subjected to automated PCR™ (50 µl volume) employing a PE ABI Prism 7700 system (Perkin-Elmer Corp., Norwalk, Conn.) and a synthetic oligonucleotide primer set directed against FIV packaging signal sequences to yield an 80-bp product The resulting fluorescence was detected and provector copy number titer expressed as transduction units/ml (TU/ml). Titers of $4.6\times10^9$ to $9.7\times10^8$ TU/ml were obtained in 2 preparations.

Gene Transfer

In vitro. Differentiated human airway epithelial cells (2 to 4 wk in culture) were used for gene transfer studies (Zabner et al., 1996). To transduce epithelia, the FIV vector was mixed with cell culture medium to make a final volume of 100 µl (MOI~10). This mixture was applied to either the apical surface or the basal surface. To perform gene transfer from the basal surface, the culture inserts were turned over and the viral mixture was added to the bottom of the filter membrane for 1 hr. To enhance retroviral transduction from the apical surface, the FIV vector was mixed at a 1:1 (vol/vol) ratio with 12 mM EGTA HEPES/saline solution (pH 7.3), and the mixture was applied to the apical surface for 4 hr as previously reported for MuLV-based retroviral vectors (Wang, 1998). Polybrene (8 µg/ml) was included in the transduction solutions.

Others previously reported that adenovirus infects human airway epithelia through the basolateral side by a fiber-dependent mechanism (Walters et al., 1999). To study the persistence of recombinant FIV-mediated correction of CFTR Cl current, the inventors compared it to that of recombinant adenovirus. The vector Ad2/CFTR-16 contains the CFTR cDNA driven by the CMV promoter and was previously described (Scaria et al., 1998). The inventors applied 50 MOI of Ad2/CFTR-16 in a volume of 25 µl to the bottom of the Millicell filter. After 30 min the epithelia were rinsed thoroughly and resumed to the culture dish. Epithelia were studied at intervals for the life of the culture (90–180 days).

Because of reports of protein transfer or pseudotransduction with concentrated AAV and retroviral vectors (Liu et al., 1996; Alexander et al., 1997), a control study was perfommed. At the time of addition of the FIV-βgal vector/EGTA solution to the apical surface, cells were treated- with AZT to inhibit the retroviral reverse transcriptase enzyme. AZT treated cells showed no significant expression of vector encoded product, confirming that the transduction with FIV vector under these study conditions was not due to protein transfer.

In vivo. For tracheal gene transfer adult New Zealand white rabbits were anesthetized with 32 mg/kg ketamine, 5.1 mg/kg xylazine and 0.8 mg/kg acepromazine intramuscularly. Using sterile technique, a ventral midline incision was made, exposing the trachea for tracheotomy. A ~1.5 cm tracheal segment cephalad to the tracheotomy was isolated, and cannulated on each end with PE 330 tubing (Clay Adams, Becton Dickinson). The tracheal segment was first rinsed and then filled with a solution of 12 mM EGTA in water for 30 to 60 min. The EGTA solution was removed, and replaced with 300 µl of FIV-βgal vector (titer $1-5 \times 10^8$ cfu/ml). The vector solution was left in place for 45 min then the cannulae were removed, the incisions closed, and animals were allowed to recover. Five days or 6 wk later, animals were sacrificed, and the tissues studied for β-galactosidase expression. For lower airway gene transfer, rabbits were anesthetized and a small PE50 catheter passed via the trachea until it lodged in a subsegmental bronchus. 200–600 µl of FIV-βgal vector formulated in hypotonic buffer with 6 mm EGTA or BAPTA was instilled. Five days later, animals were sacrificed and the tissues studied for β-galactosidase expression.

Tissue Histochemistry

β-galactosidase expression. Epithelial cells were fixed with 2% paraformaldehyde/PBS solution for 20 min and rinsed with PBS 3× for 5 min each. X-gal staining solution was added at 37° C. for 4 hr to overnight as previously described (McCray et al., 1995). Millicell membranes stained with DAPI were examined en face microscopically or embedded in paraffin and examined in cross section for β-galactosidase expression. The percentage of β-gal positive cells was determined by counting a minimum of 1000 cells from representative enface views of each treated cell culture insert.

Figure 4A:
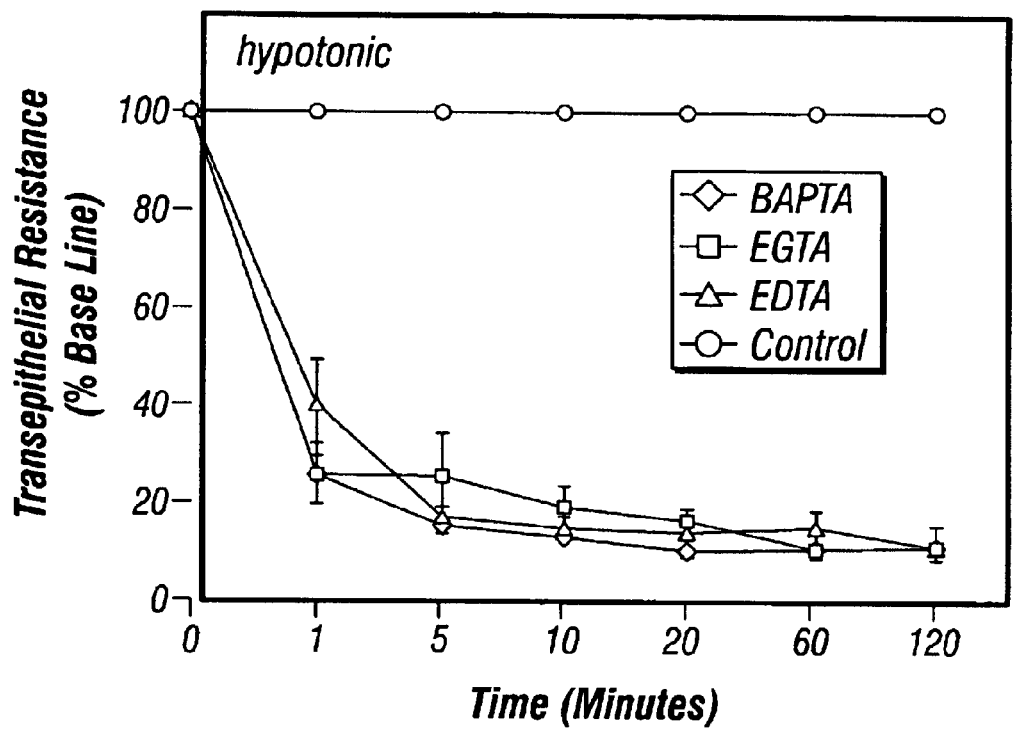

Rabbit airway and lung tissues were fixed in 2% parafomaldehyde/PBS overnight. Following X-gal staining and en face examination, tissues were embedded in paraffin, and sections were cut for histological examination. Sections were counter-stained with nuclear fast red or hematoxylin and eosin. To determine the percentage of βgal expressing cells in each 1.5–2 cm tracheal specimen, serial sections were cut every 20 µm and>50 slides examined from each trachea. To quantify gene transfer to rabbit low airways the blue tissue areas of the X-gal stained lungs (as shown in FIG. 4A) were dissected, embedded in paraffin, and 8 µm serial sections cut at 40 µm intervals. The percentage of βgal positive cells in lower airway tissues was quantified by cell counting. β-galactosidase expressing cells were also categorized by the size of the airway in which expression was noted (>750 µm, 500–750 µm, 250–500 µm, 0–250 µm) using a calibrated eyepiece reticle. To identify the cell types expressing β-galactosidase standard morphologic criteria were used. Transgene expressing cells were identified by their physical characteristics: 1) ciliated cells are columnar cells with cilia, 2) goblet cells are columnar cells containing secretory granules, 3) basal cells are basally located cuboidal cells having no contact with the mucosal surface, 4) intermediate cells are columnar cells in the lower half of the epithelium having no contact with the lumen, 5) Clara cells are non-ciliated, columnar to cuboidal surface cells that are more prevalent in the distal airways, and 6) alveolar type II cells are cuboidal, "corner" cells of the alveolar epithelium.

Evaluation of Transepithelial CFTR Cl Current

For measurement of transepithelial bioelectric properties, CF epithelia were mounted in Ussing chambers and studied 3, 13, 30, 60, 90 and 180 days following gene transfer as previously described (Zabner et al., 1996). Epithelia were bathed in symmetrical solutions containing (in mM): NaCl 135, $K_2HPO_4$ 2.4, $KH_2PO_4$ 0.6, $CaCl_2$ 1.2, $MgCl_2$ 1.2, dextrose 10, HEPES 5, at pH 7.2, 37° C. and gassed with 1000% $O_2$. The mucosal solution was similar, substituting NaCl with 135 mM sodium gluconate. Short-circuit current (ISC) was measured under baseline conditions or following the sequential addition of amiloride (10 µM), cAMP agonists (10 µM forskolin and 100 µM IBMX), and bumetanide (100 µM). The cAMP-stimulated Isc ($Isc_{(IBMX/Forsk)}$) is the increase in current after basolateral addition of cAMP agonists (10 µM forskolin plus 100 µM 3-isobutyl 1-methylxanthine, IBMX). Data from each study were normalized to the mean $Isc_{(IBMX/Forsk)}$ seen 3 days after infection. CF airway epithelia were genotyped, and were compound heterozygotes for the ΔF508 mutation (ΔF508/-, ΔF508/1717-16-A).

Results

FIV vectors transduce non-dividing airway epithelia in vitro. Based on previous literature (Fuller et al., 1984; Thomas and Roth, 1994) as well as our own studies with MuLV (Wang et al., 1998; Wang et al., 1999), the inventors suspected that the receptors for VSV-G pseudotyped FIV vectors were only expressed on the basolateral surface of airway epithelia. Indeed, when the inventors applied VSV-G pseudotyped FIV vector expressing β-galactosidase (FIV-βgal) to the apical surface, no gene transfer occurred. In contrast, application of the vector solution to the basolateral surface transduced the epithelia. The inventors hypothesized that if epithelial tight junctions were opened, FIV vector particles would have a better chance to interact with cell surface receptors and gain entry when applied epically. When the epithelial sheet was scratched with a pipette tip before applying vector to the apical surface, gene transfer occurred along the area where the cells were mechanically disrupted. Thus, if receptors were made accessible, gene transfer was achieved with VSV-G pseudotyped FIV vectors.

To demonstrate that FIV vectors transduce non-dividing epithelia, the inventors performed studies in the presence or absence of aphidicolin-induced growth arrest. As the inventors found previously that calcium chelation with EGTA and hypotonic solutions disrupted tight junctions and facilitated gene transfer with epically applied MuLV vectors (Wang et al., 1998; Wang et al., 1999), a similar approach was used with the FIV vector. When FIV-βgal was formulated with 6 mM EGTA in hypotonic buffer (MOI~10), gene transfer from the apical surface was greatly enhanced. Approximately 17% of epithelia growth-arrested with aphidicolin were transgene positive 3 days following transduction, while ~20% of epithelia in control media were transduced (FIG. 1). Previous studies showed that ~5% of cells are proliferating in this model as assayed by BrdU histochemistry (Wang et al., 1998). The EGTA solution alone had no effect on cell proliferation as assayed by BrdU histochemistry. Thus when allowed access to receptors, FIV vectors effectively transduced non-dividing airway cells.

FIV Vectors Coding for CFTR Persistently Correct the CF Cl Transport Defect

Based on the above results in normal human airway epithelia, the inventors hypothesized that recombinant FIV vectors expressing the human CFTR cDNA would complement the Cl-transport defect in well-differentiated CF epithelia For these studies the inventors used primary organotypic cultures of human airway epithelia from CF patients for the following reasons. Primary cultures of differentiated human CF airway epithelia recaptitulate several important aspects of in vivo airway epithelial biology and CF disease.

Cells cultured in this fashion morphologically resemble the human airways in vivo (Zabner et al., 1996 and Yanaya et al., 1992). Similar to the in vivo human airways, they are relatively resistant to transduction by both viral and non-viral vectors applied to the apical surface (Wang et al., 1998; Zabner et al., 1996; Zabner et al., 1995; Duan et al., 1998). They manifest the electrolyte and liquid transport defects characteristic of CF (Yamaya et al., 1992; Zabner et al., 1998). Importantly, unlike the long term survival and minimal evidence of lung disease reported for CFTR null mice or mice with specific human CFTR mutations (McCray et al., 1999; Zeiher et al., 1995; O'Neal et al., 1993; Colledge et al., 1995; Kent et al., 1996; Snouwaert et al., 1995), cultured human CF epithelia show an increased susceptibility to bacterial infection (Smith et al., 1996).

Figure 2A:
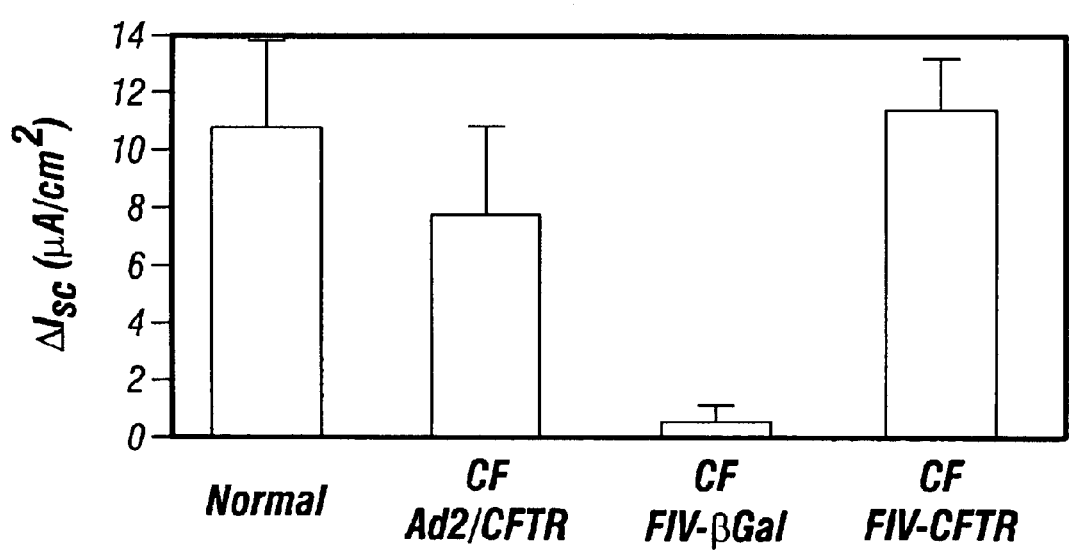
Figure 2B:
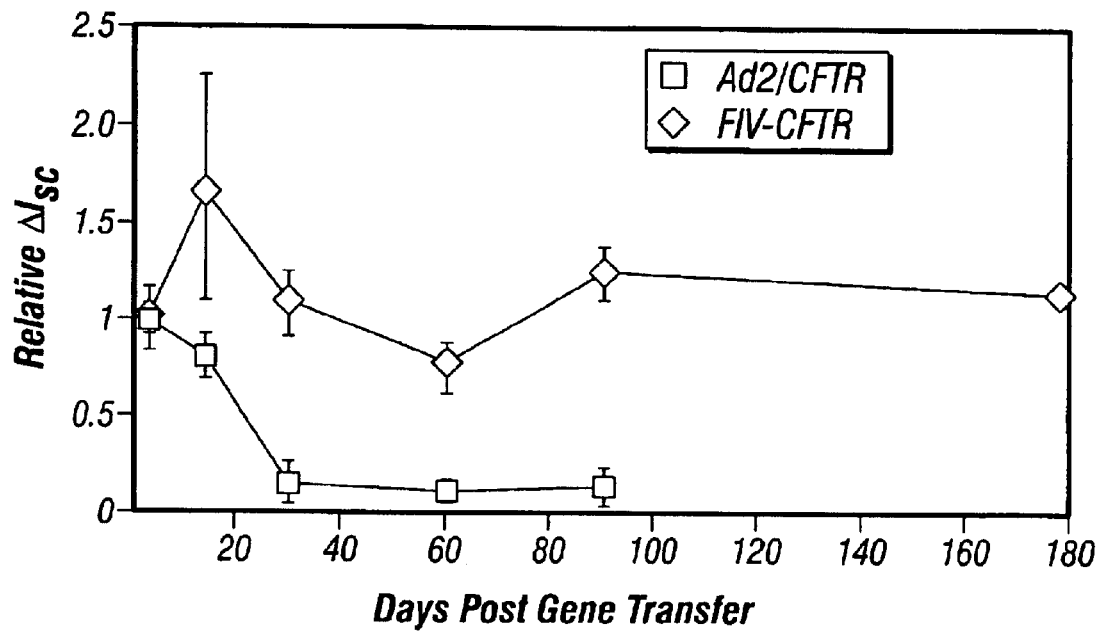

Tracheal epithelia were transduced in vitro from the apical surface with FIV encoding the CFTR cDNA (FIV-CFTR). Correction of the CFTR Cl-transport defect was assayed by measuring the change in short-circuit current in response to cAMP agonists ($\Delta Isc_{(IBMX/Forsk)}$), from 3 days to 6 months following gene transfer (FIG. 2). CF epithelia transduced with FIV-CFTR or adenovirus expressing CFTR uniformly demonstrated Cl-secretion in response to cAMP agonists, while control cells treated with FIV-βgal showed no response (FIG. 2A). The Cl-secretory responses in the corrected cells (FIG. 2A and FIG. 2B) were similar to those measured in normal airway epithelia (FIG. 2A and FIG. 2B). In cells transduced with adenovirus, $\Delta Isc_{(IBMX/Forsk)}$ gradually declined over time in culture. In contrast, the net $\Delta Isc_{(IBMX/Forsk)}$ in FIV transduced cells remained stable (FIG. 2B). In one FIV-CFTR transduced culture that remained viable for 6 months, cAMP-activated Cl current persisted at similar levels as day 3 (FIG. 2B).

FIV vectors transduce airway epithelia in vivo. The inventors hypothesized that FIV vectors might also effectively transduce airway epithelia in an intact animal if VSV-G receptors were accessible. The inventors used a similar protocol of tight junction disruption to test FIV vectors in vivo. Following EGTA pretreatment, FIV-βgal vector was applied to the luminal surface of the trachea in anesthetized normal adult rabbits. Five days later, the tissues were removed and studied for β-galactosidase expression. Cells throughout the epithelium expressed the transgene. The transduction efficiency was 4.8±5.6% (mean±SE, range: 1–14%, n=4). The treated epithelia appeared intact, without evidence of injury or inflammatory cell infiltrates. Of note, basal cells, intermediate cells and both ciliated and non-ciliated surface cells expressed β-galactosidase. Previous studies in several species have shown that the mitotic labeling indices for cells other than basal cells are very low (<1%) in adult airway epithelia (Shami and Evans, 1991). These studies suggest that FIV vectors effectively transduce both dividing and non-dividing cells in the mature airway epithelium in vivo. In the absence of EGTA formulation, there was no gene transfer.

CF lung disease begins in the small airways. To target the intrapulmonary airways a small catheter was passed transracheally into the peripheral airways and hypotonic/EGTA fomnulated FIV-βgal vector was instilled. This approach allowed the vector solution to be concentrated within a relatively small area. The inventors uniformly noted focal areas of gene transfer in the lung 5 days later. When serial sections of tissue were studied, epithelia expressing legal were noted throughout the segment where virus was instilled, from cartilaginous bronchi with diameters>750 μm out to the alveoli. The percentage of transgene expressing cells across all airway sizes was 4.9±2.2% (mean±SE, range: 2.6–10.3%, n=12). β-galactosidase expression occurred more frequently in the smaller airways than the larger airways as might be expected with the method of vector introduction (FIG. 3). Importantly, the morphology of the transduced airway epithelia appeared normal and all cell types of the lower airways were transduced, including proposed progenitors such as basal cells, non-ciliated surface cells (Clara cells) and alveolar type II cells. Vector instillation without the EGTA formulation resulted in no significant gene transfer.

FIV gene transfer to airway epithelia persists in vivo. Animals treated with FIV-βgal vector intratracheally were evaluated 6 wk post gene transfer for persistence of gene expression. In contrast to the results at day 5, larger clusters of β-galactosidase positive cells were rioted on both the en face views and the cross sections of the trachea, suggesting that targeted cells clonally expanded over time. The inventors noted β-galactosidase expressing cells throughout the epithelium. The percentage of βgal expressing cells was 2.5±2% (mean±SE, range: 0.4 to 5.4%, n=4). When compared to the level of expression at 5 days, this change was not significant (p=0.5 by t-test). Transduced cell types included basal cells, non-ciliated surface cells, ciliated surface cells, cells containing mucus granules, intermediate cells, and rarely, epithelia of submucosal glands. As noted at the 5 day time point, the epithelial morphology appeared normal.

EXAMPLE 7

Increasing Epithelial Junction Permeability Enhances Gene Transfer to Airway Epithelia In Vivo Materials and Methods Culture of Human Airway Epithelia Airway epithelial cells were obtained from surgical polypectomies or from trachea and bronchi of lungs removed for organ donation. Cells were isolated by enzyme digestion as previously described (Yamaya et al., 1992; Zabner et al., 1996). Freshly isolated cells were seeded at a density of $5 \times 10^5$ cells/cm$^2$ onto collagen-coated, 0.6 cm$^2$ diameter Millicell polycarbonate filters (Millipore Corp., Bedford, Mass.). The cells were maintained at 37° C. in a humidified atmosphere of 7% $CO_2$ and air. Twenty-four hours after plating, the mucosal media was removed and the cells were allowed to grow at the air-liquid interface (Yamaya et al., 1992). The culture medium consisted of a 1:1 mix of DMEM/Ham's F12, 5% Ultroser G (Biosepra SA, Cedex, France), 100 U/ml penicillin, 100 μg/ml streptomycin, 1% nonessential amino acids, and 0.12 U/ml insulin. Epithelia were tested for transepithelial resistance and for morphology by scanning electron microscopy. Studies were performed on differentiated cells (≧2 wk old).

Reagents

Chemicals. All chemicals were of reagent grade quality. The sources of the calcium chelators used were as follows: EGTA (Fisher Scientific, #S311-500), EDTA (Ambresco, Solon, Ohio, #0732-50G), and BAPTA (Sigma, St. Louis, Mo., #A4926).

Growth factors. To stimulate cell proliferation in studies using MuLV, recombinant lumen keratinocyte growth factor (KGF, Chiron Technologies Center for Gene Therapy, Inc., San Diego, Calif.) was applied to the basal medium of differentiated airway cells at a concentration of 100 ng/ml as described previously (Wang et al., 1998). After 24 hr of KGF stimulation, differentiated airway cells were subjected to different conditions.

Recombinant viral vectors. Two amphotropic enveloped MuLV vectors were used in these studies. DA-βgal expressing a cytoplasmic β-galactosidase reporter was prepared at Chiron Technologies-Center for Gene Therapy, Inc., as described previously (Jolly, 1994). The packaging cell line producing amphotropic nuclear-targeted β-galactosidase retrovirus (TA-7βgal) was provided by Francois-Loic Cosset and virus was prepared in the University of Iowa Gene Transfer Vector Core (Kitten et al., 1997). Titers for the TA-7βgal vectors were typically $1-5\times10^8$ cfu/ml by blue cell counts on 3T3 cells, while titers for the DA-βgal vector were $5\times10^8$ cfu/ml. All the reporter genes were driven by the LTR promoter. Polybrene was included in all infection mixtures at a final concentration of 8 μg/ml. Adenoviral vectors expressing nuclear targeted β-galactosidase (Ad5CMVntβ-gal or Ad5RSVntβ-gal) were produced in the Gene Transfer Vector Core.

Transduction of Epithelial Cells with Recombinant Retroviruses

Fully differentiated airway epithelia were stimulated to divide using 100 ng/ml KGF. Twenty four hours later, retrovirus (MOI~20) was combined with hypotonic (~40 mmol/kg), or isotonic (~220 mmol/kg) solutions containing EGTA, EDTA or BAPTA. The final concentration of each chelator was specified in individual studies. The viral solutions were applied to the apical surface of the epithelia and incubated for different times as described. The transduced epithelia were cultured for 3 days. Transgene expression was detected using a X-gal histochemical method.

Histochemistry

Epithelial cells were fixed with 2% paraformaldehyde/PBS solution for 20 min and were rinsed with PBS twice for 10 min each. X-gal solution was applied and was incubated at 37° C. for 4 hr to overnight as previously described (Wang et al., 1998). Cells grown on filter membranes were examined microscopically en face for β-galactosidase expression. The epithelial cells were counter-stained with DAPI to identify nuclei. For each epithelia, over 1000 total cells were scanned and the percentage of blue cells was calculated.

Rabbit airway and lung tissues were fixed in 2% paraformaldehyde/PBS overnight. Following X-gal staining and en face examination, tissues were embedded in paraffin, and sections were cut for histological examination. Sections were counter-stained with nuclear fast red.

Measurement of Transepithelial Resistance

Differentiated epithelial cells were treated with 100 ng/ml KGF for 24 hr. Different concentrations of each calcium chelator in HEPES/HCl (pH 7.4) or in isotonic HEPES/saline (pH 7.4) buffer were mixed with vector buffer and applied to the apical surface for times as specified (Wang et al., 1998). Transepithelial resistance was measured with an Ohmmeter (EVOM; World Precision Instruments, Inc. Sarasota, Fla.) by adding cell culture media to the apical surface and the values were compared to untreated controls.

Confocal Microscopy

Ten micromoles of CMFDA (5-chloromethylfluorescein diacetate; Molecular Probes, Eugene, Oreg.) were added to the basal medium overnight to label cells (Knecht and Shelden, 1995; Stewart and Deacon, 1995). 100 nm latex beads ($1\times10^9$ particles, Sigma, St. Louis, Mo.) were mixed with 12 mM hypotonic EGTA solution at a 1:1 ratio. The suspension was applied to the apical surface of KGF-stimulated epithelia for 1 hr. The epithelia were then washed with PBS 4–5 times for 20 min and then fixed in 4% paraformaldehyde/PBS for 20 min. The cell filter membranes were removed, mounted on slides, and examined under a confocal microscope (MRC 1024, Bio-Rad).

Electron Microscopy

Transmission electron microscopy was used to study cell morphology following treatment with a 6 mM EGTA in hypotonic buffer for 1 hr. Differentiated human airway epithelia were fixed in 2.5% glutaraldehyde (0.1 M sodium cacodylate buffer, pH 7.4) overnight at 4° C., and then post-fixed with 1% osmium tetroxide for 1 hr. Following serial alcohol dehydration, samples were embedded in Eponate 12 (Ted Pella, Inc., Redding, Calif.). Sectioning and post-staining were performed using routine methods (see "Electron Microscopy: Principles and Techniques for Biologists," Jones and Bartlett Publishers, Sudbury, Mass., 1998). Samples were examined under a Hitachi H-7000 transmission electron microscope.

Disruption of Tight Junctions in the Airway Epithelium in vivo

Rabbit studies. The transepithelial electrical potential difference across the rabbit tracheal epithelium ($V_t$) was measured using a modification of previously described methods (Zabner et al., 1996). The reference electrode was a subcutaneous needle connected with sterile normal saline solution to a silver/silver chloride pellet. Adult New Zealand white rabbits (n=4/group) were anesthetized with 32 mg/kg ketamine, 5.1 mg/kg xylazine and 0.8 mg/kg acepromazine intramuscularly and placed with the head in the dependent position. An exploring electrode (pediatric size 8 Teflon-coated latex double lumen Foley catheter, modified Ruseh, Inc., Duluth, Ga.) was inserted into the tracheal lumen via a tracheotomy incision. One lumen of the catheter was filled with sterile normal saline solution and was connected to a silver/silver chloride pellet. Voltage was measured with a voltmeter connected to a strip chart recorder. The catheter was then left in that position for the entire recording period. The solutions were administered through the second lumen in the following order: 1) Normal saline for 5 min; 2) Sterile water with 10 mM EGTA for 10 min; 3) Normal saline with 10 mM EGTA for 5 min; and 4) Normal saline with 10 mM EGTA plus 100 μM amiloride for 5 min. Measurements of $V_t$ were read by two investigators who were blinded to the treatment received. There wre no discrepancies in readings of greater than 2 mV between the investigators. Disruption of epithelial junctions was assessed by detecting a fall in nasal $V_t$ after perfusion with the chelator, and by the loss of amiloride-sensitive $V_t$ after perfusion with the chelator solution.

Human studies. The $V_t$ across the nasal epithelium was measured in 6 volunteers using previously described methods (Zabner et al., 1996). The protocol followed was identical to that described above for the rabbit studies. The rubber catheter was introduced into the nostril under telescopic guidance, and the side holes of the catheter were placed under the inferior nasal turbinate 6 cm from the most caudal aspect of the columella. The catheter was then left in that position for the entire recording period. The solutions were administered through the second lumen in the following order: 1) Normal saline for 5 min; 2) Sterile water with 10 mM EGTA or 10 mM EDTA for 10 min; 3) Nommal saline with 10 mM EGTA or 10 mM EDTA for 5 min; and 4) Normal saline with 10 mM, EGTA or 10 mM EDTA plus 100 AM amiloride for 5 min. Measurements of $V_t$ were read by two investigators who were blinded and wvere checked by a third investigator if there was a discrepancy of more than 2 mV. Disruption of epithelial junctions was assessed by detecting a fall in nasal $V_t$ after perfusion with the chelator, and by the loss of amiloride-sensitive $V_t$ after perfusion with the. chelator solution.

Gene transfer to the rabbit tracheal epithelium In Vito. Adult New Zealand white rabbits were anesthetized with 32 mg/kg ketamnine, 5.1 mg/kg xylazine and 0.8 mg/kg acepromazine intramuscularly. Using sterile technique, a ventral midline incision was made, exposing the trachea for tracheotomy. A ~1.5 cm tracheal segment cephalad to the tracheotomy was isolated, and cannulated on each end with PE 330 tubing (Clay Adams, Becton Dickinson). The tracheal segment was first rinsed and then filled with a solution of 12 mM EGTA in water for 45 min. The EGTA solution was removed, and as replaced with 300 μl of retrovirus (titer $3 \times 10^9$ cfu/ml) or adenovirus (titer $1 \times 10^{10}$ pfu/ml) vector. In control animals, saline was substituted for water and EGTA treatment. Animals that received the MuLV retrovirus were pretreated with keratinocyte growth factor (KGF) prior to gene transfer to stimulate epithelial proliferation (~5 mg/kg intravenously and 600 μg via nasal instillation for 3 doses given 36, 24 and 12 hr preceding the procedure) (Wang et al., 1998; Wang et al., 1999). The vector solution was left in place for an additional 45 min. and then the cannulae were removed, the incisions closed, and animals were allowed to recover. Three days later, animals were sacrificed, and the tissues studied for β-galactosidase expression.

Results

Calcium Chelation Opens Epithelial Junctions

In previous reports, the inventors documented that retrovirus-mediated gene transfer (Wang et al., 1998; Wang et al., 1999) and adenoviral-mediated gene transfer (Walters et al., 1999) to differentiated airway epithelia occurred preferentially from the basolateral surface. The inventors hypothesized that $Ca^{2+}$ chelation enhanced gene transfer from the apical surface by opening epithelial junctions and allowing vector access to the basolateral membrane. To address this hypothesis, the inventors used fluorescent latex beads (100 nm) as a marker for the virus to follow particle deposition in the presence of a $Ca^{2+}$ chelator. Fluorescent beads suspended in a hypotonic 6 mM EGTA solution were applied to the apical side of differentiated human airway cells for 1 hr. After washing, the epithelial cells were fixed and examined. In control cells without EGTA treatment, no beads were observed in the paracellular space or within the cell cytoplasm but they were noted on the apical surface. EGTA treatment caused a widening of the intercellular spaces and facilitated deposition of beads in the paracellular space. These results show that $Ca^{2+}$ chelation opens epithelial junctions and allows 100 nm-sized particles access to the basolateral surface.

Transmission electron microscopy was used to examine directly the effect of $Ca^{2+}$ chelation and hypotonic conditions on the epithelial junctional complex. EGTA-treated airway cells developed a widened intercellular gap. The space, estimated to be ~500 nm across, was approximately five times larger than a retroviral or adenoviral particle. In contrast, control epithelia maintained tight intercellular junctions with no visible gap. These studies suggest that vector formulation with a hypotonic buffer and a $Ca^{2+}$ chelator allows viral particles to percolate through the intercellular space and transduce airway epithelia at the susceptible basolateral membrane.

Vector-mediated Gene Transfer to Airway Cells in vitro is Enhanced by Calcium Chelation The inventors evaluated the ability of three different chelators to enhance gene transfer to airway cells. EGTA has a higher affinity for $Ca^{2+}$ over $Mg^{2+}$ ($>10^5$ fold) and its $Ca^{2+}$ binding efficiency is pH sensitive. In contrast, BAPTA binds $Ca^{2+}$ in an acidic environment, and has faster $Ca^{2+}$ binding and release kinetics. In contrast to BAPTA and EGTA, EDTA has a broader spectrum of divalent cation binding. The preference of EDTA for $Ca^{2+}$ is 100-fold greater than that for $Mg^{2+}$. Vector solutions were formulated with 6 mM final concentrations of the chelators in a hypotonic buffer and then applied to the apical surface for 4 hr. Gene transfer was examined three days later. In control cells, the vectors were applied in an isotonic buffer without a $Ca^{2+}$ chelator. In the absence of $Ca^{2+}$ chelation, no gene transfer occurred for either retrovirus (amphotropic MuLV) or adenovirus vectors. All three chelators enhanced gene transfer with retroviral vectors from the apical surface similarly. Also, gene transfer with adenoviral vectors was enhanced by formulation with $Ca^{2+}$ chelators. For MuLV, the efficiency of gene transfer declined as the chelator concentration was increased above 6 mM. Thus, hypotonic formulation and $Ca^{2+}$ chelation greatly enhances gene transfer when viral vectors are applied to the apical surface.

Figure 4B:
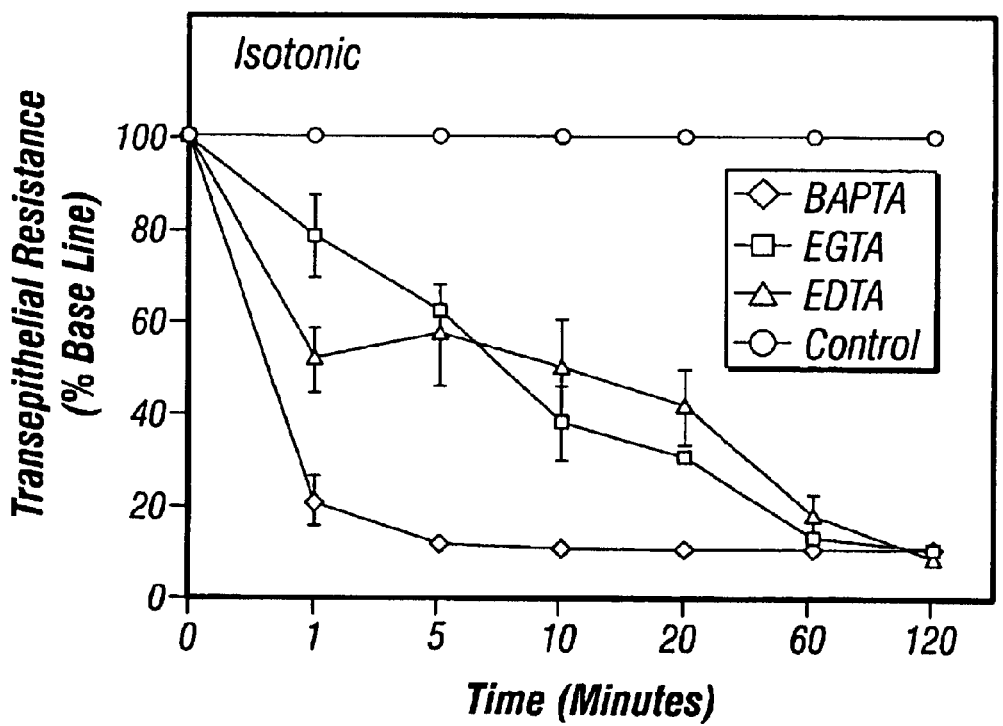

Calcium Chelation Under Hypotonic Conditions Enhances Gene Transfer More Quickly Than Isotonic Conditions To understand whether the tonicity of the vector solution affects epithelial permeability and gene transfer efficiency, hypotonic (40 mmol/kg) or isotonic (220 mmol/kg) solutions of 6 mM EGTA, EDTA or BAPTA were added to the MuLV vector buffer and applied to the apical surface of differentiated airway epithelial cells pre-treated with KGF. At specific time intervals, transepithelial resistance ($R_1$) was measured using an Ohmmeter. As shown in FIG. 4A and FIG. 4B, all three hypotonic chelator solutions reduced $R_1$ to <20% of control values within the initial 10 min. Isotonic chelator solutions showed more variable results. Sixty minutes were required for isotonic EGTA or EDTA to decrease $R_1$ to ~20% of the controls. In contrast, isotonic BAPTA quickly dropped $R_1$, similar to the hypotonic solutions.

Figure 4C:
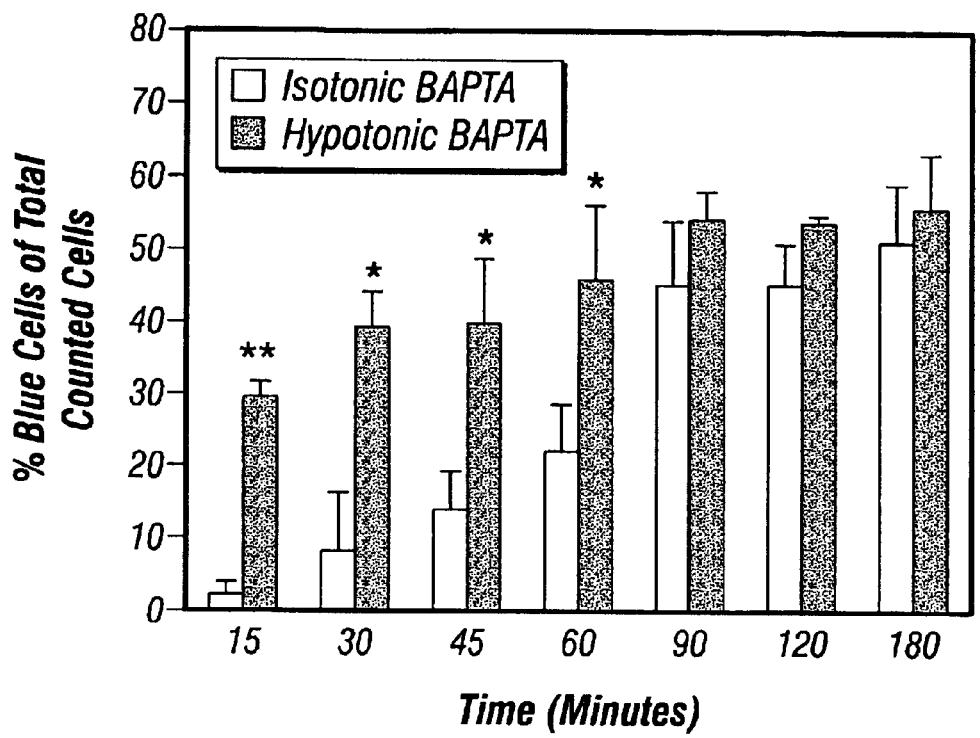
Figure 4D:
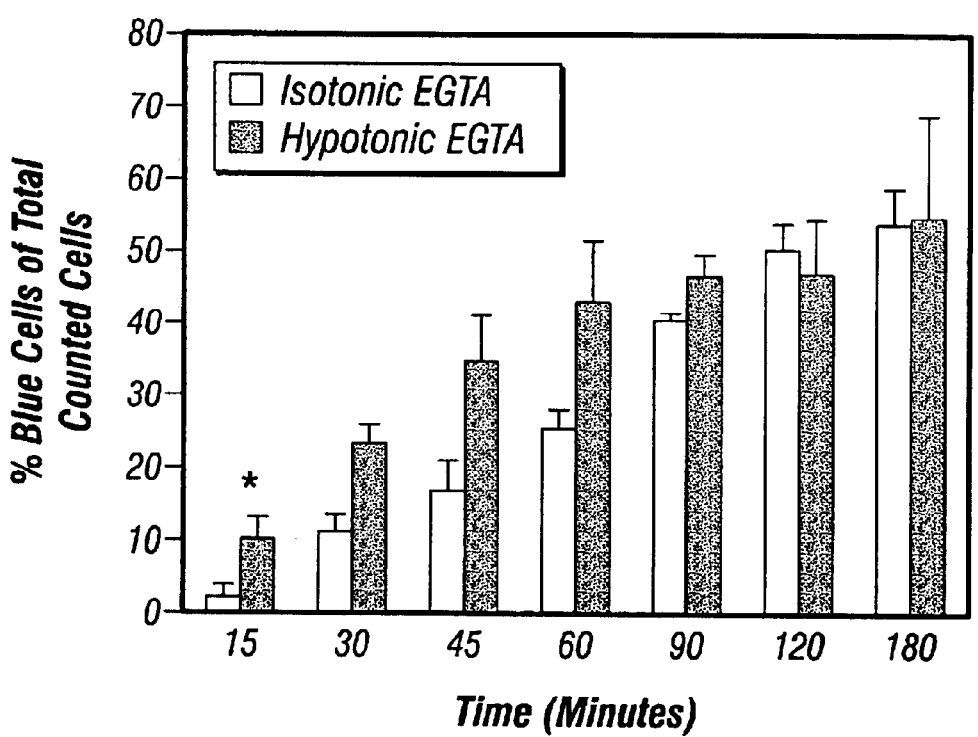

The inventors next evaluated the time course of retroviral gene transfer with EGTA and BAPTA. The inventors focused these studies on EGTA and BAPTA because of their specificity for $Ca^{2+}$ over other divalent cations. In the presence of either 6 mM EGTA or 6 mM BAPTA, airway cells were transduced for periods of 15 to 180 min before removing the vector solution. Three days later, transgene expression was assessed by X-gal histochemistry and quantified by blue cell counting. FIG. 4C and FIG. 4D show that maximal gene transfer with hypotonic preparations occurred by 1 hr. This effect was most apparent with BAPTA. In contrast, greater than 1 hr was required for maximal gene transfer with isotonic vector solutions. These studies show that the prompt fall in $R_1$ noted with hypotonic chelation conditions is associated with gene transfer, requiring a shorter vector incubation period. Based on these results, the inventors elected to use the combined conditions of a hypotonic solution and a $Ca^{2+}$ chelator in vivo.

EGTA Treatment Disrupts the Transepithelial Voltage ($V_t$) and Amiloride-sensitivity in Rabbit Tracheal Epithelia and Human Nasal Epithelia in vivo The in vitro studies show that treatment of epithelia with a $Ca^{2+}$ chelator in a hypotonic buffer opens epithelial junctions and enhances gene transfer to differentiated human airway epithelia The inventors wondered if such a formulation strategy could also be applied in vivo. It is not technically feasible to measure $R_1$ in vivo. However, measurements of transepithelial voltage ($V_t$) can provide an assessment of $R_1$ because as $R_1$ falls to zero, $V_t$ will also decrease to zero. The inventors first measured the bioelectric responses of the tracheal epithelium in anesthetized rabbits to perfusion with a hypotonic/EGTA solution and saline containing EGTA. As shown in FIG. 5A, perfusion of the trachea with a hypotonic solution containing 10 mM EGTA and subsequent treatment with saline and 10 mM EGTA caused a significant fall in $V_t$. Following hypotonic/EGTA treatment, amiloride had no effect on $V_t$. In contrast, control tracheas perfused with saline exhibited stable baseline voltages and the anticipated fall in $V_t$ in response to perfusion with amiloride. The simplest interpretation of these studies is that the hypotonic/EGTA treatment opened epithelial junctions in vivo, by reducing $R_1$ and thereby $V_t$.

The in vitro results in cultured airway epithelia and in vivo studies in rabbits suggest that it is possible to increase epithelial permeability by combined hypotonic/EGTA treatment. Such vector formulation strategies may be useful for gene transfer to epithelia for the treatment of diseases in humans. To learn if $Ca^{2+}$ chelation also opens epithelial junctions in human airway epithelia in vivo, the inventors performed studies using the nasal epithelium as a model. The baseline nasal $V_t$ was recorded, then the epithelium was sequentially perfused with EGTA in water, EGTA in saline, followed by EGTA in saline with amiloride. The nasal voltage was measured throughout the study. In control studies, the same protocol was performed on a different day in the same subjects, omitting the water treatment and EGTA from the perfusate. Subjects did not experience any adverse effects, and could not tell the difference between perfusion with the EGTA solution or saline.

As shown in FIG. 5B, when subjects received the $H_2O$/EGTA treatment followed by EGTA in saline perfusion, there was a significant decrease in the $V_t$. Following EGTA treatment, essentially no amiloride-sensitive $V_t$ remained. In control studies, $V_t$ remained stable with solution changes and there was a significant fall in $V_t$ with amiloride treatment (FIG. 5B, left hand panel). In contrast, EGTA treatment caused a significant fall in nasal $V_t$ and loss of amiloride-sensitive $V_t$ compared with control conditions. Similar results were obtained when EDTA was substituted for EGTA in the perfusion protocol. Thus, treatment with $Ca^{2+}$ chelators increased human nasal epithelial permeability, consistent with the in vitro findings.

Vector Formulation with a Hypotonic Buffer and EGTA Enhances Gene Transfer in vivo The inventors next tested whether conditions that appeared to open epithelial junctions in vivo also facilitated gene transfer. Following pretreatment with 12 mM EGTA in water, a retroviral or adenoviral vector was applied to the luminal surface of the trachea in anesthetized normal adult rabbits. Animals receiving MuLV were pretreated with KGF to stimulate. epithelial proliferation (Wang et al., 1998; Wang et al., 1999; Zsengeller et al., 1999; Ulich et al., 1994; Housley et al., 1994). Three days later, the tissues were removed and studied for β-galactosidase expression. Both vectors transduced cells throughout the tracheal epithelium, including non-ciliated and ciliated surface cells, intermediate cells and basal cells. The number of β-galactosidase expressing cells was qualitatively greater in the adenovirus treated rabbits than for those that received retrovirus. This result may reflect, in part, the titer dependence of gene transfer, and the requirement for cell division by MuLV-based vectors. Tracheas that received either viral vector without EGTA and hypotonic buffer treatment showed no evidence of gene transfer.

EXAMPLE 8

Polarity Influences the Efficiency of Recombinant Adeno-associated Virus Infection in Differentiated Airway Epithelia Materials and Methods
Primary Culture of Human Bronchial Epithelia Primary human airway epithelial cells were collected by enzymatic digestion of bronchial samples from lung transplants as previously described (Kondo et al., 1991; Zabner et al., 1996). Isolated airway primary cells were seeded at a density of $5 \times 10^5$ cells/cm$^2$ onto collagen-coated Millicell-HA culture inserts (Millipore, Bedford, Mass.). Primary cultures were grown at the air-liquid interface for more than 2 wk, at which time differentiation into a mucociliary epithelium occurs. The culture medium, used to feed only the basolateral side of the cells, contained 49% Dulbecco's modified Eagle's medium (DMEM), 49% Ham's F12, and 2% Ultraser G (BioSepra, Cedex, France).

Production of rAAV and Transduction of Polarized Airway Epithelial Cells

Recombinant AAV virus was produced by a $CaPO_4$ co-transfection protocol and was purified through three rounds of isopycnic cesium chloride ultracentrifuigation, as previously described (Duan et al., 1997). The proviral plasmid, pCisAV.GFP3ori, was used to generate rAAV (AV.GFP3ori), which encoded the enhanced green fluorescent protein (EGFP) reporter gene under the transcriptional control of the cytomegalovirus (CVM) enhancer/promoter and simian virus 40 (SV40) polyadenylation signal (Duan et al., 1998). Recombinant viral stocks were heated at 58° C. for 60 min to inactivate contaminating helper adenovirus. Typical yields were $1 \times 10^9$ particles/µl, determined on the basis of DNA slot-blot hybridization assays against plasmid standards. The level of adenoviral contamination, as based on a second reporter assay for the recombinant adenovirus used for propagation (Ad.CMVAlkphos) (Duane et al., 1997), was less than 1 functional particle per $1 \times 10^{10}$ DNA particles of rAAV. Viral preparations were evaluated for the contamination of wild type AAV (wtAAV) by immunocytochemical staining of AV.GFP3ori/Ad.CMVLacZ (Duan et al., 1998)-coinfected 293 cells with anti-Rep antibodies (American Research Products, Belmont, Mass.). All rAAV stocks demonstrated an absence of Rep immunoreactivity when $1 \times 10^{10}$ rAAV particles were used for infection. Transfection with Rep/Cap-encoding plasmids served as controls for antibody staining of Rep protein. Virus was dialyzed in phosphate-buffered saline (PBS) prior to application on primary airway cultures. For infections from the apical surface of the airway cells, 5 µl of AV.GFP3ori was mixed with 100 µl of culture medium and applied directly onto the apical compartment of Millicell inserts. During apical infection, the basolateral side of the Millicell was continuously bathed in culture medium. Gene transfer to the basal side was performed by inverting Millicell inserts and applying viral vector to the bottom of the supporting filter membrane in a 100-µl volume for 2 hr. Subsequently, Millicell inserts were returned to the upright position, in the continued presence of the original viral load plus an additional 300 µl of medium. For both apical and basolateral infections, rAAV-containing medium was removed after 24 hr and replaced with either fresh culture medium (for the basal side) or exposed to air (for the apical side).

Viral binding and Entry Assays

Tritium-labeled AV.GFP3ori was prepared according to a previously published protocol (Summerford and Samulski, 1998) with several modifications. Briefly, [methyl-$^3$H]thymidine (specific activity: 3159 GBq/mmol)(NET-027Z; NEN Life Science Products, Boston, Mass.) was added to the cell culture medium at a final concentration of 1 µCi/ml at 7 hr posttransfection with pCisAV.GFP3ori and pRepCap plasmids and infection of Ad.CMVLacZ. $^3$H-labeled AV.GFP3ori was purified as described above. Typical yields were $3.6 \times 10^8$ particles/µl at a specific activity of $4 \times 10^{-7}$ cpm/virion. To assess the binding of rAAV to polarized bronchial epithelial cells, 100 µl of $^3$H-labeled rAAV.GFP (multiplicity of infection [MOI] of 60,000 particles/cell, with a total of $1.2 \times 10^4$ cpm, $3 \times 10^{10}$ particles) was applied to either the apical or basal surface, as described above, and incubated at 4° C. for 90 min. Combined binding/entry of rAAV into differentiated airway epithelia was measured in the same settings except that the cultures were incubated at 37° C. for 24 hr before they were harvested. These combined viral binding/entry assays were performed under infection conditions identical to those used for functional studies of rAAV transduction with transgene expression as an end point. After washing three times in PBS, cells were lysed in situ with 5 ml of Ready Safe liquid scintillation cocktail (Beckman Instruments, Fullerton, Calif.) at room temperature for 5 min and the radioactivity was quantitated in a scintillation counter. Calculation of the amount of bound and internalized rAAV particles was based on the known specific radioactivity of $^3$H-labeled virions.

Immunofluorescent Localization of Heparan Sulfate Proteoglycan

Localization of AAV type 2 receptor (membrane-associated heparan sulfate proteoglycan) was performed using fully differentiated bronchial primary cultures. Cells were fixed in 4% paraformaldehyde for 10 min followed by cryoprotection in 10, 20, and 30% sucrose prior to embedding in O.C.T. (optimal cutting temperature medium; Baxter, Warrendale, Pa.). Sections (8 μm) were postfixed in 4% paraformaldehyde for 15 min. The samples were then blocked in 20% goat serum-PBS for 20 min followed by incubation in a 1:200 dilution of rat and-heparan sulfate proteoglycan monoclonal antibody (Chemico International, Temecula, Calif.). Antigens were detected by indirect immunofluorescence using a 1:250 dilution of fluorescein isothiocyanate (F1TC)-conjugated goat anti-rat IgG (Jackson Immuno Research Laboratories, West Grove, Pa.). Nuclei were counterstained with propidium iodide (5 μg/ml). The specificity of the immunocytochemical staining was confirmed by competition studies performed by preabsorbing the primary antibody with either the specific competitor heparan sulfate (Sigma, St. Louis, Mo.) or a nonspecific competitor chondroitin sulfate C (Sigma), at a final concentration of 5 μg/ml for 8 hr at 4° C. before applying antibody to the sections. Immunostaining of the UV-irradiated cultures was performed at 24 hr after 25 J/m$^2$ UV exposure.

UV Irradiation, Hypotonic EGTA, and Keratinocyte Growth Factor Treatment

For the UV irradiation studies, Millicell inserts were put transiently into empty 100-mm tissue culture plates (apical side up) and exposed to 25 J/m$^2$ of UV light (254 nm). After irradiation, the Millicell inserts were quickly returned to plates containing Ultraser G culture medium on the basolateral side. Infections with rAAV were performed immediately following UV irradiation by application of 5×10$^9$ rAAV particles in 100 μl to either the apical or basolateral side of the support membrane as described above. Keratinocyte growth factor (KGF) treatment was performed at a final concentration of 100 ng/ml by addition to the basolateral culture medium for two sequential 24-hr incubations prior to AAV infection. Transient disruption of tight junctions was achieved by treating polarized cells with 3 mM EGTA in water for 10 min. After hypotonic EGTA treatment, cultures were washed twice with culture medium and infected with 5×10$^9$ rAAV particles in 100 μ it on either the apical or basolateral side of support membranes.

Measurement of Transepithelial Resistance

The transepithelial resistance of primary airway cultures was monitored with an ohm meter (EVOM; World Precision Instruments, Sarasota Fla.), as previously described (Wang et al., 1998). Briefly, after washing with 3 mM EGTA in H$_2$O, 400 μl of culture medium was added to the apical side of the cultured airway cells. Electrodes were placed in both the mucosal and serosal compartments of the Millicell inserts and the resistance across the epithelia was recorded.

Determination of Cell Proliferation by BrdU Staining

Identification of proliferating airway epithelial cells were performed using bromodeoxyuridine (BrdU) labeling reagents from Zymed Laboratories (South San Francisco, Calif.). Cells were treated with recombinant human keratinocyte growth factor (rKGF; Chiron, San Diego, Calif.) at 100 ng/ml for two consecutive days. The cells were then pulse labeled for 12 hr with a 1:100 dilution of the BrdU labeling reagent prior to fixation in 10% neutral buffered formalin. Histochemical staining of BrdU incorporation into nuclei was performed according to the manufacturer's instructions. Cells were counterstained with hematoxylin and the cell culture filters were examined by en face microscopy of the apical surface.

Assays for Receptor-independent Endocytosis with Nile Red Fluorescent Beads

Nile Red fluorescent beads (20-nm carboxylate-modified microspheres [FluoSpheresl; Molecular Probes, Eugene, Oreg.) were used to investigate receptor-independent endocytosis in polarized airway epithelial cultures. After dialysis in PBS overnight at 4° C., the Nile Red beads were diulted 1:100 with culture medium and alleged to either the apical or basal surface of airway cultures (with or without 25 J/m$^2$ UV irradiation) as described for rAAV infection studies. Millicell inserts were harvested at 5 min, 2 hr, 6 hr, 12 hr, and 24 hr following inoculation with fluorescent beads and washed with room temperature PBS three times. The extent of endocytosis was examined by either en face fluorescence (Leica DMR) or after fixation in 4% paraformaldehyde by confocal microscopy to capture perpendicular XZ section images (Nikon Optiphot, Bio-Rad MRC 1024).

Electron Microscopy

Fully differentiated airway epithelia grown on permeable filter supports (Millicells) were harvested for scanning electron microscopic analysis 24 hr following UV irradiation at 25 J/m$^2$. Control samples were from the same set of cultures, but were not exposed to UV iraadiadon. Samples were fixed in 2.5% glutaraldehyde in 0.1 M sodium cacodylate buffer (pH 7.2) and were then postfixed with 1% OsO$_4$. Dehydration was performed with a graded series of ethanol followed by drying with hexamethyldisilazane. Samples were mounted on Cambridge-style stubs and sputter coated with gold/palladium prior to examination by scanning electron microscopy using a Hitachi S-4000 FEGSEM electron microscope.

Results

Polarity of rAAV Transduction in Differentiated Airway Epithelia

Studies have suggested inefficient in vivo gene transfer to the airway using adenoassociated viral vectors (Halbert et al., 1997). Several potential barriers to in vivo rAAV delivery to the airway may explain these findings. These include a low level of viral receptor at the apical surface of epithelial cells, limited endosomal processing of virus and translocation to the nucleus, and/or insufficient cellular machinery for the conversion of the single-stranded viral genome to functional double-stranded, forms capable of expressing transgenes. To understand better the nature of barriers affecting rAAV-mediated gene transfer to airway, polarized cultures of human airway epithelial cells grown at the air-liquid interface were utilized (Kondo et al., 1991; Zabner et al., 1996). The goal of this study was to investigate whether features associated with airway epithelial cell polarity may be responsible for limiting rAAV transduction in the airway.

Initial studies testing the efficiency of rAAV gene transfer from the apical and basolateral sides of polarized airway epithelial cultures demonstrated a greater than 200-fold higher level of transduction following basolateral infection with rAAV. When AV.GFP3ori virus (MOI of 10,000 particles/cell) was applied to the apical membrane of polarized cultures, 0.4±0.2 GFP-positive cells/×10 field were detected at 40 days postinfection (FIG. 6). In contrast, when an equivalent amount of virus was administered to the basolateral surface of the polarized epithelial cultures, the level of transgene expression was 103±6 GFP-positive cells/×10 field at 40 days postinfection. Transgene expression was detected at low levels beginning at 4 days postinfection and gradually increased to peak levels between 30 and 40 days, at which time the studies were terminated (FIG. 6). In support of the observed polarity of infection in this in vitro model, it was also noted that infection of fully differentiated human bronchial xenograft epithelia demonstrated a similar refractivity to infection with rAAV at MOIs equal to 1000 particles/cell.

To understand better whether the observed efficiency of basolateral infection in polarized bronchial airway cultures was higher than that in proliferating nonpolarized primary bronchial cultures, the inventors analyzed rAAV transduction in 80% confluent primary bronchial epithelial cells grown on tissue culture plastic. MOIs (10,000 particles/cell) and viral stocks used for infection were identical for both airway culture systems. After infection of nonpolarized undifferentiated airway cultures, GFP transgene expression was seen as early as 24 hr and reached peak level by 4 days postinfection. Approximately 10% of cells were transduced at 4 and 8 days postinfection. This level is in contrast to the maximal transduction efficiency in differentiated polarized airway cultures of approximately 1% at 40 days postinfection following basolateral infection and 0.005% following apical infection. Furthermore, the onset of transgene expression in differentiated polarized cultures was much slower than that seen in proliferating nonpolarized airway cells. Such findings suggest that certain aspects associated with epithelial differentiation and/or polarity significantly affect both the kinetics and extent of rAAV transduction in the airway.

Several mechanisms could explain the remarkable difference between apical and basolateral infection efficiency in polarized airway cultures, including (1) artificial effects caused by nonspecific binding of rAAV viral particles to the filter membrane used in polarized cultures, (2) inhibitory factors in airway surface fluid that either directly inactivate or indirectly inhibit the infectious capacity of the AAV, (3) partitioning of cellular membrane receptors for AAV in a polarized fashion to basolateral membranes, and/or (4) a higher abundance of intracellular factors involved in AAV transduction (such as asymmetrical endocytosis and/or nuclear transport of virus) in the basal compartments of polarized airway epithelial cells. To test whether collagen-coated filters could serve as a reservoir for rAAV and arbitrarily enhance transduction from the basolateral surface, nonspecific attachment of rAAV particles to the transwell membrane was examined with $^3$H-labelled virus. Incubation of $^3$H-labeled AV.GFP3ori with empty (no cells) collagen-coated transwell inserts at 37° C. for 24 hr did nod result in a significant retainment of viral particles, as indicated by comparison with background counts from transwells incubated with medium alone (p>0.114).

To investigate the possible existence of inhibitory factors in airway fluid, the inventors next sought to determine whether airway secretions could affect AAV infectivity. In these studies, virus was preincubated with airway surface fluid for 4 hr at 37° C. prior to application on the basolateral side of polarized airway cultures. Since the volumne of the fluid collected from the air-liquid interface of in vitro polarized epithelial cultures was limited, the inventors chose to use airway secretdons collected from fully differentiated human bronchial xenografts (Zhang et al., 1998). Although it was reported that airway sputum represented a barrier to liposome-mediated gene transfer (Stern et al., 1998), no significant difference was obtained between virus incubated with either bronchial xenograft airway secretions or buffer controls (FIG. 7). This result suggests that inactivation of AAV infectivity by airway secretions does not represent a major obstacle for viral transduction from the apical membrane.

Transient Permeabilization of Epithelia Moderately Increases Gene Transfer from the Apical Surface To explore the mechanisms of epithelial polarity that might alter the efficiency of rAAV transduction in the airway, the inventors evaluated whether transient disruption of epithelial tight junctions could increase rAAV-mediated transgene expression following apical delivery. The inventors reasoned that if the lack of AAV transduction at the apical membrane was due to the asymmetric distribution of the viral receptor(s), the inventors would expect to see an increase in AAV transduction efficiency when the tight junction barrier was temporarily disrupted prior to viral infection. In support of this hypothesis, it has been demonstrated that temporary disruption of tight junctions resulted in significant increases in retrovirus-mediated gene transfer from the apical side of KGF-treated polarized epithelial cultures (Wang et al., 1998). Tight junctions are dynamic structures consisting of interwoven strands of proteins that anchor adjacent epithelial cells (Cereijido et al., 1998). A high extracellular calcium concentration is required to maintain the stability of tight junction complexes. Previous studies have demonstrated that transepithelial permeability through pericellular pathways can be reversibly regulated by hypotonic solutions and calcium-chelating agents such as EGTA (Bhat et al., 1993; Widdicombe et al., 1996). To test the hypothesis, polarized cultures of human bronchial epithelial cells were exposed to 3 mM EGTA-$H_2$O for 10 min at 37° C. on either the apical or basolateral sides prior to viral infection. This treatment resulted in an immediate, greater than 10-fold decease in the transepithelial resistance, which gradually recovered within 18 hr after removal of the hypotonic EGTA solution. These findings confirm previously reported effects of transient permeabilization of polarized airway epithelium by water applied to the mucosal surface (Bhat et al., 1993; Widdicombe et al., 1996). As shown in FIG. 8A, evaluation at 22–40 days postinfection demonstrated that the disruption of epithelial tight junctions increased rAAV transduction from the apical surface-by 7- to 10-fold in comparison with untreated controls. Despite this increase, the level remained 20-fold lower than the maximal levels of transgene expression observed following delivery of virus to the basolateral membrane. To exclude the possibility that the hypotonic EGTA treatment might affect cell viability and hence lower the level of transduction that could be achieved, morphologic examination of polarized primary cultures was performed 40 days after hypotonic/EGTA treatment. No significant differences were detected in the integrity of the monolayers by light microscopy. Furthermore, when polarized primary cultures were treated with hypotonic/EGTA solution on the basolateral membrane, and virus was subsequently delivered to the basal side of the epithelia, no significant differences were seen in the extent of rAAV. transduction (FIG. 8B). These results suggest that transient exposure of primary epithelial cultures to hypotonic/EGTA did not result in a significant loss of cell viability, which might indirectly decrease the capacity of cells to be productively infected by rAAV.

UV Irradiation Augments rAAV Transduction Only from the Apical Side of Polarized Airway Epithelial Primary Cultures It has been previously demonstrated that the rAAV transduction efficiency can be improved in both immortalized cell lines and nondividing primary cells by UV irradiation at dosages that do not significantly alter cell viability or proliferative capacity (Alexander et al., 1994; Ferrari et al., 1996). The mechanisms contributing to this increased transduction have been suggested to involve enhanced DNA repair pathways and/or single-strand to double-strand transformation of input AAV genomes. To this end, the inventors evaluated the effect of UV irradiation (25 J/m$^2$) prior to application of rAAV on either the apical or basolateral side of primary cultures. Similar dosages have been used by Alexander and colleagues (1994) to demonstrate UV-mediated increases in AAV transduction of stationary-phase primary human fibroblast cells. As shown in FIG. 3A, a 20- to 30-fold increase in transgene expression was observed by 40 days posttreatment, when virus was added to the apical surface after UV stimulation. This result consumed previous successes using UV to augment AAV transduction (Alexander et al., 1994; Ferrari et al., 1996). Interestingly, when AAV infection was performed on the basolateral side of UV-irradiated culture chambers, only a slight elevation in transduction at 4- and 8-day postinfection time points was seen. By 30 to 40 days postinfection, UV-irradiated cells demonstrated a 2-fold decrease in the efficiency of transgene expression as compared with untreated controls also infected from the basolateral side (FIG. 8B). These results suggest that UV irradiation is capable of modulating rAAV transduction in polarized airway primary cultures. However, the magnitude and direction of this modulation are different depending on the cellular surface of infection. Enhanced transduction from the apical side following UV exposure could be due to asymmetric entry and/or processing pathways of AAV in the basal and apical compartments.

Increased Abundance of Heparan Sulfate Proteoglycan at the Basal Surface of Polarized Airway Epithelia Correlates with Increased Viral Binding Membrane-associated heparan sulfate proteoglycan has been identified as a receptor for AAV-2 (Summerford and Samulski, 1998). To test whether the observed polarity of infection by rAAV is associated with the asymmetrical distribution of the viral receptor, the inventors evaluated the distribution of the membranebound heparan sulfate proteoglycan in polarized bronchial epithelial cultures. Heparan sulfate proteoglycan immunoreactivity was predominantly localized to the basal surface of the polarized culture. No immunoreactivity was seen on the lateral or apical surfaces of polarized epithelia. The specificity of antibody binding was demonstrated by the complete absence of immunoreactivity on tissue sections following preincubation of the anti-heparan sulfate proteoglycan antibody with free soluble heparan sulfate. In contrast, preincubation with a nonspecific competitor, chondroitin sulfate C, did not alter the immunolocalization pattern in tissue sections. Since UV irradiation at 25 J/m$^2$ significantly enhanced rAAV transduction from the apical surface of polarized airway epithelia (FIG. 8), the inventors hypothesized that UV exposure might also alter the partitioning of heparan sulfate proteoglycan to the apical surface. However, contrary to this initial hypothesis, UV irradiation did not alter the abundance of AAV receptor expression at the apical membrane. Furthermore, a significant decrease in heparan sulfate proteoglycan immunoreactivity was seen at the basal membrane following UV irradiation. This might account for the observed decrease in rAAV transduction from this surface.

To further expand our findings on AAV receptor localization, $^3$H-labeled rAAV was used to evaluate the extent of virus binding/uptake at apical and basolateral surfaces of polarized airway cultures. Viral binding was determined by apical or basolateral application of radiolabeled virus at 4° C. for 90 min. As shown in FIG. 9, the basolateral membrane of epithelia bound virus sevenfold more efficiently than the apical membrane. In studies performed to compare directly the combined efficiency of both viral binding and uptake under conditions similar to those used in reporter gene studies, the inventors compared the total amount of viral binding and internalization over a 24-hr period at 37° C. following both apical and basolateral application of virus. Interestingly, the number of viral particles bound and internalized under these conditions was indistinguishable from that seen in 4° C. binding studies (basolateral six- to sevenfold higher than apical). In summary, these results substantiate findings of basal membrane heparan sulfate proteoglycan immunoreactivity and suggest that polarized localization of the AAV receptor likely plays an important role in the efficiency of rAAV-mediated gene transfer. However, examination of UV-irradiated bronchial cultures failed to demonstrate a significant increase in rAAV binding/uptake from the apical membrane (FIG. 9). Taken together, results from AAV receptor localization and viral binding/uptake study suggest that enhancement of rAAV transduction following UV irradiation likely occurs through pathways independent of virus binding to its receptor. In support of additional receptor-independent pathways that might also limit rAAV transduction, it is also apparent that the six- to sevenfold difference in AAV binding/uptake between apical and basolateral membranes is insufficient to explain the observed 200-fold difference in rAAV transgene expression following infection from the basolateral and apical membranes.

Augmentation of Cellular Proliferation by KGF Leads to a Decrease in rAAV Transduction To investigate further other aspects of epithelial cell phenotype that might affect rAAV transduction in the airway, the inventors evaluated the relationship between cellular proliferation and the efficiency of rAAV infection in the model of the airway. Although some studies have identified the cell cycle as a major influence in rAAV transduction (Russell et al., 1994; Qing et al., 1998), transduction efficiency of nonmitotically active cells also seems to be dependent on the cell type. Often the kinetics of rAAV-mediated transgene expression can be affected by a variety of factors, including adenovirus coinfection, UV irradiation, and proliferative rate. Effects of the cell cycle on rAAV transduction are most notable in studies comparing confluent with proliferating cultures of primary fibroblasts or other contact growth inhibited cell lines (Russell et al., 1994; Halbert et al., 1995). Simnilar limitations have been observed for recombinant retroviral transduction. Several studies have demonstrated that exogenous treatment with KGF can increase cellular proliferation and retrovirally mediated gene transfer in polarized airway epithelia in vitro (Wang et al., 1998) and liver in vivo (Bosch et al., 1996). To determine whether growth factor-induced human airway epithelial cell proliferation would similarly enhance rAAV transduction in the model system, the inventors evaluated the effects of KGF on AAV infectivity. Sequential treatment of airway cultures with KGF resulted in significant increases in cell proliferation, as determined by BrdU incorporation. However, these increases in cellular proliferation did not increase the efficiency of rAAV transduction, regardless of whether the virus was applied to the apical or basolateral side. Moreover, long-term (40 day) gene expression was inhibited twofold by KGF treatment, following infection from the basal side of primary cultures. These results are discordant with the traditional dogma that enhanced cellular proliferation increases rAAV transduction. Several potential mechanisms could explain these findings, including targeting of rAAV to non-KGF-stimulated cells and/or KGF inhibition of cellular factors that are needed for rAAV transduction. In support of these observations, others have shown that cellular functions other than those involved in DNA replication might also be important for AAV-mediated gene transfer. This was evidenced by increased AAV transduction in the presence of a DNA synthesis inhibitor (Russell et al., 1995). Mitogenically active KGF is known to elicit a variety of cellular function changes, including cell proliferation, migration, and morphogenesis. The activity of KGF is mediated by its receptor, FGFR-2, which is a tyrosine kinase (Rubin et al., 1995). Interestingly, it was reported that inhibition of cellular tyrosine kineses augments transgene expression from AAV (Qing etal., 1997, 1998). Furthermore, the epidermal growth factor receptor (EGFR) has been demonstrated to be one potential candidate tyrosine kioase receptor mediating these effects. The potential involvement of FGFR and KGF in mediating similar affects on AAV transduction remains to be determined.

UV Irradiation Alters Apical Membrane Architecrure and Enchances Receptor-independent Pathways of Endocytosis To investigate mechanisms that might be responsible for the observed polarity in UV-induced rAAV transduction, the inventors evaluated the morphology of polarized epithelial primary cultures following UV irradiation of the apical surface, using scanning electron microscopy (SEM). UV (25 J/m$^2$) led to significant morphologic changes in the apical surfaces of polarized primary cultures by 24 hr postirradiation. The most notable changes included shortening and deformation of the microvillous architecture. Although the structure of the cilia was not significantly changed, ciliated cells were less frequently seen in UV-irradiated cultures. Despite these changes, the integrity of the epithelial monolayer appeared to be intact. These changes suggest a potential reorganization of the cytoskeleton at the apical membrane after UV irradiation. Since the polymerization of actin filaments plays an important role in endocytic processes and is also known to be negatively affected by UV, the inventors hypothesized that the observed enhancement of rAAV transduction from the apical membrane might be the result of modulated endocytosis and/or endosomal processing by W irradiation. However, studies evaluating $^3$H-labeled rAAV binding/internalization following UV exposure demonstrated no increase in virus binding at 4° C. or combined binding and uptake at 37° C. for 24 hr. This piece of evidence suggests that intracellular steps involving endocytic processes (distal to AAV binding and perhaps internalization at the apical membrane) might play an important role in limiting transducdon. Hence, the inventors investigated whether receptor-independent pathways of an docytosis were altered at the apical membrane following UV irradiation, using 20-nm fluorescent particles similar in size to AAV virions. In these studies, two significant findings were noted. First, the uptake of 20-nm Nile Red beads was much more efficient from basolateral as compared with apical membranes. Second, UV irradiation significantly enhanced uptake of Nile Red beads from the apical surface of polarized epithelia. Currently, the inventors have no definitive explanation for why receptor-independent pathways of endocytosis are enhanced from the apical surface while cumulative binding and uptake of rAAV over a 24-hr period demonstrated no enhancement following UV irradiation. However, it is reasonable to speculate that AAV receptors may be saturated with bound AAV at the apical membrane and that UV irradiation enhances the endocytosis of externalized receptor-bound virus and/or the rate of endosomal processing of internalized virus within the apical membrane compartment.

EXAMPLE 9

Methods

The optimal dose range for EGTA was determined on primary cultures of human airway epithelia Gene transfer efficiency with apical application of MuLV or FIV based retrovirus (MOI 10) or adenovirus (MOI 50) was determined over a range of EGTA concentrations from 0–96 mM. The vectors were diluted 1:1 (vol/vol) with a buffer consisting of water, 10 mM HEPES and the appropriate amount of EGTA. The vector formulation was left on the apical surface of the cells for 4 hrs, then removed. Gene transfer efficiency was evaluated 3 days later by X-gal staining for beta galactosidase expression.

In a related study, we evaluated the efficacy of an anti-E-cadherin antibody (50 ug/ml in apical solution) in decreasing transepithelial resistance and enhancing gene transfer.

Results

Retrovirus. For MuLV or FIV based retroviruses gene transfer scored as the percentage of blue cells, was greatest with EGTA concentrations of 6–12 mM. At higher or lower concentrations, the efficiency diminished.

Adenovirus. The results for adenovirus were essentially the same as for retrovirus.

E-caderin antibody. Within 1 hr of addition, the antibody caused the transepithelial resistance of airway cells to fall to essentially background levels (<10–20% of baseline). If the adenovirus vector solution (50 MOI in normotonic buffer) was added after antibody treatmnent for 4 hours, enhanced gene transfer was noted. If the antibody was mixed with the adenoviral vector and applied to the apical surface, gene transfer was noted also.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

References

The following references, to the extent that they provide exemplary procedural or other details supplementary to those set forth herein, are specifically incorporated herein by reference.

"Electron microscopy: principles and techniques for biologist," Jones and Bartlett Publishers, Sudbury, Mass., 1998.

Adamson and Bowden, *Lab. Invest.* 30:35–42, 1974.

Alexander, Russell, and Miller, "DNA-damaging agents greatly increase the transition of nondividing cells by adeno-associated virus vectors," *J. Virol.,* 68, 8282–8287, 1994.

Alexander, Russell, Miller, "Transfer of contaminants in adeno-associated virus vector stocks can mimic transduction and lead to artifactual results," *Hum. Gene Ther.,* 8:1911–1920, 1997.

Anderson and Itallie, *Am. J. Physiol.,* 269:G467–G475, 1995.

Anderson et al., Welsh, *Science,* 253:202–205, 1991.

Anderson, and Itallie, "Tight junctions and the molecular basis for regulation of paracellular permeability," *Am. J. Physiol,* 269:G467–G475, 1995.

Arap et al., *Cancer Res.,* 55:1351–1354, 1995.

Arcone, et al., *Nucl. Acids Res.,* 16(8): 3195–3207, 1988.

Ayers and Jeffery, "Proliferation and differentiation in mammalian airway epithelium," *Eur. Respir. J.,* 1:58–80, 1988.

Baichwal and Sugden, In: *Gene Transfer,* Kucherlapati R, ed., New York, Plenum Press, pp. 117–148, 1986.

Bartlett et al., *Proc. Nat'l Acad. Sci. USA,* 93:8852–8857, 1996.

Basak and Compans, *J. Virol.,* 63:3164–3167, 1989.

Bayle et al., *Hum. Gene Ther.,* 4:161–170, 1993.

Bedzyk etal., *J. Biol. Chem.,* 265:18615, 1990

Benvenisty and Neshif, Proc. Nat. Acad. Sci. USA, 83:9551–9555,1986.

Bhat et al., *Pharm. Res.,* 10:991–997, 1993.

Bhat, Toledo-Velasquez, Wang, Malanga, Ma, Rojanasakul, "Regulation of tight junction permeability by calcium mediators and cell cytoskeleton in rabbit tracheal epithelium," *Pharm. Res.,* 10:991–997, 1993.

Bingisser, Kaplan, Zollinger, Russi, "Whole-lung lavage in alveolar proteinosis by a modified lavage technique," *Chest,* 113:1718–1719, 1998.

Blan and Compans, *Virology,* 210:91–99, 1995.

Blomer et al., *J. Virol.* 71:6641–6649, 1997.

Bosch et al., "Proliferation induced by keratinocyte growth factor enhances in vivo retroviral-mediated gene transfer to mouse hepatocytes," *J. Clin. Invest.,* 98:2683–2687, 1996.

Bosch et al., *Hum. Gene Ther.* 9:1747–54, 1998.

Boucher, Jr., Bromberg, Gatzy, "Airway transepithelial electric potential in vivo: species and regional differences," *J. Appl Physiol.,* 48:169–176, 1980.

Bowles et al., *Hum. Gene Ther.,* 7:1735–1742, 1996.

Brown, Mellis, Wood, "Edetate sodium aerosol in pseudomonas lung infection in cystic fibrosis," *AJDC,* 139:836–839, 1985.

Burns et al., *Proc. Nat'l Acad. Sci. USA,* 90:8033–8037, 1993.

Bussemakers et al., *Cancer Res.,* 52:2916–2922, 1992.

Caldas et al., *Nat. Genet.,* 8:27–32, 1994.

Carey, Fabbroni, Lamb, "Expression of proliferating cell nuclear antigen in lung cancer: a systematic study and correlation with DNA ploidy," *Histopathology* 20:499–503, 1992.

Casey et al., *Oncogene,* 6:1791–1797, 1991.

Cereijido, Valdes, Shoshani, Contreras, "Role of tight junctions in establishing and maintaining cell polarity," *Annu. Rev. Physiol.,* 60:161–177, 1998.

Chan, Phipps, Gonda, Cook, Fulton, Young, Bautovich, "Regional deposition of nebulized hypodense nonisotonic solutions in the human respiratory tract," *Eur. Respir. J,* 7:1483–1489, 1994.

Chaudhary et al., *Proc. Nat'l Acad. Sci.,* 87:9491, 1990

Cheng et al., *Cancer Res.,* 54:5547–5551, 1994.

Cheung et al., *J. Biol. Chem.,* 268:6139–6146, 1993.

Chien, Foster, Douglas, Garcia, *J. Virol.,* 71:4564–4570, 1997.

Chowdhury et al., *Science* 254:1802–1805, 1991.

Chu, Tousignant, Fang, Jiang, Chen, Cheng, Scheule, Eastman, "Binding and uptake of cationic lipid:pDNA complexes by polarized airway epithelial cells," *Hum. Gene Ther.,* 10:25–36, 1999.

Clayson and Compans, *Mol. Cell Biol.,* 8:3391–3396, 1988.

Coffin, In: *Virology,* Fields et al., eds., Raven Press, New York,.pp. 1437–1500, 1990.

Colledge, Abella, Sothem, Ratcliff, Jiang, Cheng, MacVinish, Anderson, Cuthbert, Evans, 1995 "Generation and characterization of a ΔF508 cystic fibrosis mouse model," *Nature Genet.,* 10:445–452, 1995.

Collins, "Cystic fibrosis: Molecular biology and therapeutic implications," *Science,* 256:774–779, 1992.

Cook et al., *Cell,* 27:487–496, 1981.

Cosman, Nieves, Horton, Shen, Lindsay, "Effects of estrogen on response to edetic acid infusion in postmenopausal osteoporotic women," *J. Clin. Endocrinol. Metab.* 78:939–943, 1994.

Crystal et al., *Nature Genet.* 8:42–51, 1994.

Culver et al., *Science,* 256:1550–1552, 1992.

Denker, Nigam, "Molecular structure and assembly of the tight junction," *Am J Physiol,* 274:F1–F9, 1998.

Donahue et al., *J Exp Med;* 176(4): 1125–1135, 1992.

Drumm, Pope, Cliff, Rommens, Marvin, Tsui, Collins, Frizzell, Wilson, "Correction of the cystic fibrosis defect in vitro by retrovirus-mediated gene transfer," *Cell,* 62:1227–1233, 1990.

Duan, Fisher, Burda, and Engelhardt, "Structural and functional heterogeneity of integrated recombinant AAV genomes" *Virus Res.* 48, 41–56, 1997.

Duan, Sharma, Yang, Yue, Dudus, Zhang, Fisher, and Engelhardt, "Circular intermediates of recombinant adeno-associated virus have defined structural characteristics responsible for long term episomal persistence in muscle," J. Virol. 72, 8568–8577, 1998.

Duan, Yue, McCray Jr., Engelhardt, "Polarity influences the efficiency of recombinant adeno-associated virus infection in differentiated airway epithelia," *Hum. Gene Ther.* 9:2761–2776, 1998.

Dubensky et al., Proc. Nat. Acad. Sci. USA, 81:7529–7533, 1984.

Edelman and Crossin, *Annu. Rev. Biochem.,* 60:155–190, 1991.

Edelman, *Annu. Rev. Biochem.,* 54:135–169, 1985.

Engelhardt, Yankaskas, Wilson, *J. Clin. Invest.,* 90:2598–2607, 1992.

Evans et al., *Exp. Mol. Path.* 22:142–150, 1975.

Evans, Johnson, Stephens, Freeman, "Renewal of the terminal bronchiolar epithelium in the rat following exposure to $NO_2$ or $O_3$," *Lab. Invest.,* 35:246–257, 1976.

Evans, Moller, "Biology of airway basal cells," *Exp. Lung Res.,* 17:513–531, 1991.

Ferkol et al., *"FASEB J.,* 7:1081–1091, 1993.

Ferrari, Samulski, Shenk, and Samulski, "Second-strand synthesis is a rate-limiting step for efficient transduction by recombinant adeno-associated virus vectors," *J. Virol.* 70, 3227–3234, 1996.

Flotte, Afione, Conrad, McGrath, Solow, Oka, Zeitlin, Guggino, Carter, "Stable in vivo expression of the cystic fibrosis transmembrane conductance regulator with an adeno-associated virus vector," *Proc. Natl. Acad. Sci. USA,* 90:10613–10617, 1993.

Ford and Terzaghi-Howe, *Ex. Cell Res.* 198:69–77, 1992.

Forster and Symons, *Cell,* 49:211–220, 1987.

Foulds, *J. Chronic Dis.,* 8:2–37, 1958.

Frixen et al., *J. Cell Biol.,* 113:173–185, 1991.

Fuller, von Bonsdorff, Simons, "Vesicular stomatitis virus infects and matures only through the basolateral surface of the polarized epithelial cell line, MDCK," *Cell,* 38:65–77, 1984.

Furuse, Fujita, Hiiragi, Fujimoto, Tsukita, "Claudin-1 and -2: Novel integral membrane proteins localizing at tight junctions with no sequence similarity to occludin," *J. Cell Biol.,* 141:1539–1550, 1998.

Furuse, Hirase, Masahiko, Nagafuchi, Yonemura, Tsukita, "Occludin: a novel integral membrane protein localizing at tight junctions." *J. Cell Biol.,* 123:1777–1788, 1993.

Furuse, Sasaki, Fujimoto, Tsukita, "A single gene product, claudin-1 or -2, reconstitutes tight junction strands and recruits occludin in fibroblasts," *J. Cell Biol.,* 143:391–401, 1998.

Gerlach et al., *Nature (London),* 328:802–805, 1987.

Ghosh and Bachhawat, In: Liver Diseases, Targeted Diagnosis and Therapy Using Specific Receptors and Ligands. Wu et al., eds., Marcel Dekker, New York, pp. 87–104, 1991.

Giancotti and Ruoslahti, *Cell,* 60:849–859, 1990.

Goldman, Lee, Yang, Wilson, "Lentiviral vectors for gene therapy of cystic fibrosis," *Hum. Gene Ther.,* 8:2261–2268, 1997.

Gomez-Foix et al., *J. Biol. Chem.,* 267:25129–25134, 1992.

Gonzalez-Zulueta et al., *Cancer Research,* 55(20):4531–4535, 1995.

Gossen and Bujard, *Proc. Nat'l Acad. Sci. USA,* 89:5547–5551, 1992.

Gossen et al., *Science,* 268:1766–1769, 1995.

Graham and Prevec, In: *Methods in Molecular Biolog: Gene Transfer and Expression Protocol,* E. J. Murray, ed., Humana Press, Clifton, N.J., 7:109–128, 1991.

Green, Jones, "Desmosomes and hemidesmosomes: structure and function of molecular components," *FASEB J,* 10:871–881, 1996.

Grubb, Pickles, Ye, Yankaskas, Vick, Engelhardt, Wilson, Johnson, Boucher, "Inefficient gene transfer by adenovirus vector to cystic fibrosis airway epithelia of mice and humans," *Nature,* 371:802–806, 1994.

Grunhaus and Horwitz, *Seminar in Virology,* 3:237–252, 1992.

Gumbiner, "Breaking through the tight junction barrier," *J. Cell Biol,* 123:1631–1633, 1993.

Halbert, Aitken, Miller, "Retroviral vectors efficiently transduce basal and secretory airway epithelial cells in vitro resulting in persistent gene expression in organotypic culture," *Hum. Gene Ther.,* 7:1871–1881, 1996.

Halbert, Alexander, Wolgamot, and Miller, "Adeno-associated virus vectors transduce primary cells much less efficiently than immortalized cells," *J. Virol.* 69, 1473–1479, 1995.

Halbert, Standaert, Aitken, Alexander, Russell, and Miller, "Transduction by adeno-associated virus vectors in the rabbit airway: Efficiency, persistence, and readministration," *J. Virol.* 71, 5932–5941, 1997.

Halbert, Standaert, Wilson, Miller, "Successfiil readministration of adeno-associated virus vectors to the mouse lung requires transient immunosuppression during the initial exposure," *J. Virol.,* 72:9795–9805, 1998.

Han et al., *Proc. Nat'l Acad. Sci. USA* 92:9747–9751, 1995.

Hartmann, "Review Feline immunodeficiency virus infection: an overview," *Vet. J.,* 155:123–137, 1998.

Hatzoglou, Moorman, Lamers, *Somat. Cell Mol. Genet.,* 21:265–278, 1995.

Herman et al., *Cancer Research,* 55(20):4525–4530, 1995.

Hersdorffer et al., *DNA Cell Biol,* 9:713–723, 1990.

Herz and Gerard, *Proc. Nat'l Acad. Sci. USA,* 90:2812–2816, 1993.

Hollstein et al., *Science,* 253:49–53, 1991.

Housley, Morris, Boyle, Ring, Biltz, Tarpley, Aukerman, Devine, Pierce, "Keratinocyte growth factor induces proliferation of hepatocytes and epithelial cells throughout the rat gastrointestinal tract," *J. Clin. Invest.,* 94:1764–1777, 1994.

Hussussian et al., *Nature Genetics,* 15–21, 1994.

Inayama, Hook, Brody, Cameron, Jetten, Gilmore, Gray, Nettesheim, "The differentiation potential of tracheal basal cells, *Lab. Invest.,* 58(6):706–717, 1988.

Irwin et al., *J. Virol.,* 68:5036–5044, 1994.

Janowitz, Schumacher, Swobodnik, Kratzer, Tudyka, Wechsler, "Transhepatic topical dissolution of gallbladder stones with MTBE and EDTA. Results, side effects, and correlation with CT imaging," *Digestive Diseases and Sciences,* 38:2121–2129, 1993.

Jarnigan, Davis, Bromberg, Gatzy, Boucher, "Bioelectric properties and ion transport of excised rabbit trachea," *J. Appl. Physiol.,* 55:1884–92, 1983.

Johnson and Hubbs, "Epithelial progenitor cells in the rat trachea," *Am. J. Respir. Cell Mol. Biol.* 3:579–585, 1990.

Johnson, Mewshaw, Friedmann, Boucher, Olsen, "Effect of host modification and age on airway epithelial gene transfer mediated by a murine leukemia virus-derived vector," *J. Virol.,* 72:8861–8872, 1998.

Johnson, Olsen, Sarkadi, Moore, Swanstrom, Boucher, "Efficiency of gene transfer for restoration of normal airway epithelial function in cystic fibrosis," *Nature Genet.* 2:21–25, 1992.

Johnston, Gasmi, Lim, Elder, Yee, Jolly, Campbell, Davidson, Sauter, "Minimum requirements for efficient transduction of dividing and nondividing cells by feline immunodeficiency virus vectors," *J. Virol.,* 73:4991–5000, 1999.

Joki, et al., *Human Gene Ther.,* 6:1507–1513, 1995.

Jolly, "Viral vector systems for gene therapy," *Can. Gene Ther.,* 1:51–64, 1994.

Joyce, *Nature,* 338:217–244, 1989.

Kafri, Blomer, Peterson, Gage, Verrna, "Sustained expression of genes delivered directly into liver and muscle by lentiviral vectors," *Nat. Genet. I.,* 17:314–317, 1997.

Kageyama, et al., *J. Biol. Chem.,* 262(5):2345–2351, 1987.

Kamb et al., *Science,* 264:436–440, 1994.

Kaneda et al., *Science,* 243:375–378, 1989.

Kaplan, George, Pennington, Keyes, Johnson, Wadsworth, Smith, "Humoral and cellular immune responses of non-human primates to long-term repeated lung exposure to Ad2/CFTR-2," *Gene Ther.* 3:117–127, 1996.

Kasahara, Dozy, Kan, *Science* 266:1373–1376, 1994.

Kato et al., *J. Biol. Chem.,* 266:3361–3364,1991.

Kent, Oliver, Foskett, Fmdova, Durie, Forstner, Forstner, Riordan, Percy, Buchwald, "Phenotypic abnormalities in long-term surviving cystic fibrosis mice," *Pediatr. Res.,* 40:233–241, 1996.

Kim and Cook, *Proc. Nat'l Acad. Sci. USA,* 84:8788–8792, 1987.

Kitten, Cosset, Ferry, "Highly efficient retrovirus-mediated gene transfer into rat hepatocytes in vivo," *Hum. Gene Ther.,* 8:1491–1494, 1997.

Knecht, Shelden, "Three-dimensional localization of wild-type and myosin II mutant cells during morphogenesis of Dictyostelium," *Dev. Biol.*, 170:434–444, 1995.

Knowles et al., *N. Engl. J. Med.* 333:823–831, 1995.

Kondo, Finkbeiner, Widdicombe, "Simple technique for culture of highly differentiated cells from dog tracheal epithelium," *Am J Physiol.*, 263:L105–L117, 1991.

Le Gal La Salle et al., *Science*, 259:988–990, 1993.

Lee et al., *Science*, 235:1394–1399, 1987.

Leigh, Kylander, Yankaskas, Boucher, "Cell proliferation in bronchial epithelium and submucosal glands of cystic fibrosis patients," *Am. J. Respir. CellMol. Biol.*, 12:605–612, 1995.

Levrero et al., *Gene*, 101:195–202, 1991.

Lidor et al., *Am J Obstet Gynecol*, 177(3):579–585, 1997.

Lin and Guidotti, *J. Biol. Chem.*, 264:14408–14414, 1989.

Liu, Winther, Kay, "Pseudotransduction of hepatocytes by using concentrated pseudotyped vesicular stomatitis virus G glycoprotein (VSV-G)moloney murine leukemia virus-derived retrovirus vectors: comparison of VSV-G and amphotropic vectors for hepatic gene transfer," *J. Virol.*, 70:2497–2502, 1996.

Macejak and Sarnow, *Nature*, 353:90–4, 1991.

Mann et al., *Cell*, 33:153–59,1983.

Markowitz et al., *J. Virol.*, 62:1120–1124, 1988.

Mason et al., *Am. J. Respir. Cell Mol. Biol.*, 11:561–567, 1994.

Massuda et al., *Proc Nat'l. Acad. Sci USA*, 94(26):14701–14706, 1997.

Matsura et al., *Brit. J. Cancer*, 66:1122–1130, 1992.

McCormack, Martineau, DePolo, Malfert, Akabarian, Townsend, Lee, Irwin, SaJiadi, Jolly, Warner, "Anti-vector immunoglobulin induced by retroviral vectors," *Hum. Gene Ther.* 8:1263–1273, 1997.

McCray et al., *Am. J. Respir. Cell Mol. Biol.*, 9:578–585, 1993.

McCray et al., *Gene Ther.*, 8:1087–1093, 1997a.

McCray Jr., Armstrong, Zabner, Miller, Koretzky, Couture, Robillard, Smith, Welsh, "Adenoviral-mediated gene transfer to fetal pulmonary epithelia in vitro and in viva," *Clin. Invest.*, 95:2620–2632, 1995.

McCray Jr., Wang, O'Brien, Davidson, Thomas, "Proliferation indices of pulmonary epithelia during human and ovine lung development: gene transfer targets for integrating vectors" *Cell Vision*, 4:1–8, 1997b.

McCray Jr., Zabner, Jia, Welsh, Thorne, "Efficient killing of inhaled bacteria in deltaF508 mice: role of airway surface liquid composition," *Am. J. Physiol*, 277:L183–L190, 1999.

McElvaney and Crystal, *Nature Med.* 1:182–184, 1995.

Merlo et al., *Nat Med.* 1(7): 686–692, 1995.

Michel and Westhof, *J. Mol. Biol.*, 216:585–610, 1990.

Miller and Miller, *J. Virol.*, 68:8270–8276, 1994.

Miller, Edwards, Miller, *Proc. Nat'l Acad. Sci. USA* 91:78–82, 1994.

Miller, *Proc. Nat'l Acad. Sci. USA*, 93:11407–11413, 1996.

Miyoshi et al., *Proc. Nat'l Acad. Sci. USA* 94:10319–10323, 1997.

Morgan, Nussbaum, Muenchau, Shu, Couture, Anderson, "Analysis of the functional and host range-determinning regions of the murine ectropic and amphotropic retrovirus envelope proteins," *J. Virol.*, 67:4712–4721, 1993.

Mori et al., *Cancer Res.*, 54:3396–3397, 1994.

Naldini, Blomer, Gallay. Ory, Mulligan, Gage, Verma, Trono, "In vivo gene delivery and stable transduction of nondividing cells by a lentiviral vector," *Science*, 272:263–267, 1996.

Nicolas and Rubinstein, In: *Vectors: A survey of molecular cloning vectors and their uses*, Rodriguez and Denhardt, eds., Stoneham: Butterworth, pp. 494–513, 1988.

Nicolau et al., Methods Enzymol., 149:157–176, 1987.

Nobri et al., *Nature*, 368:753–756, 1995.

Obrink, *BioEssays*, 13:227–233, 1991.

Odin and Obrink, *Exp. Cell Res.*, 171:1–15, 1987.

Ohmichi, Matsumoto, Nakamura, *Am. J. Physiol.*, 270:L1031–L1039, 1996.

Okamoto et al., *Proc. Nat'l Acad. Sci. USA*, 91:11045–11049, 1994.

Olivierio, et al., *EMBO J.*, 6(7):1905–1912, 1987.

Olsen et al., *Nucleic Acids Res.*, 21 (3):663–669, 1993.

Olsen, "Gene transfer vectors derived from equine infectious anemia virus," *Gene Ther.*, 5:1481–1487, 1998.

Olsen, Johnson, Stutts, Sarkadi, Yankaskas, Swanstrom, Boucher, "Correction of the apical membrane chloride permeability defect in polarized cystic fibrosis airway epithelia following retroyiral-mediated gene transfer," *Hum. Gene Ther.* 3:253–266, 1992.

O'Neal, Hasty, McCray Jr., Casey, Rivera-Perez, Welsh, Beaudet, Bradley, "A severe phenotype in mice with a duplication of exon 3 in the cystic fibrosis locus," *Hum. Mol. Genet.*, 2:1561–1569, 1993.

Orlic et al., *Proc. Nat'l Acad. Sci. USA*, 93:1109–11102, 1996.

Orlow et al., *Cancer Res.*, 54:2848–2851, 1994.

Panos, Rubin, Aaronson, Mason, *J. Clin. Invest.*, 92:969–977, 1993.

Paskind et al., *Virology*, 67:242–248,1975.

PCT Publication WO 90/07469

PCT Publication WO 93/12240

PCT Publication WO 96/22765

PCT Publication WO 96/27393

PCT Publication WO 96/32116

Pelletier and Sonenberg, *Nature*, 334:320–325, 1988.

Pendleton et al., Green, *J. Pathol.*, 170:169–172, 1993.

Perales et al., *Proc. Nat'l. Acad. Sci.* 91:4086–4090, 1994.

Pickles, McCarty, Matsui, Hart, Randell, Boucher, "Limited entry of adenovirus vectors into well-differentiated airway epithelium is responsible for inefficient gene transfer," *J. Virol*, 72:6014–6023, 1998.

Pitt et al., *Gene Ther.*, 2:344–350, 1995.

Plopper, Nishio, Kass, Hyde, "The role of the nonciliated bronchiolar epithelial (Clara) cell as the progenitor cell during bronchiolar epithelial differentiation in the perinatal rabbit lung," *Am. J. Respir. Cell Mol. Biol.*, 7:606–613, 1992.

Poeschla, Staal, Looney, "Efficient transduction of nondividing human cells by feline immunodeficiency virus lentiviral vectors," *Nature Med.*, 4:354–357, 1998.

Poli and Cortese, *Proc. Nat'l Acad. Sci. USA*, 86:8202–8206, 1989.

Prowse and Baumann, *Mol Cell Biol*, 8(1):42–51, 1988.

Qing, Khuntirat, Mah, Kube, Wang, Ponnazhagan, Zhou, Dwarki, Yoder, and Srivastava, "Adeno-associated virus type 2-mediated gene transfer. Correlation of tyrosine phosphorylation of the cellular single-stranded D sequence-binding protein with transgene expresion in human cells in vitro and murine tissues in vivom," *J. Virol.* 72, 1593–1599, 1998.

Qing, Wang, Kube, Ponnazhagan, Bajpai, and Srivastava, "Role of tyrosine phosphorylation of a cellular protein in adeno-associated virus 2-mediated transgene expression," *Proc. Natl. Acad. Sci. U.S.A.* 94, 10879–10884, 1997.

Quinton, *FASEB J* 4:2709–2717, 1990.

Ragot et al., *Nature*, 361:647–650, 1993.

Ramsey, "Drug therapy—Management of pulmonary disease in patients with cystic fibrosis [Review]," *N. Eng. J. Med.,* 335:179–188, 1996.

Randell, "Progenitor-progeny relationships in airway epithelium," *Chest,* 101(3)supp.:11S–16S, 1992.

Reinhold-Hurek and Shub, *Nature,* 357:173–176, 1992.

Rich et al., *Hum. Gene Ther.,* 4:461–476, 1993.

Rich, Anderson, Gregory, Cheng, Paul, Jefferson, McCann, Klinger, Smith, Welsh, Expression of cystic fibrosis transmembrane conductance regulator corrects defective chloride channel regulation in cystic fibrosis airway epithelial cells,. *Nature,* 347:358–363, 1990.

Richardson and Bank, *Mol. Cell. Biol.,* 16:4240–4247, 1996.

Ridgeway, In: *Vectors: A Survey of Molecular Cloning Vectors and Their Uses, Rodriguez et al., eds., Stoneham: Butterworth, pp.* 467–492, 1988.

Rodi, Iotti, Galbusera, Mencherini, Raimondi, Braschi, "Whole lung lavage," *Monaldi Arch. Chest Dis.,* 50:64–66, 1995.

Rodriguez et al., *J. Virol.,* 65:494–498, 1991.

Rommens, Iannuzzi, Kerem, Drumm, Melmer, Dean, Rozmahel, Cole, Kennedy, Hidaka, Zsiga, Buchwald, Riordan, Tsui, Collins, "Identification of the cystic fibrosis gene: chromosome walking and jumping," *Science,* 245:1059–1065, 1989.

Ron et al., *Mol. Cell. Biol.,* 2887–2895, 1991.

Rosenfeld et al., *Cell,* 68:143–155, 1992.

Rosenfeld et al., *Science,* 252:431–434, 1991.

Rubin, J. S., Bottaro, D. P., Chedid, M. Miki, T., Ron, D., Cheon, G., Taylor, W. G., Fortney, E., Sakata, H., and Finch, P. W. (1995). Keratinocyte growth factor. Cell Biol. Int. 19, 399–411.

Russell, Alexander, and Miller, "DNA synthesis and topoisomerase inhibitors increase transduction by adeno-associated virus vectors," *Proc. Natl. Acad. Sci. U.S.A.* 92, 5719–5723, 1995.

Russell, Miller, and Alexander, "Adeno-associated virus vectors preferentially transduce cells in S phase," *Proc. Natl. Acad. Sci. U.S.A.* 91, 8915–8919, 1994.

Sarver et al., *Science,* 247:1222–1225, 1990.

Scanlon et al., *Proc. Nat'l Acad. Sci. USA,* 88:10591–10595, 1991.

Scaria, St. George, Jiang, Kaplan, Wadsworth, Gregory, "Adenovirus-mediated persistent cystic fibrosis transmembrane conductance regulator expression in mouse airway epithelium," *J. Virol.,* 72:7302–7309, 1998.

Schlegel et al., *Cell* 32:639–646, 1983.

Serrano et al., *Nature,* 366:704–707, 1993.

Serrano et al., *Science,* 267:249–252, 1995.

Shami, Evans, "Kinetics of pulmonary cells. In Comparative biology of the normal lung," R. A. Parent, editor. CRC Press, Boca Raton, 145–155, 1991.

Simon, Engelhardt, Yang, Zepeda, Weber-Pendleton, Grossman, Wilson, "Adenovirus-mediated transfer of the CFTR gene to lung of nonhuman primates: toxicity study," *Hum. Gene Ther.,* 4:771–780, 1993.

Smith, Travis, Greenberg, Welsh, "Cystic fibrosis airway epithelia fail to kill bacteria because of abnorrrial airway surface fluid," *Cell,* 85:229–236, 1996.

Snouwaert, Brigman, Latour, Iraj, Schwab, Gilmour, Koller, "A murine model of cystic fibrosis," *Am. J. Respir. Crit. Care Med.* 151:S59–S64, 1995.

Srivastava et al., *J. Virol,* 45:555–564, 1983.

Stern, M., Caplen, N. J., Browning, J. E., Griesenbach, U., Sorgi, F., Huang, L. Gruenert, D. C., Marriot, C., Crystal, R. G., Geddes, D. M., and Alton, E. W. (1998). The effect of mucolytic agents on gene transfer across a CF sputum barrier in vitro. Gene Ther. 5, 91–98.

Stewart, Deacon, "Vital fluorochromes as tracers for fungal growth studies," *Biotech Histochem,* 70:57–65, 1995.

Stratford-Perricaudet and Perricaudet, In: *Human Gene Transfer,* O. Cohen-Haguenauer et al., eds., John Libbey Eurotext, France, pp. 51–61, 1991.

Stratford-Perricaudet et al., *Hum. Gene. Ther.,* 1:241–256, 1990.

Summerford, C., and Samulski, R. J. (1998). Membrane-associated heparan sulfate proteoglycan is a receptor for adeno-associated virus type 2 virions. J. Virol. 72, 1438–1445.

Takahashi et al., *Cancer Res.,* 52:734–736, 1992.

Temin, In: *Gene Transfer,* Kucherlapati (ed.), New York: Plenum Press, pp. 149–188, 1986.

Teramoto, Bartlett, McCarty, Xiao, Samulski, Boucher, "Factors influencing adeno-associated virus-mediated gene transfer to human cystic fibrosis airway epithelial cells: comparison with adenovirus vectors," *J. Virol.,* 72:8904–8912, 1998.

Thomas and Roth, "The basolateral targeting signal in the cytoplasmic domain of glycoprotein G from vesicular stomatitis virus resembles a variety of intracellular targeting motifs related by promary sequence but having diverse targeting activities," *J. Biol. Chem.,* 269:15732–15739, 1994.

Tugizov, Maidji, Pereira, *J. Ger Virol.,* 77:61–74, 1996.

U.S. Pat. No. 5,139,941
U.S. Pat. No. 5,196,335
U.S. Pat. No. 5,252,479
U.S. Pat. No. 5,354,855
U.S. Pat. No. 5,359,046
U.S. Pat. No. 5,543,399
U.S. Pat. No. 5,641,662
U.S. Pat. No. 5,756,353

Ulich, Yi, Longmuir, Yin, Biltz, Morris, Housley, Pierce, "Keratinocyte growth factor is a growth factor for type II pneumocytes in vivo," *J. Clin. Invest.,* 93:1298–1306, 1994.

Umbas et al., *Cancer Res.,* 52:5104–5109, 1992.

van Zeijl et al., *Proc. Nat'l Acad. Sci. USA,* 91:1168–1172, 1994.

Varmus et al., *Cell,* 25:23–36, 1981.

Vogelstein el al., *Genes Chromosomes Cancer,* 2:(2) 159–162, 1990.

Wagner et al., *Proc. Natl. Acad. Sci.* 87, 9:3410–3414, 1990.

Walters, Grunst, Bergelson, Finberg, Welsh, Zabner, 1999 "Basolateral localization of fiber receptors limits adenovirus infection of airway epithelia," *J. Biol. Chem.,* 274:10219–10226, 1999.

Walther and Stein, *J. Mol. Med,* 74:379–392, 1996.

Wang, Davidson, Melchert, Slepushkin, vanEs, Bodner, Jolly, McCray, Jr., "Influence of cell polarity on retrovirus-mediated gene transfer to differentiated human airway epithelia," *J. Virol.,* 72:9818–9826, 1998.

Wang, Slepushkin, Bodner, Zabner, vanEs, Thomas, Jolly, Davidson, McCray Jr., "Keratinocyte growth factor induced epithelial proliferation facilitates retroviral-mediated gene transfer to pulmonary epithelia in vivo," *J. Gene. Med.,* 1:22–30, 1999.

Weinberg, *Biochemistry,* 28:8263–8269, 1989.

Weinberg, *Science,* 254:1138–1145, 1991.

Weiss and Tailor, *Cell,* 82:531–533, 1995.

Welsh et al., In: *The Metabolic and Molecular Basis of Inherited Disease,* C. R. Scriver, A. L. Beaudet, W. S. Sly, and D. Valle, editors. McGraw-Hill, Inc., New York, N.Y. 3799–3876, 1995.

Welsh et al., *Neuron,* 8:821–829, 1992.

Widdecombe, J. H., Azizi, F., Kang, T., and Pittet, J. F. (1996). Transient permeabilization of airway epithelium by mucosal water. J. Appl. Physiol. 81, 491–499.
Widdicombe, Azizi, Kang, Pittet, "Transient permeabilization of airway epithelium by mucosal water," *J. Appl Physiol.*, 81:491–499, 1996.
Widdicombe, Azizi, Kang, Pittet, *J. Appl. Physiol.*, 81:491–499, 1996.
Wilson, et al., *Mol. Cell. Biol.*, 6181–6191, 1990.
Wong et al., Gene, 10:87–94, 1980.
Wu and Wu, Adv. Drug Delivery Rev., 12:159–167, 1993.
Wu and Wu, J. Biol. Chem., 262:4429–4432, 1987.
Wu et al., *J. Virol.*, 68:1615–1623, 1994.
Yamaya, Finkbeiner, Chun, Widdicombe, "Differentiated structure and function of cultures from human tracheal epithelium," *Am. J. Physiol.*, 262:L713–L724, 1992.
Yamaya, Finkbeiner, Widdicombe, *Am. J. Physiol.* 261:L491–L494, 1991.
Yang et al., *J. Virol.*, 69:2004–2015, 1995.
Yap, Brieher, Gumbiner, "Molecular and functional analysis of cadherin-based adherens junctions," *Annu Rev. Cell Dev. Biol.*, 13:119–146, 1997.
Zabner et al., *Cell* 75:207–216, 1993.
Zabner, Fasbender, Moninger, Poellinger, Welsh, "Cellular and molecular barriers to gene transfer by a cationic lipid," *J. Biol. Chem.*, 270:18997–19007, 1995.
Zabner, Ramsey, Meeker, Aitken, Balfour, Gibson, Launspach, Moscicki, Richards, Standaert, Williams-Warren, Wadsworth, Smith, Welsh, "Repeat administration of an adenovirus vector encoding cystic fibrosis transmembrane conductance regulator to the nasal epithelium of patients wvith cystic fibrosis." *J. Clin. Invest.*, 97:1504–1511, 1996.
Zabner, Smith, Karp, Widdicombe, Welsh, "Loss of CFTR chloride channels alters salt absorption by cystic fibrosis airway epithelia in vitro," *Mol. Cell*, 2:397–403, 1998.
Zabner, Zeiher, Friedman, Welsh, "Adenovirus-mediated gene transfer to ciliated airway epithelia requires prolonged incubation time," *J. Virol.*, 70:6994–7003, 1996.
Zechner et al., *Mol. Cell. Biol.*, 2394–2401, 1988.
Zeiher, Eichwald, Zabner, Smith, Puga, McCray Jr., Capecchi, Welsh, Thomas, "A mouse model for the ΔF508 allele of cystic fibrosis," *J. Clin. Invest.* 96:2051–2064, 1995.
Zhang, Y., Doranz, B., Yaaskas, J. R. and Engelhardt, J. F. (1995). Genotypic analysis of respiratory mucous sulfation defects in cystic fibrosis. J. Clin. Invest. 96, 2997–3004.
Zhang, Y., Jiang, Q., Dudus, L., Yankaskas, J. R., and Engelhardt, J. F. (1998). Vector-specific complementation profiles of two independent primary defects in cystic fibrosis airways. Hum. Gene Ther. 9, 635–648.
Zsengeller, Halbert, Miller, Wert, Whitsett, Bachurski, "Keratinocyte growth factor stimulates transduction of the respiratory epithelium by retroviral vectors," *Hum. Gene Ther.*, 10:341–353, 1999.
Zsengeller, Wert, Hull, Hu, Yei, Trapnell, Whitsett, "Persistence of replication-deficient adenovirus-mediated gene transfer in lungs of immune-deficient (nu/nu) mice, *Hum. Gene Ther.*, 6:457–467, 1995.

What is claimed is:

1. A method for increasing viral vector infection of epithelial cells in an epithelial tissue comprising:
   a) contacting said epithelial tissue with a composition that comprises a hypotonic solution and/or a chelator of divalent cations in an amount sufficient to produce permeabilized epithelial tissue; and
   b) contacting said permeabilized epithelial tissue with a viral vector;
   whereby an increase in transepithelial permeability increases viral vector infection of said epithelial cells.

2. The method of claim 1, wherein said epithelial cells are in airway epithelial tissue.

3. The method of claim 2, wherein said airway epithelial tissue is bronchial or bronchiolar tissue.

4. The method of claim 2, wherein said airway epithelial tissue is tracheal tissue.

5. The method of claim 2, wherein said airway epithelial tissue is alveolar tissue.

6. The method of claim 1, further comprising increasing the proliferation of said epithelial cells.

7. The method of claim 6, wherein increasing the proliferation of said epithelial cells is achieved by contacting said cells with a proliferative factor.

8. The method of claim 7, wherein said proliferative factor is a growth factor.

9. The method of claim 1, wherein said composition comprises a hypotonic solution.

10. The method of claim 1, wherein said composition comprises a chelator of divalent cations.

11. The method of claim 10, wherein said chelator of divalent cations is EGTA, BAPTA or EDTA.

12. The method of claim 1, further comprising, infecting said epithelial cells in said permeabilized tissue with a virus vector selected from the group consisting of a retrovirus, a lentivirus, an adenovirus, an adeno-associated virus, a parvovirus, a papovavirus, paramyxovirus and a vaccinia virus.

13. The method of claim 12, wherein the virus vector comprises a non-viral gene under the control of a promoter active in eukaryotic cells.

14. The method of claim 13, wherein said non-viral gene is a human gene.

15. The method of claim 14, wherein said gene encodes a polypeptide selected from the group consisting of a tumor suppressor, a cytokine, an enzyme, a toxin, a growth factor, a membrane channel, an inducer of apoptosis, a transcription factor, a hormone and a single chain antibody.

16. The method of claim 12, wherein the virus vector is a replication-defective virus.

17. The method of claim 16, wherein the virus vector is a retroviral vector.

18. The method of claim 1, wherein said epithelial tissue is diseased.

19. The method of claim 18, wherein said disease is lung cancer, tracheal cancer, asthma, surfactant protein B deficiency, alpha-1-antitrypsin deficiency or cystic fibrosis.

20. The method of claim 7, wherein said proliferative factor is delivered as an aerosol.

21. The method of claim 7, wherein said proliferative factor is delivered as a topical solution.

22. The method of claim 1, wherein said composition is delivered as an aerosol.

23. The method of claim 1, wherein said composition is delivered as a topical solution.

24. An in vivo method for redistributing viral receptors on an epithelial cell of an epithelial tissue from the basolateral side to the apical side of said epithelial cell comprising increasing the transepithelial permeability of said epithelial tissue by contacting said epithelial tissue with a hypotonic solution and/or a chelator of divalent cations whereby increased transepithelial permeability facilitates redistribution of said viral receptors on said epithelial cell.

25. The method of claim 24, wherein said receptor is a retroviral receptor.

26. A method for expressing a polypeptide in cells of an epithelial tissue comprising:

(a) providing a packaged viral vector comprising a polynucleotide encoding said polypeptide;

(b) increasing the permeability of said epithelial tissue by treating said tissue with a hypotonic solution and/or a chelator of divalent cations; and (c) contacting cells of the permeabilized epithelial tissue with said packaged viral vector under conditions permitting the uptake of said packaged viral vector by said cells and expression of said polypeptide therein;

whereby increased permeability of said epithelial tissue facilitates improved viral transduction of said cells, which in turn facilitates expression of said polypeptide.

27. The method of claim 26, further comprising increasing the proliferation of cells of said epithelial tissue.

28. The method of claim 26, wherein said viral vector is a retroviral vector.

29. A method of increasing transport of chloride ions in airway epithelial tissue of a mammal suffering from cystic fibrosis comprising:

a) providing a packaged viral vector comprising a polynucleotide encoding a cystic fibrosis transmembrane regulator (CFTR) protein;

b) contacting said airway epithelial tissue with a hypotonic solution and/or a chelator of divalent cations in a sufficient amount to produce permeabilized epithelial tissue; and c) contacting cells of said permeabilized airway epithelial tissue with said packaged viral vector under conditions permitting uptake of the packaged viral vector by said cells, and expression of said CFTR protein therein;

wherein a sufficient quantity of said CFTR protein is produced to increase chloride ion transport in the airway epithelial tissue.

30. The method of claim 29, further comprising increasing the proliferation of cells of said epithelial tissue.

31. The method of claim 29, wherein said airway tissue is alveolar tissue, bronchial tissue or tracheal tissue.

32. The method of claim 29, wherein increasing the proliferation of cells of said diseased epithelial tissue comprises contacting said cells with a proliferative agent.

33. The method of claim 29, wherein said viral vector is a retroviral vector.

34. A method for transducing epithelial cells with a viral vector comprising delivering to said epithelial cells a packaged viral vector and EGTA in a hypotonic solution.

* * * * *